(12) United States Patent
Arnold et al.

(10) Patent No.: US 7,435,570 B2
(45) Date of Patent: *Oct. 14, 2008

(54) THERMOSTABLE PEROXIDE-DRIVEN CYTOCHROME P450 OXYGENASE VARIANTS AND METHODS OF USE

(75) Inventors: Frances H. Arnold, Pasadena, CA (US); Patrick C. Cirino, State College, PA (US)

(73) Assignee: California Institute of Technology, Pasadena, CA (US)

( * ) Notice: Subject to any disclaimer, the term of this patent is extended or adjusted under 35 U.S.C. 154(b) by 373 days.

This patent is subject to a terminal disclaimer.

(21) Appl. No.: 10/916,369

(22) Filed: Aug. 11, 2004

(65) Prior Publication Data

US 2005/0037411 A1 Feb. 17, 2005

Related U.S. Application Data

(60) Provisional application No. 60/494,309, filed on Aug. 11, 2003.

(51) Int. Cl.
- C12N 9/02 (2006.01)
- C12N 15/00 (2006.01)
- C12Q 1/26 (2006.01)
- C12P 21/04 (2006.01)
- C07H 21/04 (2006.01)

(52) U.S. Cl. .................. 435/189; 435/440; 435/25; 435/69.1; 435/71.1; 536/23.2

(58) Field of Classification Search .................. None
See application file for complete search history.

(56) References Cited

U.S. PATENT DOCUMENTS

| | | | |
|---|---|---|---|
| 4,599,342 A | 7/1986 | LaHann | |
| 5,605,793 A | 2/1997 | Stemmer | |
| 5,741,691 A | 4/1998 | Arnold et al. | |
| 5,785,989 A | 7/1998 | Stanley et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,945,325 A | 8/1999 | Arnold | |
| 5,965,408 A | 10/1999 | Short | |
| 6,090,604 A | 7/2000 | Golightly et al. | |
| 6,361,988 B1 | 3/2002 | Arnold | |
| 6,498,026 B2 | 12/2002 | Delagrave et al. | |
| 6,524,837 B1 | 2/2003 | Arnold | |
| 6,537,746 B2 | 3/2003 | Arnold | |
| 6,643,591 B1 | 11/2003 | Korzekwa et al. | |
| 6,794,168 B1 * | 9/2004 | Wong et al. | 435/189 |
| 6,906,930 B2 | 6/2005 | Arnold et al. | |
| 2003/0077795 A1 | 4/2003 | Wilson | |
| 2003/0077796 A1 | 4/2003 | Crotean | |
| 2003/0100744 A1 | 5/2003 | Farinas | |
| 2005/0037411 A1 | 2/2005 | Arnold et al. | |
| 2005/0202419 A1 * | 9/2005 | Cirino et al. | 435/6 |

FOREIGN PATENT DOCUMENTS

| | | |
|---|---|---|
| EP | 0 505 198 A1 | 9/1992 |
| WO | WO 89/03424 A1 | 4/1989 |
| WO | WO 95/22625 | 8/1995 |
| WO | WO 97/16553 A1 | 5/1997 |
| WO | WO 97/20078 | 6/1997 |
| WO | WO 97/35957 A1 | 10/1997 |
| WO | WO 97/35966 A1 | 10/1997 |
| WO | WO 98/27230 | 6/1998 |
| WO | WO 98/31837 A1 | 7/1998 |
| WO | WO 98/41653 | 9/1998 |
| WO | WO 98/42832 | 10/1998 |
| WO | WO 99/60096 | 11/1999 |
| WO | WO 00/00632 A1 | 1/2000 |
| WO | WO 00/04190 A1 | 1/2000 |
| WO | WO 00/06718 A2 | 2/2000 |
| WO | WO 00/09679 A1 | 2/2000 |
| WO | WO 00/18906 A3 | 4/2000 |
| WO | WO 00/31273 A2 | 6/2000 |
| WO | WO 00/78973 | * 12/2000 |
| WO | WO 01/62938 A2 | 8/2001 |
| WO | WO 02/083868 | 10/2002 |
| WO | WO 03/008563 | 1/2003 |

OTHER PUBLICATIONS

Branden et al. Introduction to Protein Structure, Garland Publishing Inc., New York, p. 247, 1991.*

(Continued)

*Primary Examiner*—Yong D Pak
(74) *Attorney, Agent, or Firm*—Gavrilovich Dodd & Lindsey LLP; Joseph R. Baker, Jr.

(57) ABSTRACT

The invention relates to novel variants of cytochrome P450 oxygenases. These variants have at least one mutation improving their ability to use peroxide as an oxygen donor as compared to the corresponding wild-type enzyme. The variants also have at least one mutation improving thermostability as compared to the parent enzyme or corresponding wild-type enzyme. Preferred variants include cytochrome P450 BM-3 heme domain variants having L52I, I58V, F87A, H100R, S106R, F107L, A135S, M145A/V, A184V, N239H, S274T, L324I, V340M, I366V, K434E, E442K, and/or V446I amino acid substitutions.

18 Claims, 13 Drawing Sheets

OTHER PUBLICATIONS

Appel et al., "A P450 BM-3 mutant hydroxylates alkanes, cycloalkanes, arenes and heteroarenes", Journal of Biotechnology, 88 (2001) pp. 167-171.

Arnold, "Design by Directed Evolution", Acc. Chem. Res., 1998, 31, pp. 125-131.

Beratan et al., "The protein bridge between redox centres", The Protein Electron Transfer, 1996, pp. 23-42.

Boddupalli et al., "Fatty Acid Monooxygenation by Cytochrome P-450BM-3", The American Society for Biochemistry and Molecular Biology, 1990, pp. 4233-4239.

Capdevila et al., "The Highly Stereoselective Oxidation of Polyunsaturated Fatty Acids by Cytochrome P450BM-3", The Journal of Biological Chemistry, 1996, vol. 271, No. 37, pp. 22663-22671.

Chang et al., "Homology Modeling, Molecular Dynamics Simulations, and Analysis of CYP119, a P450 Enzyme from Extreme Acidothermophilic Archaeon Sulfolobus solfataricus", Biochemistry, 2000, 39, pp. 2484-2498.

Chen et al., "Thermal, Catalytic, Regiospecific Functionalization of Alkanes", Science, vol. 287, 2000, pp. 1995-1997.

Farinas et al., "Directed Evolution of a Cytochrome P450 Monooxygenase for Alkane Oxidation", Advs. Synth. Catal., 2001, 343, No. 6-7, pp. 601-606.

Graham-Lorence et al., "An Active Site Substitution, F87V, Converts Cytochrome P450 BM-3 into a Regio- and Stereoselective (14S, 15R)-Arachidonic Acid Epoxygenase", The Journal of Biological Chemistry, vol. 272, No. 2, 1997, pp. 1127-1135.

Groves et al., "Models and Mechanisms of Cytochrome P450 Action", Cytochrome P450: Structure, Mechanism, and Biochemistry (Second Edition), 1995, pp. 3-49.

Haines et al., "Pivotal Role of Water in the Mechanism of P450BM-3", Biochemistry 2001, 40, pp. 13456-13465.

Joo et al., "Laboratory evolution of peroxide-mediated cytochrome P450 hydroxylation", Nature, 1999, 399, pp. 670-673.

Joo et al., "A high-throughput digital imaging screen for the discovery and directed evolution of oxytenases", Chemistry & Biology, 1999, vol. 6, No. 10, pp. 600-706.

Lewis et al., "Molecular modeling of CYP1 family enzymes CYP1A1, CYP1A2, CYP1A6 and CYP1B1 based on sequence homology with CYP102", Toxicology, 139, 1999, pp. 530-579.

Li et al., "Characterization of Recombinant *Bacillus megaterium* Cytochrome P-450BM-3 and ITs Two Functional Domains", The Journal of Biological Chemistry, vol. 266, No. 18, pp. 11909-11914.

Li et al., "Critical Role of the Residue Size at Position 87 in H2O2-Dependent Substrate Hydroxylation Activity and H2O2 Inactivation of Cytochrome P450BM-3", IDEAL, www.idealibrary.com, 2001, vol. 280, No. 5, pp. 1258-1261.

Li et al., "The Structure of the cytochrome P450OBM-3 haem domain complexed with the fatty acid substrate, palmitoleic acid", Nature Structural Biology, vol. 4, No. 2, 1997, pp. 140-146.

Lipman et al., "Rapid and Sensitive Protein Similarity Searches", Science, vol. 227, 1985, pp. 1435-1441.

Matsunaga et al., "Fatty Acid-Specific, Regiospecific, and Stereospecific Hydroxylation by Cytochrome P450 (CYP152B1) from *Sphingomonas paucimobilis*: Substrate Structure Required for α-Hydroxylation", Lipids, vol. 35, No. 4, 2000, pp. 365-371.

Miles et al., "Protein engineering of cytochromes P-450", Biochimica et Biophysica Acta, 1543, 2000, pp. 383-407.

Miura et al., "ω-1, ω-2 and ω-3 Hydroxylation of Long-Chain Fatty Acids, Amides and Alcolohols By A Soluble Enzyme System From *Bacillus megaterium*", Biochimica et Biophysica Acta, 1975, 388, pp. 305-317.

Moser et al., "Biological Electron Transfer", Journal of Bioenergetics and Biomembranes, 1995, vol. 27, No. 3, pp. 263-274.

Munro et al., "Probing electron transfer in flavocytochrome P-450 BM3 and its component domains", Eur. J. Biochem., 239, 1996, pp. 403-409.

Nakagawa et al., "Construction of Catalase Deficient *Escherichia coli* Strains for theProduction Uricase", Biosci. Biotech. Biochem., vol. 60, No. 3, 1996, pp. 415-420.

Narhi et al., "Characterization of a Catalytically Self-sufficient 119,000-Dalton Cytochrome P-450 Monooxygenase Induced by Barbiturates in *Bacillus megaterium*", The Journal of Biological Chemistry, vol. 261, No. 16, 1986, pp. 7160-7169.

Narhi et al., "Identification and Characterization of Two Functional Domains in Cytochrome P-450BM-3, a Catalytically Self-sufficient Monooxygenase Induced by Barbiturates in *Bacillus megaterium*", The Journal of Biological Chemistry, vol. 262, No. 14, 1987, pp. 6683-6690.

Oliver et al., "A Single Mutation in Cytochrome P450 BM3 Changes Substrate Orientation in a Catalytic Intermediate and the Regiospecificity of Hydroxylation", Biochemistry, vol. 36, No. 7, 1997, pp. 1567-1572.

Omura et al., "The Carbon Monoxide-binding Pigment of Liver Microsomes", The Journal of Biological Chemistry, vol. 239, No. 7, 1964, pp. 2379-2385.

Nelson, "Cytochrome P450 Nomenclature and Alignment of Selected Sequences", Cytochrome P450: Structure, Mechanism, and Biochemistry (Second Edition), 1995, pp. 575-606.

Paulsen et al., "Dramatic Differences in the Motions of the Mount of Open and Closed Cytochrome P450BM-3 by Molecular Dynamics Simulations", Proteins: Structure, Function and Genetics, vol. 21, 1995, pp. 237-243.

Pearson et al., "Improved tools for biological sequence comparison", Proc. Natl. Acad. Sci. USA, 1988, vol. 85, pp. 2444-2448.

Peterson et al., "Bacterial P450s—Structural Similarities and Funtional Differences", Cytochrome P450: Structure, Mechanism and Biochemistry (Second Edition), 1995, pp. 151-180.

Roberts, "The power of evolution: Accessing the synthetic potnetial of P450s", Chemistry & Biology, 1999, vol. 6, No. 10, pp. R269-R272.

Ruettinger et al., "Epoxidation of Unsaturated Fatty Acids by a Soluble Cytochrome P-450-dependent System from *Bacillus megaterium*", The Journal of Biological Chemistry, 1981, vol. 256, No. 11, pp. 5728-5734.

Ruettinger et al., "Coding Nucleotide, 5' Regulatory, and Deduced Amino Acid Sequences of P-450BM3, a Single Peptide Cytochrome P-450:NADPH-P-450 Reductase from *Bacillus megaterium*", The Journal of Biological Chemistry, vol. 264, No. 19, 1989, pp. 10987-10995.

Scwaneberg et al., "A Continuous Spectrophotometric Assay for P450BM-3, a Fatty Acid Hydroxylating Enzyme, and Its Mutant F87A", Analytical Biochemistry, vol. 269, 1999, pp. 359-366.

Scwaneberg et al., "P450 monooxygenase in biotechnology Single-step, large-scale purification method for cytochrome P450 BM-3 by anion-exchange chromatography", Journal of Chromatography A., vol. 848, 1999, pp. 149-159.

Schwaneberg et al., "Cost-Effective Whole-Cell Assay for Laboratory Evolution of Hydroxylases in *Escherichia coli*", Journal of Biomolecular Screening, 2001, vol. 6, No. 2, pp. 111-117.

Shilov et al., "Activation of C-H Bonds by Metal Complexes", Chem. Rev., 1997, vol. 97, pp. 2879-2932.

Thomas et al., "Molecular Sieve Catalysts for the Regioselective and Shape-Selective Oxyfunctionalization of Alkanes in Air" Acc. Chem. Res., 2001, vol. 34, pp. 191-200.

van Deurzen et al., "Selective Oxidations Catalyzed By Peroxidases", Tetrahedron Report No. 427, vol. 53, No. 39, 1197, pp. 13183-13220.

Zhao et al., "Methods for Optimizing Industrial Enzymes by Directed Evolution", Manual of Industrial Microbiology and Biotechnology (Second Edition), pp. 597-604.

Govindaraj et al., "Role of the linker region connecting the reductase and heme domains in cytochrome P450BM-3", Biochemistry, 1995, vol. 34, No. 35, pp. 11221-11226.

Li et al., "Critical role of the residue size at position 87 in H2O2-dependent substrate hydroxlation activity and H2O2 inactivation of cytochrome P450BM-3", Biochem Biophys. Res Commun., 2001, vol. 280, No. 5, pp. 1258-1261.

Yeom et al., "The role of Thr268 in oxygen activation of cytochrome P450BM-3", Biochemistry, 1995, vol. 34, No. 45, pp. 14733-14740.

Ost et al., "Rational re-design of the substrate binding site of flavocytochrome P450 BM3", FEBS Lett., 2000, vol. 486, No. 2, pp. 173-177.

Noble et al., "Roles of key active-site residues in favocytochrome P450 BM3", Biochem. J., 1999, vol. 339, pp. 371-379.

Adam et al., "Microbial Asymmetric CH Oxidations of Simple Hydrocarbons: A Novel Monooxygenase Activity of the Topsoil Microorganism *Bacillus megaterium*," *Eur. J. Org. Chem.*, 2000, pp. 2923-2926, Wiley-VCH Verlag GmbH, Weinheim, Germany.

Aisaka et al., "Production of Galactose Oxidase by *Gibberella fujikuroi*," *Agric. Biol. Chem.*, 1981, pp. 2311-2316, 45(10).

Amaral et al., "Galactose Oxidase of *Polyporus circinatus*$^{1-4}$," *Methods in Enzymology, Carbohydrate Metabolism*, 1966, pp. 87-92, vol. 9, Academic Press Inc., New York, NY, USA.

Anfinsen, "Principles that Govern the Folding of Protein Chains," *Science*, Jul. 20, 1973, pp. 223-230, vol. 181, No. 4096, American Asso for the Advancement of Science, Washington, DC, USA.

Arkin et al., "An algorithm for protein engine ring: Simulations of recursive ensemble mutagenesis," *Proc. Natl. Acad. Sci.-USA*, Aug. 1992, pp. 7811-7815, vol. 89, Applied Biological Sciences.

Arnold, "Engineering proteins for nonnatural environments," *The FASEB Journal*, Jun. 1993, pp. 744-749, vol. 7, No. 6, FASEB, Bethesda, MD, USA.

Arnold et al., "Optimizing Industrial Enzymes by Directed Evolution," *Advances in Biochemical Engineering/Biotechnology*, 1997, pp. 1-14, vol. 58, Springer-Verlag, Berlin, Germany.

Arts et al., "Hydrogen Peroxide and Oxygen in Catalytic Oxidation of Carbohydrates and Related Compounds," *Synthesis Journal of Synthetic Organic Chemistry*, Jun. 1997, pp. 597-613.

Ashraf et al., "Bacterial oxidation of propane," *FEMS Microbiology Letters*, 1994, pp. 1-6, Federation of European Microbiological Societies, Elsevier.

Avigad, "Oxidation Rates of Some Desialylated Glycoproteins by Galactose Oxidase," *Archives of Biochemistry and Biophysics*, Jun. 1985, pp. 531-537, vol. 239, No. 2, Academic Press, Inc.

Avigad, "An NADH Coupled Assay System for Galactose Oxidase," *Analytical Biochemistry*, 1978, pp. 470-476, 86, Academic Press, Inc.

Avigad et al., "The D-Galactose Oxidase of *Polyporus circinatus*," *Journal of Biological Chemistry*, Sep. 1962, pp. 2736-2743, vol. 237, No. 9, American Society of Biological Chemists, Baltimore, MD, USA.

Barnes, "Maximizing Expression of Eukaryotic Cytochrome P450s in *Escherichia coli*," *Methods in Enzymology, Cytochrome P450, Part B*, 1996, pp. 3-14, vol. 272, Academic Press, Inc., San Diego, CA, USA.

Baron et al., "Structure and Mechanism of Galactose Oxidase," *The Journal of Biological Chemistry*, Sep. 23, 1994, pp. 25095-25105, vol. 269, No. 38, American Soc for Biochemistry and Molecular Biology.

Benson et al., "Regulation of Membrane Peptides by the *Pseudomonas* Plasmid *alk* Regulon," *Journal of Bacteriology*, Dec. 1979, pp. 754-762, vol. 140, No. 3.

Abecassis et al., Nucleic Acids Res., 2000, vol. 28, E88.

Abecassis et al., "Design and characterization of a novel family-shuffling technology adapted to membrane enzyme: application to P450s involved in xenobiotic metabolism," adv. Exp. Med. Biol. 500, 2001, pp. 319-322.

Abecassis et al., "Exploration of natural and artificial sequence spaces: Towards a functional remodeling of membrane-bound cytochome P450," Biocatal. Biotransform, 2003, vol. 21, No. 2, pp. 55-66.

Assis et al., "Hydrocarbon oxidation with iodosylbenzene catalyzed by the sterically hindered iron (iii)5-(pentafluorophenyl)-10, 15, 20-tris(2,6-dichlorophenyl) porphyrin in homogenous solution and covalently bound to silica," Journal of the Chemical Society-Perkin Transactions 2, 1998, vol. 10, pp. 2221-2226.

Barnes et al., "Expression and enzymatic activity of recombinant cytochrome P450 17α-hydroxylase in *Escherichia coli*," Proc. Natl. Acad. Sci. USA, Jul. 1991, vol. 88, pp. 5597-5601.

Bell et al., "Butane and propane oxidation by engineered cytochromes P450(cam)," Chemical Communications, 2002, vol. 5, pp. 490-491.

Bell et al., "Engineering Cytochrome P450cam into an alkane hydroxylase," Dalton Transactions, 2003, vol. 11, pp. 2133-2140.

Better et al., "*Escherichia coli* Secretion of an Active Chimeric Antibody Fragment," *Science*, May 20, 1988, pp. 1041-1043, vol. 240, American Asso for the Advancement of Science, Washington, DC, USA.

Blay et al., "Alkane oxidation by a carbonxylate-bridged dimanganese (III) complex," Chemical Communications, 2001, vol. 20, pp. 2102-2103.

Boddupalli et al., "Fatty Acid Monooxygenation by P450$_{BM-3}$: Product identification and Proposed Mechanisms for the Sequential Hydroxylation Reactions," Archives of Biochemistry and Biophysics, Jan. 1992, pp. 20-28, vol. 292, No, 1, Academic Press, Inc.

Boddupalli et al., "Fatty Acid Monooxygenation by P450$_{BM-3}$," The Journal of Biological Chemistry, 1990, pp. 4233-4239.

Bogarad et al., "A hierarchical approach to protein molecular evolution," *Proc. Natl. Acad. Sci USA*, 1999, vol. 96, pp. 2591-2595.

Borman et al., "Kinetic studies on the reactions of *Fusarium* galactose oxidase with five different substrates in the presence of dioxygen," *Journal of Biological Inorganic Chemistry*, 1997, pp. 480-487, Society of Biological Inorganic Chemistry.

Bradford, "A Rapid and Sensitive Method for the Quantitation of Microgram Quantities of Protein Utilizing the Principle of Protein-Dye Binding," *Analytical Biochemistry*, pp. 248-254, 1976.

Calderhead, D. et al., "Labeling of Glucose Transporters at the Cell Surface in 3T3-L1 Adipocytes," *The Journal of Biological Chemistry*, Sep. 5, 1988, pp. 12171-12174, vol. 263, No. 25, The American Society for Biochemistry and Molecular Biology.

Calvin, N. et al., "High-Efficiency Transformation of Bacterial Cells by Electroporation," *Journal of Bacteriology*, Jun. 1988, pp. 2796-2801, vol. 170, No. 6, American Society for Microbiology.

Campbell et al., "Chimeric proteins can exceed the sum of their parts: Implications for evolution and protein design," Nat. Biotechnol., May 1997, vol. 15, pp. 439-443.

Cameron, A., "Two cradles for the heavy elements," Nature, Jan. 15, 1998, pp. 228-231, vol. 39.

Carmichael, A. et al., "Protein engineering of *Bacillus megaterium* CYP102," Eur. J. Biochem., 2001, pp. 3117-3125, vol. 268, FEBS.

Castelli, L. et al., "High-level secretion of correctly processed β-lactamase from *Saccharomyces cerevisiae* using a high-copy-number secretion vector," Gene, 1994, pp. 113-117, vol. 142, Elsevier Science B.V.

Chang, C. et al., "Evolution of a cytokine using DNA family shuffling," Nature Biotechnology, Aug. 1999, pp. 793-797, vol. 17.

Chavez et al., "Syntheses, structures, and reactivities of cobalt (III)-alkylperoxo complexes and their role in stoichiometric and catalytic oxidation of hydrocarbons," Journal of the American Chemical Society, 1998, vol. 120, No. 35, pp. 9015-9027.

Chen, K. et al., "Tuning the activity of an enzyme for unusual environments: Sequential random mutagenesis of subtilisin E for catalysis in dimethylformamide," Proc. Natl. Acad. Sci. USA, Jun. 15, 1993, pp. 5618-5622, vol. 90, No. 12.

Chen et al., "Stereospecific alkane hydroxylation by non-heme iron catalysts: mechanistic evidence for an Fe-V = O active species," Journal of the American Chemical Society, 2001, vol. 123, No. 26, pp. 6327-6337.

Cherry, J. et al., "Directed evolution of a fungal peroxidase," Nature Biotechnology, Apr. 1999, pp. 379-384, vol. 17, Nature America Inc., New York, NY, USA.

Christians, F. et al., "Directed evolution of thymidine kinase for AZT phosphorylation using DNA family shuffling," Nature Biotechnology, Mar. 1999, pp. 259-264, vol. 17, Nature America Inc., New York, NY, USA.

Cirino et al. "Screening for thermostability." Methods in Molecular Biology, May 2003, pp. 117-125, vol. 230.

Cirino et al. "A self-sufficient peroxide-driven hydroxylation biocatalyst," Angewandte Chemie International Edition, 2003, vol. 42, No. 28, pp. 3299-3301.

Cirino et al., "Exploring the diversity of heme enzymes through directed evolution," In Directed Molecular Evolution of Proteins, 2002, pp. 215-243, S. Brakmann and K. Johnsson, eds., (Germany: Wiley-VCH).

Cleland, J. et al., "Cosolvent Assisted Protein Refolding," Biotechnology, Dec. 1990, pp. 1274-1278, vol. 8.

Coco et al., Nat. Biotechnol., 2001, vol. 19, pp. 354-359.

Crameri, A. et al., "Molecular evolution of an arsenate detoxification pathway by DNA shuffling," *Nature Biotechnology*, May 1997, pp. 436-438, vol. 15, Nature America Inc., New York, NY, USA.

Crameri, A. et al., "Improved Green Fluorescent Protein by Molecular Evolution Using DNA Shuffling," *Nature Biotechnology*, Mar. 1996, pp. 315-319, vol. 14, Nature America Inc., New York, NY, USA.

Crameri, A. et al., "Construction and evolution of antibody-phage libraries by DNA shuffling," *Nature Medicine*, Jan. 1996, pp. 100-106, vol. 2, No. 1.

Crameri et al., "DNA shuffling of a family of genes from diverse species accelerates directed evolution," Nature, 1998, vol. 391, pp. 288-291.

Cui et al., "Recombinatoric exploration of novel folded structures: a heteropolymer-based model of protein evolutionary landscapes," Proc Natl Acad Sci USA, 2002, vol. 99, pp. 809-814.

Dahlhoff, W. et al., "L-Glucose or D-*gluco*-Hexadialdose from D-Glucurono-6,3-lactone by Controlled Reductions," *Angew. Chem. Int. Ed. Engl.*, 1980, pp. 546-547, 19 No. 7, Verlag Chemie, GmbH, Weinheim, Germany.

Danon, A., et al. "Enrichment of Rat Tissue Lipids with Fatty Acids that are Prostaglandin Precursors" *Biochimica et Biophysica Acta*, 1975, 388: 318-330.

De Bernardez-Clark, E. et al., "Inclusion Bodies and Recovery of Proteins from the Aggregated State," *ACS Symposium Series Protein Refolding, 199th Natl Mtg American Chemical Society*, Apr. 22-27, 1990, pp. 1-20, American Chemical Society, Washington, DC, USA.

De Visser et al., "Hydrogen bonding modulates the selectivity of enzymatic oxidation by P450: Chameleon oxidant behavior by compound I," Angewandte Chemie-International Edition, 2002, vol. 41, No. 11, pp. 1947-+.

De Visser et al., "What factors affect the regioselectivity of oxidation by cytochrome P450? A DFT study of allylic hydroxylation and double bond epoxidation in a model reaction," Journal of the American Chemical Society, 2002, vol. 124, No. 39, pp. 11809-11826.

Deacon, S. et al., "Enhanced Fructose Oxidase Activity in a Galactose Oxidase Variant," *ChemBioChem: A European Journal of Chemical Biology*, 2004, pp. 971-979, 5, Wiley-VCH Verlag GmbH & Co., Weinheim, Germany.

Delagrave, S. et al., "Recursive ensemble mutagenesis," *Protein Engineering*, Apr. 1993, pp. 327-331, vol. 6, No. 3, Oxford University Press.

Delagrave, S. et al., "Searching Sequence Space to Engineer Proteins: Exponential Ensemble Mutagenesis," *Bio/Technology*, Dec. 1993, pp. 1548-1552, vol. 11, American Society for Cell Biology, New Orleans, LA, USA.

Dordick, J., "Designing Enzymes for Use in Organic Solvents," *Biotechnol. Prog.*, 1992, pp. 259-267, 8, American Chemical Society and American Institute of Chemical Engineers.

Dower, W. et al., "High efficiency transformation of *E. coli* by high voltage electroporation," *Nucleic Acids Research*, 1988, pp. 6127-6145, vol. 16, No. 13, IRL Press Limited, Oxford, England.

Elliot et al., "Regio- and stereoselectivity of particulate methane monoxygenanse from *Methylococcus capsulates* (Bath)," Journal of the American Chemical Society, 1997, vol. 199, No. 42, pp. 9949-9955.

Fiedler, K., et al., The Role of N-Glycans in the Secretory Pathway, *Cell*, May 5, 1995, pp. 309-312, vol. 81, Cell Press.

Fisher, M., et al., "Positional Specificity of Rabbit CYP4B1 for ω-Hydroxylation of Short-Medium Chain Fatty Acids and Hydrocarbons," *Biochemical and Biophysical Research Communications*, 1998, pp. 352-355, vol. 248, No. RC988842.

Fox, B., et al., "Methane Monooxygenase from *Methylosinus trichosporium* OB3b," *Methods in Enzymology*, 1990, pp. 191-202, vol. 188, Academic Press, Inc.

Fox, B., et al., "Methane Monooxygenase from *Methylosinus trichosporium* OB3b Purification and Properties of a Three-Component System with High Specific Activity from a Type II Methanotroph," *The Journal of Biological Chemistry*, Jun. 15, 1989, pp. 10023-10033, vol. 264, No. 17, The American Society for Biochemistry and Molecular Biology, Inc.

Fruetel, J., et al., "Relationship of Active Site Topology to Substrate Specificity for Cytochrome P450$_{terp}$ (CYP108)," *The Journal of Biological Chemistry*, Nov. 18, 1994, pp. 28815-28821, vol. 269, No. 46, The American Society for Biochemistry and Molecular Biology, Inc.

Gahmberg C., et al., "Nonmetabolic Radiolabeling and Taggin of Glycoconjugates," *Methods in Enzymology*, 1994, pp. 32-44, vol. 230, Academic Press, Inc.

Gazaryan, I.G., "Heterologous Expression of Heme-Containing Peroxidases," *Plant Peroxidase Newsletter*, Sep. 1994, pp. 11-13, No. 4, LABPV Newsletters.

Gibbs et al., "Degenarate oligonucleotide gene shuffling (DOGS): a method for enhancing the frequency of recombination with family shuffling," Gene, 2001, vol. 271, pp. 13-20.

Gietz, R., et al., "Studies on the Transformation of Intact Yeast Cells by the LiAc/SS-DNA/PEG Procedure," *Yeast*, Apr. 15, 1995, pp. 355-360, vol. 11, No. 4, John Wiley & Sons Ltd.

Gillam, E., et al., "Expression of Cytochrome P450 2D6 in *Escherichia coli*, Purification, and Spectral and Catalytic Characterization," *Archives of Biochemistry and Biophysics*, Jun. 1, 1995, pp. 540-550, vol. 319, No. 2, Academic Press, Inc.

Giver, L., et al., "Combinatorial Protein Design by In Vitro Recombination," *Current Opinion in Chemical Biology*, 1998, pp. 335-338, vol. 2, Current Biology Ltd.

Giver, L., et al., "Directed Evolution of a Thermostable Esterase," *Proc. Natl. Acad. Sci. USA*, Oct. 1998, pp. 12809-12813, vol. 95.

Gleider et al., "High-throughput screens based on NAD(P)H depletion," Directed Enzyme Evolution: Screening and Selection Methods, 2003, vol. 230.

Gleider et al., "Laboratory evolution of a soluble, self-sufficient, highly active alkane hydroxylase," Nature Biotech., 2002, vol. 20, pp. 1135-1139.

Goldman, E., et al., "An Algorithmically Optimized Combinatorial Library Screened by Digital Imaging Spectroscopy," *Biotechnology*, Dec. 1992, pp. 1557-1561, vol. 10.

Gonzalez et al., "Evolution of the P450 gene superfamily animal-plant 'warfare', molecular drive and human genetic differences in drug oxidation," Trends Genet. 1990, vol. 6, pp. 182-186.

Gotoh, Cytochrome P450, 2nd Edition, 1993, pp. 255-272.

Gram, H., et al., "In Vitro Selection and Affinity Maturation of Antibodies from a Naive Combinatorial Immunoglobulin Library," *Proc. Natl. Acad. Sci. USA*, Apr. 1992, pp. 3576-3580, vol. 89.

Green, J., et al., "Substrate Specificity of Soluble Methane Monooxygenase Mechanistic Implications," *The Journal of Biological Chemistry*, Oct. 25, 1989, pp. 17698-17703, vol. 264, No. 30, The American Society for Biochemistry and Molecular Biology, Inc.

Griebenow, K., et al., Lyophilization-Induced Reversible Changes in the Secondary Structure of Proteins, *Proc. Natl. Acad. Sci. USA*, Nov. 1995, pp. 10969-10976, vol. 92.

Guengerich, F., et al., "Purification of Functional Recombinant P450s from Bacteria," *Methods in Enzymology*, 1996, pp. 35-44, vol. 272, Academic Press, Inc.

Güssow, D., et al., "Direct Clone Characterization from Plaques and Colonies by the Polymerase Chain Reaction," *Nucleic Acids Research*, 1989, p. 4000, vol. 17, No. 10, IRL Press.

Hamilton, G.A., et al., "Galactose Oxidase: The Complexities of a Simple Enzyme," *Oxidases and Related Redox Systems*, 1973, pp. 103-124, vol. 1, University Park Press.

Hamilton, G.A., et al., "Trivalent Copper, Superoxide, and Galactose Oxidase," *Journal of the American Chemical Society*, Mar. 15, 1978, pp. 1899-1912, vol. 100, No. 6, American Chemical Society.

Hansson et al., J. Mol. Biol., 1999, vol. 287, pp. 265-276.

Hartmann, M., et al., "Selective Oxidations of Linear Alkanes with Molecular Oxygen on Molecular Sieve Catalysts—A Breakthrough?," *Agnew. Chem. Int. Ed. 2000*, pp. 888-890, vol. 39, No. 5.

Haschke, R., et al., "Calcium-Related Properties of Horseradish Peroxidase," *Biochemical and Biophysical Research Communiactions*, Feb. 28, 1978, pp. 1039-1042, vol. 80, No. 4, Academic Press, Inc.

Helenius, A., "How N-linked Oligosaccharides Affect Glycoprotein Folding in the Endoplasmic Reticulum," *Molecular Biology of the Cell*, Mar. 1994, pp. 253-265, vol. 5, No. 3, The American Society for Cell Biology.

Hermes, J., et al., "Searching Sequence Space by Definably Random Mutagenesis: Improving the Catalytic Potency of an Enzyme," *Proc. Natl. Acad. Sci. USA*, Jan. 1990, pp. 696-700, vol. 87.

Hiraga et al., "General method for sequence-independent site-directed chimeragenesis," J. Mol. Biol. 2003, vol. 330, pp. 287-296.
Hopps, H.B., "Purpaid: a reagent that turns aldehydes purple," Aldrichim. Acta. 2000, vol. 33, pp. 28-30.
Horton, et al., "Engineering hybrid genes with the use of restriction enzymes: gene splicing by overlap extention," Gene, 1989, vol. 77, pp. 61-68.
Ito, N. et al., "X-Ray Crystallographic Studies of Cofactors in Galactose Oxidase," Methods in Enzymology, Redox-Active Amino Acids in Biology, 1995, pp. 235-262, vol. 258, Academic Press, Inc.
Ito, N. et al., "Crystal Structure of a Free Radical Enzyme, Galactose Oxidase," Journal of Molecular Biology, 1994, pp. 794-814, vol. 238, No. 5, Academic Press Limited.
Ito, N. et al., "Novel thioether bond revealed by a 1.7 Å crystal structure of galactose oxidase," Nature, Mar. 7, 1991, pp. 87-90.
Jaeger et al., "Enantioselective biocatalysts optimized by directed evolution," Current Opinion in Biotechnology, 2004, vol. 15, No. 4, pp. 305-313.
Khoslat, C. et al., "Expression of Intracellular Hemoglobin Improves Protein Synthesis in Oxygen-Limited Escherichia coli," Bio/Technology, Sep. 1990, pp. 849-853, American Society for Cell Biology, New Orleans, LA, USA.
Kiba, N. et al., "Post-column co-immobilized galactose oxidase/peroxidase reactor for fluorometric detection of saccharides in a liquid chromatographic system," Journal of Chromatography, 1989, pp. 183-187, vol. 463, Elsevier Science Publishes B.V., Amsterdam, The Netherlands.
Kim, J. et al., "Use of 4-(Nitrobenzyl)Pyridine (4-NBP) To Test Mutagenic Potential of Slow-Reacting Epoxides, Their Corresponding Olefins, and Other Alkylating Agents," Bull. Environ. Contam. Toxicol., 1992, pp. 879-885, vol. 49, Springer-Verlag New York Inc.
Klibanov, A. et al., "Stereospecific Oxidation of Aliphatic Alcohols Catalyzed by Galactose Oxidase," Biochemical and Biophysical Research Communications, 1982, pp. 804-808, vol. 108, No. 2, Academic Press, Inc.
Knappik, A. et al., "Engineered turns of a recombinant antibody improves its in vivo folding," Protein Engineering, Jan. 1995, pp. 81-89, vol. 8, No. 1, Oxford University Press.
Koroleva, O. et al., "Properties of Fusarium graminearum Galactose Oxidase," 1984, pp. 500-509, Plenum Publishing Corporation.
Kosman, D., "Chapter 1 Galactose Oxidase," in Lontie, R., Eds., Copper Proteins and Copper Enzymes vol. II, pp. 1-26, CRC Press, Inc., Boca Raton, FL, USA, 1984.
Koster, R. et al., "Organoboron Monosaccharides; XII[1]. Quantitative Preparation of D-gluco- Hexodialdose from Sodium D-Glucuronate or D-Glucuronic acid," Synthesis, Aug. 1982, pp. 650-652, No. 8, Georg Thieme Verlag.
Kuchner, O. et al., "Directed evolution of enzyme catalysts," Biotechnology, Dec. 1997, pp. 523-530, vol. 15, Elsevier Science Ltd.
Kuhn-Velten, W., "Effects of Compatible Solutes on Mammalian Cytochrome P450 Stability," 1997, pp. 132-135, Verlag der Zeitschrift für Naturforschung.
Kvittingen, L. et al., "Use of Salt Hydrates to Buffer Optimal Water Level During Lipase Catalysed Synthesis in Organic Media: A Practical Procedure for Organic Chemists," Tetrahedron, 1992, pp. 2793-2802, vol. 48, No. 13, Pergamon Press Ltd., Great Britain.
Lei, S. et al., "Characterization of the Erwinia carotovora pelB Gene and Its Product Pectate Lyase," Journal of Bacteriology, Sep. 1987, pp. 4379-4383, vol. 169, No. 9, American Society for Microbiology.
Leadbetter, E. R., et al. "Incorporation of Molecular Oxygen in Bacterial Cells Utilizing Hydrocarbons for Growth" Natures; Oct. 31, 1959; vol. 184, pp. 1428-1429.
Leung, D. et al., "A Method for Random Mutagenesis of a Defined DNA Segment Using a Modified Polymerase Chain Reaction," Technique, A Journal of Methods in Cell and Molecular Biology, Aug. 1989, pp. 11-15, vol. 1, No. 1, Saunders Scientific Publications.
Lewis, D., "P450 Substrate Specificity and Metabolism," Cytochromes P450: Structure, Function and Mechanism, Aug. 2001, pp. 115-166, Taylor & Francis Publishers.
Li et al., "Engineering cytochrome P450 BM-3 for oxidation of polycyclic aromatic hydrocarbons," Appl. and Env. Microbiol., Dec. 2001, 67(10):5735-5739.

Li, Q. et al., "Rational evolution of a medium chain-specific cytochrome P-450 BM-3 variant," Biochimica et Biophysica Acta, 2001, pp. 114-121, 1545, Elsevier Science B.V.
Li et al., Chemistry 2000, vol. 6, pp. 1531-1536.
Li et al., "residue size at position 87 of cytochrome P450 BM-3 determines its stereo selectivity in propylbenzene and 3-chlorostyrene oxidation," FEBS Lett 508, 2001, pp. 249-252.
Lis, M. et al., "Galactose Oxidase-Glucan Binding Domain Fusion Proteins as Targeting Inhibitors of Dental Plaque Bacteria," Antimicrobial Agents & Chemotherapy, May 1997, pp. 999-1003, vol. 41, No. 5, American Society for Microbiology.
Liu, C. et al., "Sugar-containing Polyamines Prepared Using Galactose Oxidase Coupled with Chemical Reduction," J. Am. Chem. Soc., Jan. 20, 1999, pp. 466-467, vol. 121, No. 2, American Chemical Society.
Lutz et al., Proc. Natl Acad Sci USA, 2001. vol. 98, pp. 11248-11253.
Mannino, S. et al., "Simultaneous Determination of Glucose and Galactose in Dairy Products by Two Parallel Amperometric Biosensors," Italian Journal of Food Science, 1999, pp. 57-65, vol. 11, No. 1, Chiriotti Editori, s.p.a., Pinerolo, Italy.
Maradufu, A. et al., "A Non-Hydrogen-Bonding Role for the 4-Hydroxyl Group of D-Galactose in its Reaction with D-Galactose Oxidase," Carbohydrate Research, 1974, pp. 93-99, 32, Elsevier Scientific Publishing Company, Amsterdam, The Netherlands.
Maradufu, A. et al., "Stereochemistry of Dehydrogenation by D-Galactose Oxidase," Canadian Journal of Chemistry, Oct. 1971, pp. 3429-3437, vol. 49, No. 19, NCR Research Press, Ottawa, Canada.
March, J., Advanced Organic Chemistry: Reactions, Mechanisms, and Structure, 4th Edition, 1992, pp. 882-884, Wiley and Sons, NY.
March, J., Advanced Organic Chemistry: Reactions, Mechanisms, and Structure, 4th Edition, 1992, pp. 1072-1074, Wiley and Sons, NY.
Martin, B. et al., "Highly swelling hydrogels from ordered galactose-based polyacrylates," Biomaterials, 1998, pp. 69-76, 19(1-3), Elsevier.
Martin, I. et al., "Detection of honey adulteration with beet sugar using stable isotope methodology," Food Chemistry, 1998, pp. 281-286, vol. 61, No. 3, Elsevier Science Ltd.
Martineau, P. et al., "Expression of an Antibody Fragment at High Levels in the Bacterial Cytoplasm," J. Mol. Biol., 1998, pp. 117-127, vol. 280, No. 1, Academic Press.
Martinez, C. et al., "Cytochrome P450's: Potential Catalysts for Asymmetric Olefin Epoxidations," Current Organic Chemistry, 2000, pp. 263-282, vol. 4, No. 3, Bentham Science Publishers B.V.
Matson, R. et al., "Characteristics of a Cytochrome P-450-Dependent Fatty Acid ω-2 Hydroxylase From Bacillus Megaterium," Biochimica et Biophysica Acta, 1977, pp. 487-494, 487, Elsevier/North Holland Biomedical Press.
Mauersberger et al., Z Alig. Mikrobiol., 1981, vol. 121, pp. 313-321.
Mazur, A., "Chapter 8, Galactose Oxidase," ACS Symposium Series 466—Enzymes in Carbohydrate Synthesis, 1991, pp. 99-110, American Chemical Society, Washington, DC, USA.
Mazur, A., et al., "Chemoenzymic Approaches to the Preparation of 5-C-(Hydroxymethyl)hexoses," J. Org. Chem., 1997, pp. 4471-4475, vol. 62, No. 13, American Chemical Society, Washington, DC, USA.
McPherson, M. et al., "Galactose oxidase of Dactylium dendroides. Gene cloning and sequence analysis," Chemical Abstract Service, XP-002298547, Database accession No. M86819, 2007.
McPerson, M. et al., "Galactose Oxidase of Dactylium dendroides," Apr. 1992, pp. 8146-8152, The Journal of Biological Chemistry, vol. 267, No. 12, The American Society for Biochemistry and Molecular Biology, Inc.
McPherson, M. et al., "Galactose oxidase: Molecular analysis and mutagenesis studies," Biochemical Society Transactions, 646th Meeting Leeds, 1993, pp. 1992-1994, vol. 21, The Biochemical Society, Portland Press.
Meinhold, P. et al. "Direct Conversions of Ethane to Ethanol by Engineered Cytochrome P450 BM3," ChemBioChem, 2005, pp. 1-4, vol. 6, Wiley-VCH Verlag GmbH & Co. Weinheim, Germany.
Mendonca, M. et al., "Purification and Characterization of Intracellular Galactose Oxidase from Dactylium dendroides," Archives of Biochemistry and Biophysics, Feb. 1987, pp. 507-514, vol. 252, No. 2, Academic Press, Inc.

Mendonca, M. et al., "Role of Carbohydrate Content on the Properties of Galactose Oxidase from *Dactylium dendroides*," *Archives of Biochemistry and Biophysics*, Nov. 1988, pp. 427-434, vol. 266, No. 2, Academic Press, Inc.

Meyer et al., "Library analysis of SCHEMA-guided protein recombination," *Prot. Sci.*, 2003, vol. 12, No. 8, pp. 1686-1693.

Miele, R., et al., "Glycosylation of Asparagine-28 of Recombinant Staphylokinase with High-Mannose-type Oligosaccharides Results in a Protein with Highly Attenuated Plasminogen Activator Activity," *Journal of Biological Chemistry*, Mar. 1999, pp. 7769-7776, vol. 274, No. 12, The American Society for Biochemistry and Molecular Biology, Inc.

Minshull, J. et al., "Protein evolution by molecular breeding," *Chemical Biology*, 1999, pp. 284-290, 3, Elsevier Science Ltd.

Mitraki, A. et al., "Amino acid substitiutions influencing intracellular protein folding pathways," *FEBS Letters*, Jul. 1992, pp. 20-25, vol. 307, No. 1, Elsevier Science Publishers B.V.

Miyazaki, K. et al., "Directed Evolution Study of Temperature Adaptation in a Psychrophilic Enzyme," *Journal Mol. Biol.*, 2000, pp. 1015-1026, 297, Academic Press.

Modi, S. et al., "NMR Studies of Substrates Binding to Cytochrome $P_{450\ BM3}$: Comparisons to Cytochrome $P_{450\ cam}$," *Biochemistry*, 1995, pp. 8982-8988, vol. 34, No. 28, American Chemical Society.

Moore, J. et al., "Directed evolution of a *para*-nitrobenzyl esterase for aqueous-organic solvents," *Nature Biotechnology*, Apr. 1996, pp. 458-467, vol. 14.

Moore, J. et al., "Strategies for the in vitro Evolution of Protein Function: Enzyme Evolution by Random Recombination of Improved Sequences," *J. Mol. Biol.*, 1997, pp. 336-347, 272, Academic Press Limited.

Munro, A. et al., "Alkane Metabolism by Cytochrome P450 BM3," *Biochemical Society Transactions*, 1993, p. 412S, 21.

Munro et al., "P450 BM3: The very model of a modern flavocyteochrome," TRENDS Biochem. Sci., 2002, vol. 27, pp. 250-257.

Murrell, J. et al., "Molecular biology and regulation of methane monooxygenase," *Arch. Microbiol.*, 2000, pp. 325-332, 173o.

Nagayama, Y. et al., "Role of Asparagine-linked Oligosaccharides in Protein Folding, Membrane Targeting, and Thyrotropin and Autoantibody Binding of the Human Thyrotropin Receptor," *Journal of Biological Chemistry*, Dec. 1998, pp. 33423-33428, vol. 273, No. 5, The American Society for Biochemistry and Molecular Biology, Inc.

Nakajima, H. et al., "Industrial Application of Adenosine 5'-Triphosphate Regeneration to Synthesis of Sugar Phosphates," ACS Symposium Series 466, Enzymes in Carbohydrates Synthesis, Chapter 9, pp. 110-120, American Chemical Society, Washington DC, 1991, Bednarski & Simon, Editors.

Ness, J. et al., "DNA shuffling of subgenomic sequences of subtilisin," *Nature Biotechnology*, Sep. 1999, pp. 893-896, vol. 17, No. 9, Nature Publishing Group.

Neylon, C., "Chemical and biochemical strategies for the randomization of protein encloding DNA sequences: library construction methods for directed evolution," Nucleic Acid Res., 2004, vol. 32, No. 4, pp. 1448-1459.

Ohkuma et al., "Cyp52 (Cytochrome-P450alk) multigene family in candida-maltose—Identification and characterization of 8 members," DNA and Cell Biology, 1995, vol. 14, No. 2, pp. 163-173.

Oliphant, A. et al., "Cloning of random-sequence oligodeoxynucleotides," *Gene*, 1986, pp. 177-183, 44, Elsevier Science Publishers B.V.

Oliver, C. et al., "Engineering the substrate specificity of *Bacillus megaterium* cytochrome P-450 BM3: hydroxylation of alkyl trimethylammonium compounds," *Biochem. J.*, 1997, pp. 537-544, 327, The Biochemical Society, London, England.

O'Maille et al., Structure-based combinatorial protein engineering (SCOPE), J. Mol. Biol., 2002, vol. 321, pp. 677-691.

Ortlepp, S. et al., "Expression and characterization of a protein specified by a synthetic horseradish peroxidase gene in *Escherichia coli*," *Journal of Biotechnology*, 1989, pp. 353-364, 11, Elsevier Science Publishers B.V.

Ostermeier, M. et al., "Incremental Truncation as a Strategy in the Engineering of Novel Biocatalysts," *Bioorganic & Medicinal Chemistry*, 1999, pp. 2139-2144, 7, Elsevier Science Ltd.

Otey et al., "Functional evolution and structural conservation in chimeric cytochromes P450: Calibrating a structure-guided approach," Chemistry and Biology, 2004, vol. 11, pp. 309-318.

Parekh, R. et al., "Multicopy Overexpression of Bovine Pancreatic Trypsin Inhibitor Saturates the Protein Folding and Secretory Capacity of *Saccharomyces cerevisiae*," *Protein Expression and Purification*, 1995, pp. 537-545, 6, Academic Press.

Patten, P. et al., "Applications of DNA shuffling to pharmaceuticals and vaccines," *Biotechnology*, 1997, pp. 724-733, vol. 8, Elsevier Science Ltd.

Peterson et al., "The many faces of P450s and their structural and functional implications," Sixth International Symposium on Cytrochrome P450 Biodiversity: University of California, Los Angeles, 2002.

Pompon, et al., "Protein engineering by cDNA recombination in yeasts: shuffling of mammalian cytochrome P-450 functions," Gene, 1989, vol. 83, pp. 15-24.

Porter, et al., J. Biol. Chem., 1991, vol. 266, pp. 13469-13472.

Ramarao et al., "Identification by in vitro mutagenesis of the interaction of two segments of C2MstC1, a chimera of cytochromes P450 2C2 and P450 2C1," The Journal of Biological Chemistry, Jan. 27, 1995, vol. 270, No. 4, pp. 1873-1880.

Rathore, D., et al., "Expression of Ribonucleolytic Toxin Restrictocin in *Escherichia coli*: Purification and Characterization," *FEBS Letters*, 1996, pp. 259-262, vol. 392, Federation of European Biochemical Societies.

Reynolds, M., et al., "Structure and Mechanism of Galactose Oxidase: Catalytic Role of Tyrosine 495," *JBIC*, 1997, pp. 327-335, vol. 2.

Rodriquez-Lopez, J., et al., "Role of Arginine 38 in Horseradish Peroxidase—A Critical Residue for Substrate Binding and Catalysis," *The Journal of Biological Chemistry*, Feb. 23, 1996, pp. 4023-4030, vol. 271, No. 8, The American Society for Biochemistry and Molecular Biology.

Ramanos, M., et al., "Foreign Gene Expression in Yeast: a Review," *Yeast*, Jun. 1992, pp. 423-488, vol. 8, No. 6, John Wiley & Sons Ltd.

Root, R., et al., "Enzymatic Synthesis of Unusual Sugars: Galactose Oxidase Catalyzed Stereospecific Oxidation of Polyols," *Journal of the American Chemical Society*, 1985, pp. 2997-2999, vol. 107, No. 10, American Chemical Society.

Said, I.T., et al., "Comparison of Different Techniques for Detection of Gal-GalNAc, an Early Marker of Colonic Neoplasia," *Histology and Histopathology*, Apr. 1999, pp. 351-357, vol. 14, No. 2, Jiménez Godoy, S.A.

Salazar et al., "Thermostabilization of a cytochrome P450 peroxygenase," Chembiochem, 4(9):891-893, Sep. 2003.

Savenkova, M., et al. et al. "Improvement of Peroxygenase Activity by Relocation of a Catalytic Histidine within the Active Site of Horseradish Peroxidase," *Biochemistry*, 1998, pp. 10828-10836, vol. 37, American Chemical Society.

Saysell, C., et al., "Properties of the Trp290His Variant of *Fusarium* NRRL 2903 Galactose Oxidase: Interactions of the $GOase_{semi}$ State with Different Buffers, Its Redox Activity and Ability to Bind Azide," *JBIC*, 1997, pp. 702-709, vol. 2.

Schatz, P., et al., "Genetic Analysis of Protein Export in *Escherichia coli*," *Annual Review of Genetics*, 1990, pp. 215-248, vol. 24, Annual Reviews, Inc., Palo Alto, CA.

Schein C., "Solubility as a Function of Protein Structure and Solvent Components," *Bio/Technology*, Apr. 1990, pp. 308-317, vol. 8, No 4.

Scheller, U., et al., "Characterization of the *n*-Alkane and Fatty Acid Hydroxylating Cytochrome P450 Forms 52A3 and 52A4," *Archives of Biochemistry and Biophysics*, Apr. 15, 1996, pp. 245-254, vol. 328, No. 2, Academic Press, Inc.

Schlegel, R., et al., "Substrate Specificity of D-Galactose Oxidase," *Carbohydrate Research*, Jun. 1968, pp. 193-199, vol. 7, No. 2, Elsevier Publishing Company, Amsterdam.

Schmid, A., et al., "Industrial Biocatalysis Today and Tomorrow," *Nature*, Jan. 11, 2001, pp. 258-268, vol. 409, Macmillian Magazines Ltd.

Schneider, S., et al., "Controlled Regioelectivity of Fatty Acid Oxidation by Whole Cells Producing Cytochrome P450$_{BM-3}$ Monooxygenase Under Varied Dissolved Oxygen Concentrations," *Biotechnology and Bioengineering*, Aug. 5, 1999, pp. 333-341, vol. 64, No. 3, John Wiley & Sons, Inc.

Schneider, et al., "Production of chiral hydroxyl long chain fatty acids by whole cells producing cytochrome P450 (BM-3) monoxygenase," Tetrahedron Asymetry, 1998, vol. 9, No. 16, pp. 2833-2844.

Seghezzi et al., "Identification of characterization of additional members of the cytochrome-P450 multigene family Cyp52 of candidatropicalis," DNA and Cell Biology, 1992, vol. 11, No. 10, pp. 767-780.

Shafikhani, S., et al., "The Generation of Large Libraries of Random Mutants in *Bacillus subtilis* by PCR-Based Plasmid Multimerization," *BioTechniques*, Aug. 1997, pp. 304-310, vol. 23, No. 2.

Shanklin, J., et al., "Moössbauer Studies of Alkane ω-Hydroxylase: Evidence for a Diiron Cluster in an Integral-Membrane Enzyme," *Proc. Natl. Acad. Sci. USA*, Apr. 1997, pp. 2981-2986, vol. 94.

Shao, Z., et al., "Random-priming In Vitro Recombination: An Effective Tool for Directed Evolution," *Nucleic Acids Research*, Jan. 15, 1998, pp. 681-683, vol. 26, No. 2, Oxford University Press.

Shindler, J., et al., "Peroxidase from Human Cervical Mucus—The Isolation and Characterisation," *European Journal of Biochemistry*, Jun. 1976, pp. 325-331, vol. 65, No. 2.

Sieber et al., Nat. Biotechnol., 2001, vol. 19, pp. 456-460.

Sirotkin, K., "Advantages to Mutagenesis Techniques Generating Populations Containing the Complete Spectrum of single Codon Changes," *J. Theor. Biol.*, 1986, pp. 261-279, vol. 123, Academic Press Inc. (London) Ltd.

Smith, A., et al., "Expression of a Synthetic Gene for Horseradish Peroxidase C in *Escherichia coli* and Folding and Activation of the Recombinant Enzyme with $Ca^{2+}$ and Heme," *The Journal of Biological Chemistry*, Aug. 5, 1990, pp. 13335-13343, vol. 265, No. 22, The American Society for Biochemistry and Molecular Biology.

Smith, A., et al., "Substrate Binding Catalysis in Heme Peroxidases," *Current Opinion in Chemical Biology*, (1998), pp. 269-278, vol. 2.

Sono et al., "Heme-containing oxygenases," Chemical Reviews, 1996, vol. 96, No. 7, pp. 2841-2887.

Spiro, T., et al., "Is the CO Adduct of Myoglobin Bent, and Does It Matter?," *Accounts of Chemical Research*, 2001, pp. 137-144, vol. 34, No. 2, American Chemical Society.

Staijen, I., et al., "Expression, Stability and Performance of the Three-Component Alkane Mono-oxygenase of *Pseudomonas oleovorans* in *Escherichia coli*," *Eur. J. Biochem.*, 2000, pp. 1957-1965, vol. 267.

Stemmer, W., "DNA Shuffling by Random Fragmentation and Reassembly: In Vitro Recombination for Molecular Evolution," *Proc. Natl. Acad. Sci. USA*, Oct. 25, 1994, pp. 10747-10751, vol. 91, No. 22.

Stemmer, W., "Rapid Evolution of a Protein In Vitro by DNA Shuffling," *Nature*, Aug. 4, 1994, pp. 389-391, vol. 370, No. 6488.

Stemmer, W., et al., "Selection of an Active Single Chain Fv Antibody from a Protein Linker Library Prepared by Enzymatic Inverse PCR," *BioTechniques*, 1993, pp. 256-265, vol. 14, No. 2.

Stevenson, J., et al., "The Catalytic Oxidation of Linear and Branched Alkanes by Cytochrome P450$_{cam}$," *J. Am. Chem. Soc.*, 1996, pp. 12846-12847, vol. 118, No. 50, American Chemical Society.

Studier, F., et al., "Use of T7 RNA Polymerase to Direct Expression of Cloned Genes," *Methods in Enzymology*, 1990, pp. 60-89, vol. 185, Academic Press, Inc.

Sun, L., et al., "Expression and Stabilization of Galactose Oxidase in *Escherichia coli* by Directed Evolution," *Protein Engineering*, Sep. 2001, pp. 699-704, vol. 14, No. 9, Oxford University Press.

Sun, L., et al., "Modification of Galactose Oxidase to Introduce Glucose 6-Oxidase Activity," *ChemBioChem: A European Journal of Chemical Biology*, Aug. 2, 2002, pp. 781-783, vol. 3, No. 8, Wiley-VCH-Vertag GmbH, Weinheim, Germany.

Szabó, E., et al., "Application of Biosensor for Monitoring Galactose Content," *Biosensors & Bioelectronics*, 1996, pp. 1051-1058, vol. 11, No. 10, Elsevier Science Limited.

Taly et al., "A combinatorial approach to substrate discrimination in the P450 CYP1A subfamily," Biochimica et Biophysica Acta, 2007, vol. 1770, pp. 446-457.

Tams, J., et al., "Glycosylation and Thermodynamic Versus Kinetic Stability of Horseradish Peroxidase," *FEBS Letters*, 1998, pp. 234-236, vol. 421, Federation of European Biochemical Societies.

Thatcher, D., et al., "Protein Folding in Biotechnology," *Mechanisms of Protein Folding*, 1994, pp. 229-261, IRL Press, Oxford.

Tkac, J., et al., "Rapid and Sensitive Galactose Oxidase-Peroxidase Biosensor for Galactose Detection with Prolonged Stability," *Biotechnology Techniques*, 1999, pp. 931-936, Kluwer Academic Publishers.

Tonge, G., et al., "Purification and Properties of the Methane Monooxygenase enzyme System from *Methylosinus trichosporium* OB3b," *Biochem. J.*, 1977, pp. 333-344, vol. 161.

Tressel, P., et al., "A Simplified Purification Procedure for Galactose Oxidase," *Analytical Biochemistry*, Jun. 1980, pp. 150-153, vol. 105, No. 1, Academic Press, Inc.

Tressel, P., et al., "Galactose Oxidase from *Dactylium dendroides*," *Methods in Enzymology*, 1982, pp. 163-171, vol. 89, Academic Press.

Truan, G., et al., "Thr268 in Substrate Binding and Catalysis in P450BM-3," *Archives of iochemistry and Biophysics*, Jan. 1, 1998, pp. 53-64, vol. 349, No. 1, Academic Press.

Tsotsou et al., "High throughput assay for chytochroms P450BM3 for screening libraries of substrates and combinatorial mutants," Biosensors and Bioelectronics, 2002, vol. 17, No. 1-2, pp. 119-131.

Urlacher et al., "Biotransformations using prokaryotic P450 monooxygenases," Current Opinion in Biotechnology, 2002, vol. 13, pp. 557-564.

Urlacher et al., "Protein Engineering of cytochrome P450 monooxygenase from *Bacillus megaterium*." Methods in Enzymology, pp. 208-224, vol. 388, 2004.

Vega, F., et al., "On-line Monitoring of Galactoside Conjugates and Glycerol by Flow Injection Analysis," *Analytica Chimica Acta*, 1998, pp. 57-62, vol. 373, Elsevier Science B.V.

Voight et al., "Protein building blocks preserved by recombination," Nat. Struct. Biol., 2002, vol. 9, pp. 553-558.00.

Volkov et al., "Recombination and chimeragenesis by in vitro heteroduplex formation and in vivo repair," Nucleic Acids Res., 1999, vol. 27, e18.

Vrbová, E., et al., "Preparation and Utilization of a Biosensor Based on Galactose Oxidase," *Collect. Czech. Chem. Commun.*, 1992, pp. 2287-2294, vol. 57.

Wachter, R., et al., "Molecular Modeling Studies on Oxidation of Hexopyranoses by Galactose Oxidase. An Active Site Topology Apparently Designed to Catalyzed Radical Reactions, Either Concerted or Stepwise," *Journal of the American Chemical Society*, Mar. 9, 1996, pp. 2782-2789, vol. 118, No. 9.

Watkinson, R., et al., "Physiology of Aliphatic Hydrocarbon-Degrading Microorganisms," *Biodegradation*, 1990, pp. 79-92, vol. 1, Nos. 2/3, Kluwer Academic Publishers.

Welinder, K., "Amino Acid Sequence Studies of Horseradish Peroxidase," *European Journal of Biochemistry*, 1979, pp. 483-502.

Welinder, K., "Supplement to Amino Acid Sequence Studies of Horseradish Peroxidase," pp. 495-502, 1979.

Wetzel, R., et al., "Mutations in Human Interferon Gamma Affecting Inclusion Body Formation Identified by a General Immunochemical Screen," *Bio/Technology*, Aug. 1991, pp. 731-737, vol. 9.

Whittaker, M., et al., "The Active Site of Galactose Oxidase," *The Journal of Biological Chemistry*, 1988, pp. 6074-6080, vol. 263, No. 13, The American Society for Biochemistry and Molecular Biology, Inc.

Whitakker, M., et al., "Kinetic Isotope Effects as probes of the Mechanism of Galactose Oxidase," *Biochemistry*, 1998, pp. 8426-8436, vol. 37, American Chemical Society.

Wilkinson, D., et al., "Structural and Kinetic Studies of a Series of Mutants of Galactose Oxidase Identified by Directed Evolution," *Protein Engineering, Design & Selection*, Jan. 12, 2004, pp. 141-148, vol. 17, No. 2, Oxford University Press.

Wubbolts, et al., "Enantioselective oxidation by non-heme iron monoxygenases from Pseudomonas," CHIMIA, 1996, vol. 16, pp. 258-261.

Yang, G., et al., "Gal-GalNAc: A biomarker of Colon Carcinogenesis," *Histology and Histopathology*, 1996, pp. 801-806, vol. 11.

Yano, T., et al., "Directed Evolution of an Aspartate Aminotransferase with New Substrate Specificities," *Proc. Natl. Acad. Sci. USA*, May 1998, pp. 5511-5515, vol. 95.

Yeom, H., et al., "Oxygen Activation by Cytochrome $P450_{BM-3}$: Effects of Mutating an Active Site Acidic Residue," *Archieves of Biochemistry and Biophysics*, Jan. 15, 1997, pp. 209-216, vol. 337, No. 2, Academic Press.

You, L., et al., "Directed Evolution of Subtilisin E in *Bacillus subtilis* to Enhance Total Activity in Aqueous Dimethylformamide," *Protein Engineering*, 1996, pp. 77-83, vol. 9, Oxford University Press.

Zhang, J., et al., "Directed Evolution of a Fucosidase from a Galactosidase by DNA Shuffling and Screening," *Proc. Natl. Acad. Sci. USA*, Apr. 1997, pp. 4504-4509, vol. 94.

Zhang, T., et al., "Circular Permutation of T4 Lysozyme," *Biochemistry*, 1993, pp. 12311-12318, vol. 32, No. 46, American Chemical Society.

Zhao, H., et al., "Directed Evolution Converts Subtilisin E into a Functional Equivalent of Thermitase," *Protein Engineering*, 1999, pp. 47-53, vol. 12, No. 1, Oxford University Press.

Zhao, H., et al., "Molecular Evolution by Staggered Extension Process (StEP) In Vitro Recombination," *Nature Biotechnology*, Mar. 1998, pp. 258-261, vol. 16.

Zhao, H., et al., "Optimization of DNA Shuffling for High Fidelity Recombination," *Nucleic Acids Research*, 1997, pp. 1307-1308, vol. 25, No. 6, Oxford University Press.

Zimmer, T., et al., "The CYP52 Multigene Family of *Candida maltosa* Encodes Functionally Diverse *n*-Alkane-Inducible Cytochromes P450," *Biochemical and Biophysical Research Communications*, 1996, pp. 784-789, vol. 224, No. 3, Academic Press, Inc.

XP-002298548, "Protein Sequence," Database accession No. 355884-87-6, 2004.

"Enzymology of cytochrme P450 reductase," printed Apr. 5, 2004 http;//www/uky.edu/Pharmacy/ps/porter/CPR_enzymology.htm.

* cited by examiner

```
   1 agatctttat gaagacatag ctgcagaaga aaaagcaaga gctacatatc aatggttaat
  61 tgatatatca gatgatcccg atttaaacga cagcttacga tttttacgag aaagagagat
 121 tgttcactca cagcggttcc gcgaggccgt ggagatttta aaagatgaca gagacaggaa
 181 gaaaatcttt taactagtaa aaaaacatcc cccttggcga atgcaaacga aaggagggat
 241 gttttttgtt gtgactgcgt tgattatgcg ctagaactgc agtgacaaga aacaaccttt
 301 aatttccctt caacatcttt ccaaactcgc gtataactgt attcacctcc aatagattca
 361 ccggttgcca gtgcccatt taacgctact tttgtaacgg taacggcaag ttcttgaaac
 421 agtttaactt cttgttccaa cacttccatg cccgctatat caagactttt tgaacgatga
 481 acatttatat cttcttcttt tgacaaccat tgcccaaggt gattcacaaa aataagctca
 541 tctgaaagta attcttctaa tagctctatg ttattagaaa gcatggctga gcgaagcatt
 601 tcttcgtatt ctataactct tgcttgattc attttaatc ctcctttacg ccttgtgtaa
 661 ctcttttcta tttccacgtt gcttttcctt taaacttctt tcattaataa ttcgtgctaa
 721 attatgttaa tagaggggat aagtggacta attttctgta agcactaaat attctgaaat
 781 actctgttaa ttacctttaa atggtataaa attagaatga aagaaccttt tctttccact
 841 tttctagtta tcttttttact attaagatgc agttttttat acttgtaatt gtagcggaat
 901 gaacgttcat tccgttttg aaaagaggtg ataaagtgga atctactcca acaaaacaaa
 961 aagcgatttt ttctgcttcg cttctgctgt tgcagaaag agggtttgat gcaaccacga
1021 tgccaatgat tgcagagaat gccaaagtag gagcaggaac aatttatcgc tactttaaaa
1081 ataaagaaag ccttgtaaat gaattattcc aacagcacgt aaacgagttt ttacagtgca
1141 ttgaaagcgg tctggcaaac gagagagatg gataccgaga tgggtttcat catatctttg
1201 aaggtatggt gacatttact aaaaaccatc ctcgtgctct tggatttatt aaaactcata
1261 gccaaggaac ttttttaaca gaagagagcc gcttagcata tcaaaagctg gtggaatttg
1321 tttgtacgtt cttcagagaa ggacaaaagc aaggtgtgat tagaaatctt cctgaaaatg
1381 cgctaattgc tatttttatt ggaagtttca tggaagtata tgaaatgatt gaaaatgact
1441 acttatcttt aactgatgaa cttcttaccg gtgtagaaga gagtctgtgg gcagcactta
1501 gcagacaatc atgaaactta acaagtgaaa gagggataac atgacaatta aagaaatgcc
1561 tcagccaaaa acgtttggag agcttaaaaa tttaccgtta ttaaacacag ataaaccggt
1621 tcaagctttg atgaaaattg cggatgaatt aggagaaatc tttaaattcg aggcgcctgg
1681 tcgtgtaacg cgctacttat caagtcagcg tctaattaaa gaagcatgcg atgaatcacg
1741 ctttgataaa acttaagtc aagcgcttaa atttgtacgt gattttgcag gagacgggtt
1801 atttacaagc tggacgcatg aaaaaaattg gaaaaaagcg cataatatct tacttccaag
1861 cttcagtcag caggcaatga aaggctatca tgcgatgatg gtcgatatcg ccgtgcagct
1921 tgttcaaaag tgggagcgtc taaatgcaga tgagcatatt gaagtaccgg aagacatgac
1981 acgtttaacg cttgatacaa ttggtctttg cggctttaac tatcgcttta acagctttta
2041 ccgagatcag cctcatccat ttattacaag tatggtccgt gcactggatg aagcaatgaa
2101 caagctgcag cgagcaaatc cagacgaccc agcttatgat gaaaacaagc gccagtttca
2161 agaagatatc aaggtgatga cgacctagt agataaaatt attgcagatc gcaaagcaag
2221 cggtgaacaa agcgatgatt tattaacgca tatgctaaac ggaaaagatc cagaaacggg
2281 tgagccgctt gatgacgaga acattcgcta tcaaattatt acattcttaa ttgcgggaca
2341 cgaaacaaca agtggtcttt tatcatttgc gctgtatttc ttagtgaaaa atccacatgt
2401 attacaaaaa gcagcagaag aagcagcacg agttctagta gatcctgttc caagctacaa
2461 acaagtcaaa cagcttaaat atgtcggcat ggtcttaaac gaagcgctgc gcttatggcc
2521 aactgctcct gcgttttccc tatatgcaaa agaagatacg gtgcttggag gagaatatcc
2581 tttagaaaaa ggcgacgaac taatggttct gattcctcag cttcaccgtg ataaaacaat
2641 ttggggagac gatgtggaag agttccgtcc agagcgtttt gaaaatccaa gtgcgattcc
2701 gcagcatgcg tttaaaccgt tggaaacgg tcagcgtgcg tgtatcggtc agcagttcgc
2761 tcttcatgaa gcaacgctgg tacttggtat gatgctaaaa cactttgact tgaagatca
2821 tacaaactac gagctggata ttaaagaaac tttaacgtta aaacctgaag gctttgtggt
2881 aaaagcaaaa tcgaaaaaaa tccgcttgg cggtattcct tcacctagca ctgaacagtc
2941 tgctaaaaaa gtacgcaaaa aggcagaaaa cgctcataat acgccgctgc ttgtgctata
3001 cggttcaaat atgggaacag ctgaaggaac ggcgcgtgat tagcagata ttgcaatgag
3061 caaaggattt gcaccgcagg tcgcaacgct tgattcacac gccggaaatc ttccgcgcga
```

FIGURE 1A

```
3181 atttgtcgac tggttagacc aagcgtctgc tgatgaagta aaaggcgttc gctactccgt
3241 atttggatgc ggcgataaaa actgggctac tacgtatcaa aaagtgcctg cttttatcga
3301 tgaaacgctt gccgctaaag gggcagaaaa catcgctgac cgcggtgaag cagatgcaag
3361 cgacgacttt gaaggcacat atgaagaatg gcgtgaacat atgtggagtg acgtagcagc
3421 ctactttaac ctcgacattg aaaacagtga agataataaa tctactcttt cacttcaatt
3481 tgtcgacagc gccgcggata tgccgcttgc gaaaatgcac ggtgcgtttt caacgaacgt
3541 cgtagcaagc aaagaacttc aacagccagg cagtgcacga agcacgcgac atcttgaaat
3601 tgaacttcca aaagaagctt cttatcaaga aggagatcat ttaggtgtta ttcctcgcaa
3661 ctatgaagga atagtaaacc gtgtaacagc aaggttcggc ctagatgcat cacagcaaat
3721 ccgtctggaa gcagaagaag aaaaattagc tcatttgcca ctcgctaaaa cagtatccgt
3781 agaagagctt ctgcaatacg tggagcttca agatcctgtt acgcgcacgc agcttcgcgc
3841 aatggctgct aaaacggtct gcccgccgca taagtagag cttgaagcct tgcttgaaaa
3901 gcaagcctac aaagaacaag tgctggcaaa acgtttaaca atgcttgaac tgcttgaaaa
3961 atacccggcg tgtgaaatga aattcagcga atttatcgcc cttctgccaa gcatacgccc
4021 gcgctattac tcgatttctt catcacctcg tgtcgatgaa aaacaagcaa gcatcacggt
4081 cagcgttgtc tcaggagaag cgtggagcgg atatggagaa tataaaggaa ttgcgtcgaa
4141 ctatcttgcc gagctgcaag aaggagatac gattacgtgc tttatttcca caccgcagtc
4201 agaatttacg ctgccaaaag accctgaaac gccgcttatc atggtcggac cgggaacagg
4261 cgtcgcgccg tttagaggct ttgtgcaggc gcgcaaacag ctaaaagaac aaggacagtc
4321 acttggagaa gcacatttat acttcggctg ccgttcacct catgaagact atctgtatca
4381 agaagagctt gaaaacgccc aaagcgaagg catcattacg cttcataccg cttttctcg
4441 catgccaaat cagccgaaaa catacgttca gcacgtaatg aacaagacg gcaagaaatt
4501 gattgaactt cttgatcaag gagcgcactt ctatatttgc ggagacggaa gccaaatggc
4561 acctgccgtt gaagcaacgc ttatgaaaag ctatgctgac gttcaccaag tgagtgaagc
4621 agacgctcgc ttatggctgc agcagctaga agaaaaaggc cgatacgcaa aagacgtgtg
4681 ggctgggtaa attaaaaaga ggctaggata aaagtagttt agttggttga aggaagatcc
4741 gaacgatgaa tcgttcggat cttttattg gtagagtaaa cgtagatttc atctatttag
4801 tgacttgtag cggttgattg gagggcaagg tgaagactcc aatcaaccgc ggtgtcacat
4861 gcaagccata cgaaattcat ttctcccatt tattcgtctt ttgtccccac ttaattttta
4921 tagcgcctta acgtttcttc tgcgtgacag cagatct
```

FIGURE 1B

```
   1 mtikempqpk tfgelknlpl lntdkpvqal mkiadelgei fkfeapgrvt rylssqrlik
  61 eacdesrfdk nlsqalkfvr dfagdglfts wtheknwkka hnillpsfsq qamkgyhamm
 121 vdiavqlvqk werlnadehi evpedmtrlt ldtiglcgfn yrfnsfyrdq phpfitsmvr
 181 aldeamnklq ranpddpayd enkrqfqedi kvmndlvdki iadrkasgeq sddllthmln
 241 gkdpetgepl ddeniryqii tfliaghett sgllsfalyf lvknphvlqk aaeeaarvlv
 301 dpvpsykqvk qlkyvgmvln ealrlwptap afslyakedt vlggeyplek gdelmvlipq
 361 lhrdktiwgd dveefrperf enpsaipqha fkpfgngqra cigqqfalhe atlvlgmmlk
 421 hfdfedhtny eldiketltl kpegfvvkak skkiplggip spsteqsakk vrkkaenahn
 481 tpllvlygsn mgtaegtard ladiamskgf apqvatldsh agnlpregav livtasyngh
 541 ppdnakqfvd wldqasadev kgvrysvfgc gdknwattyq kvpafidetl aakgaeniad
 601 rgeadasddf egtyeewreh mwsdvaayfn ldiensednk stlslqfvds aadmplakmh
 661 gafstnvvas kelqqpgsar strhleielp keasyqegdh lgviprnyeg ivnrvtarfg
 721 ldasqqirle aeeeklahlp laktvsveel lqyvelqdpv trtqlramaa ktvcpphkve
 781 leallekqay keqvlakrlt mlellekypa cemkfsefia llpsirpryy sisssprvde
 841 kqasitvsvv sgeawsgyge ykgiasnyla elqegdtitc fistpqseft lpkdpetpli
 901 mvgpgtgvap frgfvqarkq lkeqgqslge ahlyfgcrsp hedylyqeel enaqsegiit
 961 lhtafsrmpn qpktyvqhvm eqdgkkliel ldqgahfyic gdgsqmapav eatlmksyad
1021 vhqvseadar lwlqqleekg ryakdvwag
```

FIGURE 2

GenBank Accession No:

| | | |
|---|---|---|
| P14779 | TIKEHPQPKTFGELKNLPLLNTDKPVQALHKIADELGEIFKFEAPGRVTR | 50 |
| D69799 | ----IPQPKTFGPLGNLPLIDKDKPTLSLIKLAEEQGPIFQIHTPAGTTI | 46 |
| O08336 | ----IPQPKTYGPLKNLPHLEKEQLSQSLWRIADELGPIFRFDFPGVSSV | 46 |
| CAB66201.1 | ------------------------PHQDSLRYARRLGPJFRRRAFGKEFV | 26 |
| BAA82526.1 | ----IPEPPGYPLIGNLGEFTSNPLS-DLNRLADTYGPIFRLRLGAKAPI | 45 |
| AAG27132.1 | -LRPIPGPKPLPLLGNLFDFDFDNLTKSLGELGKIHGPIYSITFGASTEI | 49 |
| | . . * *: . | |

```
YLSSQRLIKEACDESRFDKNLSQALKFVRDFAGDGLFTSWTHEKNWKKAH 100
VVSGHELVKEVCDEERFDKSIEGALEKVRAFSGDGLFTSWTHEPNWRKAH 96
FVSGHNLVAEVCDEKRFDKNLGKGLQKVREFGGDGLFTSWTHEPNWQKAH 96
FVWGAALAADLADEARFAKHVGLGVANLRPVAGDGLFTAYNHEPNWQLAH 76
FVSSNSLINEVCDEKRFKKTLKSVLSQVREGVHDGLFTAFEDEPNWGKAH 95
MVTSREIAQELCDETRFCKLPGGALDVHKAVVGDGLFTAETSNPKWAIAH 99
  :  . :  :   .**  **  *     :   ::   *****:   : :*   **

NILLPSFSQQAMKGYHAMMVDIAVQLVQKWERLNAD-EHIEVPEDMTRLT 149
NILHPTFSQRAMKDYHEKMVDIAVQLIQKWARLNPN-EAVDVPGDMTRLT 145
RILLPSFSQKAMKGYHSMMLDIATQLIQKWSRLNPN-EEIDVADDMTRLT 145
DVLAPGFSREAMAGYHVMMLDVAARLTGHWDLAEASGRAVDVPGDMTKLT 126
RILVPAFGPLSIRGMFPEMHDIATQLCMKFARHGPR-TPIDTSDNFTRLA 144
RIITPLFGAMRIRGMFDDMKDICEQMCLRWARFGPD-EPLNVCDNMTKLT 148
 ::  * *.    :  .  *  *:. ::  ::       . ::.   ::*:*:

LDTIGLCGFNYRFNSFYRDQ--PHPFITSMVRALDEAMNKLQRANPDDPA 197
LDTIGLCGFNYRFNSYYRET--PHPFINSMVRALDEAMHQMQRLDVQDKL 193
LDTIGLCGFNYRFNSFYRDS--QHPFITSMLRALKEAMNQSKRLGLQDKM 193
LETIARTGFGHDFGSFERSR--LHPFVTAMVGTLGYAQRLNTVPAPLAPW 174
LDTLALCAMDFRFYSYYKEE--LHPFIEAMGDFLTESGNRNRRPPFAPNF 192
LDTIALCTIDYRFNSFYRENGAAHPFAEAVVDVMTESFDQSNLPDFVNNY 198
*:*:.    :.. * *: :.    ***   ::    :  :

YDENK-RQFQEDIKVMNDLVDKIIADRKASG--------EQSD-DLLTHM 237
MVRTK-RQFRYDIQTMFSLVDSIIAERRANG--------DQDEKDLLARM 234
MVKTK-LQFQKDIEVMNSLVDRMIAERKANP--------DENIKDLLSLM 234
LLRDASRRNAADIAHLNRTVDDLVRERRANGGTGGGTGSGSGSGDLLDRM 224
LYRAANEKFYGDIALMKSVADEVVAARKASP---------SDRKDLLAAM 233
VRFRAMAKFKRQAAELRRQTEELIAARRQNP---------VDRDDLLNAM 239
   :      :     :   .:  ::  *: .          . ***  *

LNGKDPETGEPLDDENIRYQIITFLIAGHETTSGLLSFALYFLVKNPHVL 287
LNVEDPETGEKLDDENIRFQIITFLIAGHETTSGLLSFATYFLLKHPDKL 284
LYAKDPVTGETLDDENIRYQIITFLIAGHETTSGLLSFAIYCLLTHPEKL 284
LETAHPRTGERLSPQNVRRQVITFLVAGHETTSGALSFALHYLAQHPDVA 274
LNGVDPQTGEKLSDENITNQLITFLIAGHETTSGTLSFAMYQLLKNPEAY 283
LSAKDPKTGEGLSPESIVDNLLTFLIAGHETTSSLLSFCFYYLLENPHVL 289
 *   .* *** *. :.: :::*******. ***. : *  :*.
```

FIGURE 4A

```
QKAAEEAARVLVD-PVPSYKQVKQLKYVGMVLNEALRLWPTAPAFSLYAK  336
KKAYEEVDRVLTD-AAPTYKQVLELTYIRMILNESLRLWPTAPAFSLYPK  333
KKAQEEADRVLTD-DTPEYKQIQQLKYIRMVLNETLRLYPTAPAFSLYAK  333
ARARAEVDRVWGDTEAPGYEQVAKLRYVRRVLDESLRLWPTAPGFAREAR  324
SKVQKEVDEVVGR-GPVLVEHLTKLPYISAVLRETLRLNSPITAFGLEAI  332
RRVQQEVDTVVGS-DTITVDHLSSMPYLEAVLRETLRLRDPGPGFYVKPL  338
 :.  *. *          .::  .: *:   :* *:***   ...*  .

EDTVLGGEYPLEKGDELMVLIPQLHRDKTIWGDDVEEFRPERFENPSA--  384
EDTVIGGKFPITTNDRISVLIPQLHRDRDAWGKDAEEFRPERFEHQDQ--  381
EDTVLGGEYPISKGQPVTVLIPKLHRDQNAWGPDAEDFRPERFEDPSS--  381
EDTVLGGTHPMRRGAWALVLTGMLHRDPEVWGADAERFDPDRFDAKAVRS  374
DDTFLGGKYLVKKGEIVTALLSRGHVDPVVYGNDADKFIPERMLDDEFAR  382
KDEVVAGKYAVNKDQPLFIVFDSVHRDQSTYGADADEFRPERMLKDGFDK  388
 .*  ..:.*  .  :   .       :    * *   :* *.:  * *:*:

IP---QHAFKPFGNGQRACIGQQFALHEATLVLGMMLKHFDFED-HTNYE  430
VP---HHAYKPFGNGQRACIGMQFALHEATLVLGMILKYFTLID-HENYE  427
IP---HHAYKPFGNGQRACIGMQFALQEATMVLGLVLKHFELIN-HTGYE  427
RA---PHTFKPFGTGARACIGRQFALHEATLVLGLLLRRYELRP-EPGYR  420
LNKEYPNCWKPFGNGKRACIGRPFAWQESLLAMVVLFQNFNFTMTDPNYA  432
LP---PCAWKPFGNGVRACVGRPFAMQQAILAVAMVLHKFDLVK-DESYT  434
      :****.* ***:*  ** ::: :.: :::: : :    . .*

LDIKETLTLKPEGFVVKAKSKKIPLGGIPSPST  463
LDIKQTLTLKPGDFHISVQSR------------  448
LKIKEALTIKPDDFKITVKPRK-----------  449
LRVTERLTLMPEG--------------------  433
LEIKQTLTIKPDHFYINA---------------  450
LKYHVTMTVRPVGFTMKVRLRQ-----------  456
*         :*: *
```

FIGURE 4B

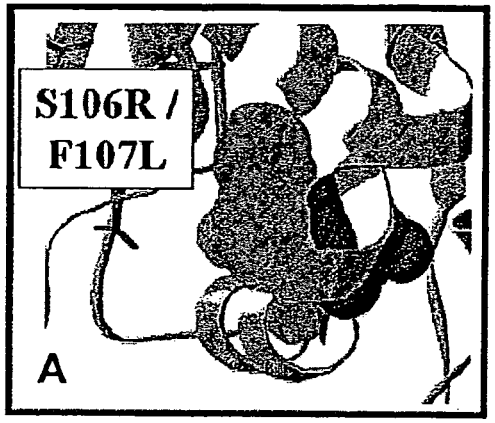
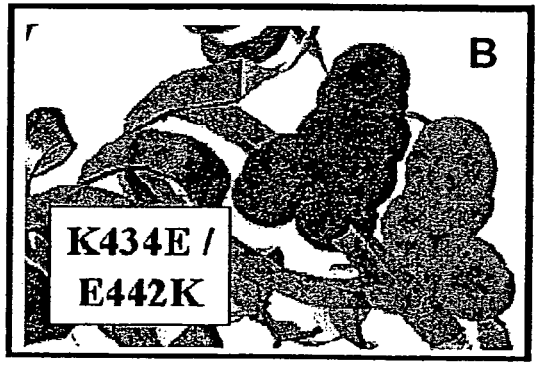
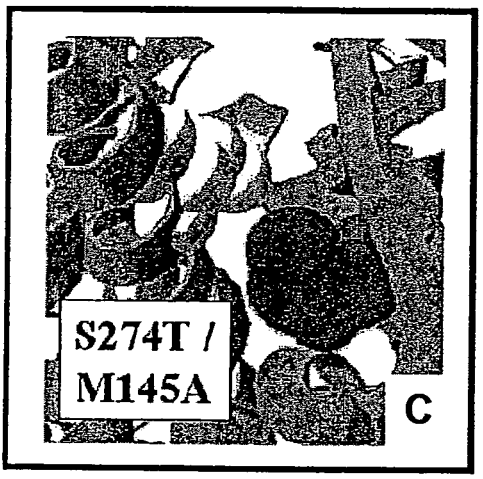
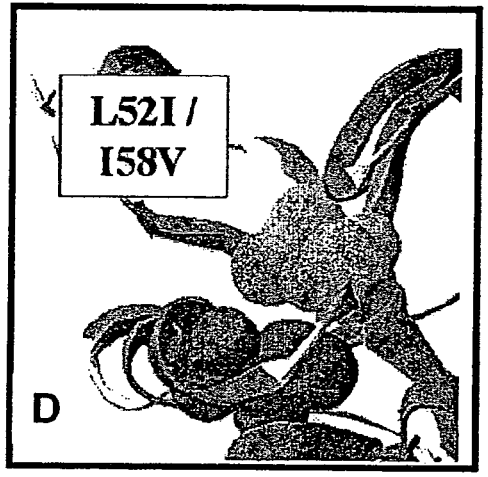
FIGURE 7

SEQUENCE LISTING

<160> NUMBER OF SEQ ID NOS: 12

<210> SEQ ID NO 1
<211> LENGTH: 4957
<212> TYPE: DNA
<213> ORGANISM: Bacillus megaterium

<400> SEQUENCE: 1

| | | | | | |
|---|---|---|---|---|---|
| agatctttat | gaagacatag | ctgcagaaga | aaaagcaaga | gctacatatc | aatggttaat | 60 |
| tgatatatca | gatgatcccg | atttaaacga | cagcttacga | tttttacgag | aaagagagat | 120 |
| tgttcactca | cagcggttcc | gcgaggccgt | ggagatttta | aaagatgaca | gagacaggaa | 180 |
| gaaaatcttt | taactagtaa | aaaaacatcc | cccttggcga | atgcaaacga | aaggagggat | 240 |
| gttttttgtt | gtgactgcgt | tgattatgcg | ctagaactgc | agtgacaaga | acaacccttt | 300 |
| aatttccctt | caacatcttt | ccaaactcgc | gtataactgt | attcacctcc | aatagattca | 360 |
| ccggttgcca | gtgccccatt | taacgctact | tttgtaacgg | taacggcaag | ttcttgaaac | 420 |
| agtttaactt | cttgttccaa | cacttccatg | cccgctatat | caagactttt | tgaacgatga | 480 |
| acatttatat | cttcttcttt | tgacaaccat | tgcccaaggt | gattcacaaa | ataagctca | 540 |
| tctgaaagta | attcttctaa | tagctctatg | ttattagaaa | gcatggctga | gcgaagcatt | 600 |
| tcttcgtatt | ctataactct | tgcttgattc | atttttaatc | ctcctttacg | ccttgtgtaa | 660 |
| ctcttttcta | tttccacgtt | gcttttcctt | taaacttctt | tcattaataa | ttcgtgctaa | 720 |
| attatgttaa | tagaggggat | aagtggacta | attttctgta | agcactaaat | attctgaaat | 780 |
| actctgttaa | ttacctttaa | atggtataaa | attagaatga | agaaccttt | tctttccact | 840 |
| tttctagtta | tcttttact | attaagatgc | agttttttat | acttgtaatt | gtagcggaat | 900 |
| gaacgttcat | tccgttttg | aaagaggtg | ataaagtgga | atctactcca | acaaaacaaa | 960 |
| aagcgatttt | ttctgcttcg | cttctgctgt | ttgcagaaag | agggtttgat | gcaaccacga | 1020 |
| tgccaatgat | tgcagagaat | gccaaagtag | gagcaggaac | aatttatcgc | tactttaaaa | 1080 |
| ataaagaaag | ccttgtaaat | gaattattcc | aacagcacgt | aaacgagttt | ttacagtgca | 1140 |
| ttgaaagcgg | tctggcaaac | gagagagatg | gataccgaga | tgggtttcat | catatctttg | 1200 |
| aaggtatggt | gacatttact | aaaaaccatc | ctcgtgctct | tggatttatt | aaaactcata | 1260 |
| gccaaggaac | ttttttaaca | gaagagagcc | gcttagcata | tcaaaagctg | gtggaatttg | 1320 |
| tttgtacgtt | cttcagagaa | ggacaaaagc | aaggtgtgat | tagaaatctt | cctgaaaatg | 1380 |
| cgctaattgc | tattttattt | ggaagtttca | tggaagtata | tgaaatgatt | gaaaatgact | 1440 |
| acttatcttt | aactgatgaa | cttcttaccg | gtgtagaaga | gagtctgtgg | gcagcactta | 1500 |
| gcagacaatc | atgaaactta | acaagtgaaa | gagggataac | atgacaatta | aagaaatgcc | 1560 |
| tcagccaaaa | acgtttggag | agcttaaaaa | tttaccgtta | ttaaacacag | ataaaccggt | 1620 |
| tcaagctttg | atgaaaattg | cggatgaatt | aggagaaatc | tttaaattcg | aggcgcctgg | 1680 |
| tcgtgtaacg | cgctacttat | caagtcagcg | tctaattaaa | gaagcatgcg | atgaatcacg | 1740 |
| ctttgataaa | aacttaagtc | aagcgcttaa | atttgtacgt | gattttgcag | gagacgggtt | 1800 |
| atttacaagc | tggacgcatg | aaaaaaattg | gaaaaagcg | cataatatct | tacttccaag | 1860 |
| cttcagtcag | caggcaatga | aaggctatca | tgcgatgatg | gtcgatatcg | ccgtgcagct | 1920 |
| tgttcaaaag | tgggagcgtc | taaatgcaga | tgagcatatt | gaagtaccgg | aagacatgac | 1980 |
| acgtttaacg | cttgatacaa | ttggtctttg | cggctttaac | tatcgcttta | acagctttta | 2040 |

```
ccgagatcag cctcatccat ttattacaag tatggtccgt gcactggatg aagcaatgaa    2100
caagctgcag cgagcaaatc cagacgaccc agcttatgat gaaaacaagc gccagtttca    2160
agaagatatc aaggtgatga acgacctagt agataaaatt attgcagatc gcaaagcaag    2220
cggtgaacaa agcgatgatt tattaacgca tatgctaaac ggaaaagatc cagaaacggg    2280
tgagccgctt gatgacgaga acattcgcta tcaaattatt acattcttaa ttgcgggaca    2340
cgaaacaaca agtggtcttt tatcatttgc gctgtatttc ttagtgaaaa atccacatgt    2400
attacaaaaa gcagcagaag aagcagcacg agttctagta gatcctgttc caagctacaa    2460
acaagtcaaa cagcttaaat atgtcggcat ggtcttaaac gaagcgctgc gcttatggcc    2520
aactgctcct gcgttttccc tatatgcaaa agaagatacg gtgcttggag agaatatcc    2580 tttagaaaaa ggcgacgaac taatggttct gattcctcag cttcaccgtg ataaaacaat    2640
ttggggagac gatgtggaag agttccgtcc agagcgtttt gaaatccaa gtgcgattcc    2700 gcagcatgcg tttaaaccgt tggaaacggg tcagcgtgcg tgtatcggtc agcagttcgc    2760
tcttcatgaa gcaacgctgg tacttggtat gatgctaaaa cactttgact ttgaagatca    2820
tacaaactac gagctggata ttaaagaaac tttaacgtta aaacctgaag ctttgtggt    2880 aaaagcaaaa tcgaaaaaaa ttccgcttgg cggtattcct tcacctagca ctgaacagtc    2940
tgctaaaaaa gtacgcaaaa aggcagaaaa cgctcataat acgccgctgc ttgtgctata    3000
cggttcaaat atgggaacag ctgaaggaac ggcgcgtgat ttagcagata ttgcaatgag    3060
caaaggattt gcaccgcagg tcgcaacgct tgattcacac gccggaaatc ttccgcgcga    3120
aggagctgta ttaattgtaa cggcgtctta taacggtcat ccgcctgata acgcaaagca    3180
atttgtcgac tggttagacc aagcgtctgc tgatgaagta aaaggcgttc gctactccgt    3240
atttggatgc ggcgataaaa actgggctac tacgtatcaa aaagtgcctg cttttatcga    3300
tgaaacgctt gccgctaaag gggcagaaaa catcgctgac cgcggtgaag cagatgcaag    3360
cgacgacttt gaaggcacat atgaagaatg gcgtgaacat atgtggagtg acgtagcagc    3420
ctactttaac ctcgacattg aaaacagtga agataataaa tctactcttt cacttcaatt    3480
tgtcgacagc gccgcggata tgccgcttgc gaaaatgcac ggtgcgtttt caacgaacgt    3540
cgtagcaagc aaagaacttc aacagccagg cagtgcacga agcacgcgac atcttgaaat    3600
tgaacttcca aaagaagctt cttatcaaga aggagatcat ttaggtgtta ttcctcgcaa    3660
ctatgaagga atagtaaacc gtgtaacagc aaggttcggc ctagatgcat cacagcaaat    3720
ccgtctggaa gcagaagaag aaaaattagc tcatttgcca ctcgctaaaa cagtatccgt    3780
agaagagctt ctgcaatacg tggagcttca agatcctgtt acgcgcacgc agcttcgcgc    3840
aatggctgct aaaacggtct gcccgccgca taaagtagag cttgaagcct tgcttgaaaa    3900
gcaagcctac aaagaacaag tgctggcaaa acgtttaaca atgcttgaac tgcttgaaaa    3960
atacccggcg tgtgaaatga aattcagcga atttatcgcc cttctgccaa gcatacgccc    4020
gcgctattac tcgatttctt catcacctcg tgtcgatgaa aaacaagcaa gcatcacggt    4080
cagcgttgtc tcaggagaag cgtggagcgg atatggagaa tataaaggaa ttgcgtcgaa    4140
ctatcttgcc gagctgcaag aaggagatac gattacgtgc tttatttcca caccgcagtc    4200
agaatttacg ctgccaaaag accctgaaac gccgcttatc atggtcggac cgggaacagg    4260
cgtcgcgccg tttagaggct ttgtgcaggc gcgcaaacag ctaaagaac aaggacagtc    4320 acttggagaa gcacatttat acttcggctg ccgttcacct catgaagact atctgtatca    4380
```

```
agaagagctt gaaaacgccc aaagcgaagg catcattacg cttcataccg ctttttctcg    4440
catgccaaat cagccgaaaa catacgttca gcacgtaatg aacaagacg gcaagaaatt     4500 gattgaactt cttgatcaag gagcgcactt ctatatttgc ggagacggaa gccaaatggc    4560
acctgccgtt gaagcaacgc ttatgaaaag ctatgctgac gttcaccaag tgagtgaagc    4620
agacgctcgc ttatggctgc agcagctaga agaaaaaggc cgatacgcaa aagacgtgtg    4680
ggctgggtaa attaaaaaga ggctaggata aaagtagttt agttggttga aggaagatcc    4740
gaacgatgaa tcgttcggat cttttttattg gtagagtaaa cgtagatttc atctatttag   4800
tgacttgtag cggttgattg gagggcaagg tgaagactcc aatcaaccgc ggtgtcacat    4860
gcaagccata cgaaattcat ttctcccatt tattcgtctt ttgtccccac ttaatttta     4920 tagcgcctta acgtttcttc tgcgtgacag cagatct                             4957
```

<210> SEQ ID NO 2
<211> LENGTH: 1049
<212> TYPE: PRT
<213> ORGANISM: Bacillus megaterium GenBank / P14779

<400> SEQUENCE: 2

```
Met Thr Ile Lys Glu Met Pro Gln Pro Lys Thr Phe Gly Glu Leu Lys
 1               5                  10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
           100                 105                 110

Met Lys Gly Tyr His Ala Met Met Val Asp Ile Ala Val Gln Leu Val
       115                 120                 125

Gln Lys Trp Glu Arg Leu Asn Ala Asp Glu His Ile Glu Val Pro Glu
   130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
           180                 185                 190

Asn Pro Asp Asp Pro Ala Tyr Asp Glu Asn Lys Arg Gln Phe Gln Glu
       195                 200                 205

Asp Ile Lys Val Met Asn Asp Leu Val Asp Lys Ile Ile Ala Asp Arg
   210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
           260                 265                 270
```

```
Leu Leu Ser Phe Ala Leu Tyr Phe Leu Val Lys Asn Pro His Val Leu
            275                 280                 285

Gln Lys Ala Ala Glu Glu Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
            355                 360                 365

Gly Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
            530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
```

```
                 690             695             700
Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
            805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 3
<211> LENGTH: 464
<212> TYPE: PRT
<213> ORGANISM: Bacillus subtilis GenBank / P14779

<400> SEQUENCE: 3

Met Thr Ile Lys Glu Met Pro Gln Pro Lys Thr Phe Gly Glu Leu Lys
1               5                   10                  15
```

-continued

```
Asn Leu Pro Leu Leu Asn Thr Asp Lys Pro Val Gln Ala Leu Met Lys
         20                  25                  30
Ile Ala Asp Glu Leu Gly Glu Ile Phe Lys Phe Glu Ala Pro Gly Arg
             35                  40                  45
Val Thr Arg Tyr Leu Ser Ser Gln Arg Leu Ile Lys Glu Ala Cys Asp
 50                  55                  60
Glu Ser Arg Phe Asp Lys Asn Leu Ser Gln Ala Leu Lys Phe Val Arg
 65                  70                  75                  80
Asp Phe Ala Gly Asp Gly Leu Phe Thr Ser Trp Thr His Glu Lys Asn
                 85                  90                  95
Trp Lys Lys Ala His Asn Ile Leu Leu Pro Ser Phe Ser Gln Gln Ala
            100                 105                 110
Met Lys Gly Tyr His Ala Met Met Val Asp Ile Ala Val Gln Leu Val
            115                 120                 125
Gln Lys Trp Glu Arg Leu Asn Ala Asp Glu His Ile Glu Val Pro Glu
130                 135                 140
Asp Met Thr Arg Leu Thr Leu Asp Thr Ile Gly Leu Cys Gly Phe Asn
145                 150                 155                 160
Tyr Arg Phe Asn Ser Phe Tyr Arg Asp Gln Pro His Pro Phe Ile Thr
                165                 170                 175
Ser Met Val Arg Ala Leu Asp Glu Ala Met Asn Lys Leu Gln Arg Ala
            180                 185                 190
Asn Pro Asp Asp Pro Ala Tyr Asp Glu Asn Lys Arg Gln Phe Gln Glu
            195                 200                 205
Asp Ile Lys Val Met Asn Asp Leu Val Asp Lys Ile Ile Ala Asp Arg
            210                 215                 220
Lys Ala Ser Gly Glu Gln Ser Asp Asp Leu Leu Thr His Met Leu Asn
225                 230                 235                 240
Gly Lys Asp Pro Glu Thr Gly Glu Pro Leu Asp Asp Glu Asn Ile Arg
                245                 250                 255
Tyr Gln Ile Ile Thr Phe Leu Ile Ala Gly His Glu Thr Thr Ser Gly
            260                 265                 270
Leu Leu Ser Phe Ala Leu Tyr Phe Leu Val Lys Asn Pro His Val Leu
            275                 280                 285
Gln Lys Ala Ala Glu Glu Ala Ala Arg Val Leu Val Asp Pro Val Pro
            290                 295                 300
Ser Tyr Lys Gln Val Lys Gln Leu Lys Tyr Val Gly Met Val Leu Asn
305                 310                 315                 320
Glu Ala Leu Arg Leu Trp Pro Thr Ala Pro Ala Phe Ser Leu Tyr Ala
                325                 330                 335
Lys Glu Asp Thr Val Leu Gly Gly Glu Tyr Pro Leu Glu Lys Gly Asp
            340                 345                 350
Glu Leu Met Val Leu Ile Pro Gln Leu His Arg Asp Lys Thr Ile Trp
            355                 360                 365
Gly Asp Asp Val Glu Glu Phe Arg Pro Glu Arg Phe Glu Asn Pro Ser
    370                 375                 380
Ala Ile Pro Gln His Ala Phe Lys Pro Phe Gly Asn Gly Gln Arg Ala
385                 390                 395                 400
Cys Ile Gly Gln Gln Phe Ala Leu His Glu Ala Thr Leu Val Leu Gly
                405                 410                 415
Met Met Leu Lys His Phe Asp Phe Glu Asp His Thr Asn Tyr Glu Leu
            420                 425                 430
Asp Ile Lys Glu Thr Leu Thr Leu Lys Pro Glu Gly Phe Val Val Lys
```

```
                    435                 440                 445
Ala Lys Ser Lys Lys Ile Pro Leu Gly Gly Ile Pro Ser Pro Ser Thr
    450                 455                 460

<210> SEQ ID NO 4
<211> LENGTH: 1054
<212> TYPE: PRT
<213> ORGANISM: Bacillus subtilis GenBank / O08336

<400> SEQUENCE: 4

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
            20                  25                  30

Arg Ile Ala Asp Glu Leu Gly Pro Ile Phe Arg Phe Asp Phe Pro Gly
        35                  40                  45

Val Ser Ser Val Phe Val Ser Gly His Asn Leu Val Ala Glu Val Cys
    50                  55                  60

Asp Glu Lys Arg Phe Asp Lys Asn Leu Gly Lys Gly Leu Gln Lys Val
65                  70                  75                  80

Arg Glu Phe Gly Gly Asp Gly Leu Phe Thr Ser Trp Thr His Glu Pro
                85                  90                  95

Asn Trp Gln Lys Ala His Arg Ile Leu Leu Pro Ser Phe Ser Gln Lys
            100                 105                 110

Ala Met Lys Gly Tyr His Ser Met Met Leu Asp Ile Ala Thr Gln Leu
        115                 120                 125

Ile Gln Lys Trp Ser Arg Leu Asn Pro Asn Glu Glu Ile Asp Val Ala
    130                 135                 140

Asp Asp Met Thr Arg Leu Thr Leu Asp Thr Ile Gly Leu Cys Gly Phe
145                 150                 155                 160

Asn Tyr Arg Phe Asn Ser Phe Tyr Arg Asp Ser Gln His Pro Phe Ile
                165                 170                 175

Thr Ser Met Leu Arg Ala Leu Lys Glu Ala Met Asn Gln Ser Lys Arg
            180                 185                 190

Leu Gly Leu Gln Asp Lys Met Met Val Lys Thr Lys Leu Gln Phe Gln
        195                 200                 205

Lys Asp Ile Glu Val Met Asn Ser Leu Val Asp Arg Met Ile Ala Glu
    210                 215                 220

Arg Lys Ala Asn Pro Asp Glu Asn Ile Lys Asp Leu Leu Ser Leu Met
225                 230                 235                 240

Leu Tyr Ala Lys Asp Pro Val Thr Gly Glu Thr Leu Asp Asp Glu Asn
                245                 250                 255

Ile Arg Tyr Gln Ile Ile Thr Phe Leu Ile Ala Gly His Glu Thr Thr
            260                 265                 270

Ser Gly Leu Leu Ser Phe Ala Ile Tyr Cys Leu Leu Thr His Pro Glu
        275                 280                 285

Lys Leu Lys Lys Ala Gln Glu Glu Ala Asp Arg Val Leu Thr Asp Asp
    290                 295                 300

Thr Pro Glu Tyr Lys Gln Ile Gln Gln Leu Lys Tyr Ile Arg Met Val
305                 310                 315                 320

Leu Asn Glu Thr Leu Arg Leu Tyr Pro Thr Ala Pro Ala Phe Ser Leu
                325                 330                 335

Tyr Ala Lys Glu Asp Thr Val Leu Gly Gly Glu Tyr Pro Ile Ser Lys
            340                 345                 350
```

```
Gly Gln Pro Val Thr Val Leu Ile Pro Lys Leu His Arg Asp Gln Asn
        355                 360                 365
Ala Trp Gly Pro Asp Ala Glu Asp Phe Arg Pro Glu Arg Phe Glu Asp
    370                 375                 380
Pro Ser Ser Ile Pro His His Ala Tyr Lys Pro Phe Gly Asn Gly Gln
385                 390                 395                 400
Arg Ala Cys Ile Gly Met Gln Phe Ala Leu Gln Glu Ala Thr Met Val
                405                 410                 415
Leu Gly Leu Val Leu Lys His Phe Glu Leu Ile Asn His Thr Gly Tyr
            420                 425                 430
Glu Leu Lys Ile Lys Glu Ala Leu Thr Ile Lys Pro Asp Asp Phe Lys
        435                 440                 445
Ile Thr Val Lys Pro Arg Lys Thr Ala Ala Ile Asn Val Gln Arg Lys
    450                 455                 460
Glu Gln Ala Asp Ile Lys Ala Glu Thr Lys Pro Lys Glu Thr Lys Pro
465                 470                 475                 480
Lys His Gly Thr Pro Leu Leu Val Leu Phe Gly Ser Asn Leu Gly Thr
                485                 490                 495
Ala Glu Gly Ile Ala Gly Glu Leu Ala Ala Gln Gly Arg Gln Met Gly
            500                 505                 510
Phe Thr Ala Glu Thr Ala Pro Leu Asp Asp Tyr Ile Gly Lys Leu Pro
        515                 520                 525
Glu Glu Gly Ala Val Val Ile Val Thr Ala Ser Tyr Asn Gly Ala Pro
    530                 535                 540
Pro Asp Asn Ala Ala Gly Phe Val Glu Trp Leu Lys Glu Leu Glu Glu
545                 550                 555                 560
Gly Gln Leu Lys Gly Val Ser Tyr Ala Val Phe Gly Cys Gly Asn Arg
                565                 570                 575
Ser Trp Ala Ser Thr Tyr Gln Arg Ile Pro Arg Leu Ile Asp Asp Met
            580                 585                 590
Met Lys Ala Lys Gly Ala Ser Arg Leu Thr Ala Ile Gly Glu Gly Asp
        595                 600                 605
Ala Ala Asp Asp Phe Glu Ser His Arg Glu Ser Trp Glu Asn Arg Phe
    610                 615                 620
Trp Lys Glu Thr Met Asp Ala Phe Asp Ile Asn Glu Ile Ala Gln Lys
625                 630                 635                 640
Glu Asp Arg Pro Ser Leu Ser Ile Thr Phe Leu Ser Glu Ala Thr Glu
                645                 650                 655
Thr Pro Val Ala Lys Ala Tyr Gly Ala Phe Glu Gly Ile Val Leu Glu
            660                 665                 670
Asn Arg Glu Leu Gln Thr Ala Ala Ser Thr Arg Ser Thr Arg His Ile
        675                 680                 685
Glu Leu Glu Ile Pro Ala Gly Lys Thr Tyr Lys Glu Gly Asp His Ile
    690                 695                 700
Gly Ile Leu Pro Lys Asn Ser Arg Glu Leu Val Gln Arg Val Leu Ser
705                 710                 715                 720
Arg Phe Gly Leu Gln Ser Asn His Val Ile Lys Val Ser Gly Ser Ala
                725                 730                 735
His Met Ala His Leu Pro Met Asp Arg Pro Ile Lys Val Val Asp Leu
            740                 745                 750
Leu Ser Ser Tyr Val Glu Leu Gln Glu Pro Ala Ser Arg Leu Gln Leu
        755                 760                 765
Arg Glu Leu Ala Ser Tyr Thr Val Cys Pro Pro His Gln Lys Glu Leu
```

```
              770                 775                 780
Glu Gln Leu Val Ser Asp Asp Gly Ile Tyr Lys Glu Gln Val Leu Ala
785                 790                 795                 800

Lys Arg Leu Thr Met Leu Asp Phe Leu Glu Asp Tyr Pro Ala Cys Glu
                805                 810                 815

Met Pro Phe Glu Arg Phe Leu Ala Leu Leu Pro Ser Leu Lys Pro Arg
                820                 825                 830

Tyr Tyr Ser Ile Ser Ser Ser Pro Lys Val His Ala Asn Ile Val Ser
                835                 840                 845

Met Thr Val Gly Val Val Lys Ala Ser Ala Trp Ser Gly Arg Gly Glu
850                 855                 860

Tyr Arg Gly Val Ala Ser Asn Tyr Leu Ala Glu Leu Asn Thr Gly Asp
865                 870                 875                 880

Ala Ala Ala Cys Phe Ile Arg Thr Pro Gln Ser Gly Phe Gln Met Pro
                885                 890                 895

Asn Asp Pro Glu Thr Pro Met Ile Met Val Gly Pro Gly Thr Gly Ile
                900                 905                 910

Ala Pro Phe Arg Gly Phe Ile Gln Ala Arg Ser Val Leu Lys Lys Glu
                915                 920                 925

Gly Ser Thr Leu Gly Glu Ala Leu Leu Tyr Phe Gly Cys Arg Arg Pro
930                 935                 940

Asp His Asp Asp Leu Tyr Arg Glu Glu Leu Asp Gln Ala Glu Gln Asp
945                 950                 955                 960

Gly Leu Val Thr Ile Arg Arg Cys Tyr Ser Arg Val Glu Asn Glu Pro
                965                 970                 975

Lys Gly Tyr Val Gln His Leu Leu Lys Gln Asp Thr Gln Lys Leu Met
                980                 985                 990

Thr Leu Ile Glu Lys Gly Ala His Ile Tyr Val Cys Gly Asp Gly Ser
                995                1000                1005

Gln Met Ala Pro Asp Val Glu Arg Thr Leu Arg Leu Ala Tyr Glu
               1010                1015                1020

Ala Glu Lys Ala Ala Ser Gln Glu Glu Ser Ala Val Trp Leu Gln
               1025                1030                1035

Lys Leu Gln Asp Gln Arg Arg Tyr Val Lys Asp Val Trp Thr Gly
               1040                1045                1050

Met

<210> SEQ ID NO 5
<211> LENGTH: 1054
<212> TYPE: PRT
<213> ORGANISM: Bacillus subtilis GenBank / A69975

<400> SEQUENCE: 5

Met Lys Gln Ala Ser Ala Ile Pro Gln Pro Lys Thr Tyr Gly Pro Leu
1               5                   10                  15

Lys Asn Leu Pro His Leu Glu Lys Glu Gln Leu Ser Gln Ser Leu Trp
                20                  25                  30

Arg Ile Ala Asp Glu Leu Gly Pro Ile Phe Arg Phe Asp Phe Pro Gly
            35                  40                  45

Val Ser Ser Val Phe Val Ser Gly His Asn Leu Val Ala Glu Val Cys
        50                  55                  60

Asp Glu Lys Arg Phe Asp Lys Asn Leu Gly Lys Gly Leu Gln Lys Val
65              70                  75                  80

Arg Glu Phe Gly Gly Asp Gly Leu Phe Thr Ser Trp Thr His Glu Pro
```

-continued

```
                85                  90                  95
Asn Trp Gln Lys Ala His Arg Ile Leu Leu Pro Ser Phe Ser Gln Lys
            100                 105                 110
Ala Met Lys Gly Tyr His Ser Met Met Leu Asp Ile Ala Thr Gln Leu
            115                 120                 125
Ile Gln Lys Trp Ser Arg Leu Asn Pro Asn Glu Glu Ile Asp Val Ala
            130                 135                 140
Asp Asp Met Thr Arg Leu Thr Leu Asp Thr Ile Gly Leu Cys Gly Phe
145                 150                 155                 160
Asn Tyr Arg Phe Asn Ser Phe Tyr Arg Asp Ser Gln His Pro Phe Ile
                165                 170                 175
Thr Ser Met Leu Arg Ala Leu Lys Glu Ala Met Asn Gln Ser Lys Arg
            180                 185                 190
Leu Gly Leu Gln Asp Lys Met Met Val Lys Thr Lys Leu Gln Phe Gln
            195                 200                 205
Lys Asp Ile Glu Val Met Asn Ser Leu Val Asp Arg Met Ile Ala Glu
            210                 215                 220
Arg Lys Ala Asn Pro Asp Glu Asn Ile Lys Asp Leu Leu Ser Leu Met
225                 230                 235                 240
Leu Tyr Ala Lys Asp Pro Val Thr Gly Glu Thr Leu Asp Asp Glu Asn
                245                 250                 255
Ile Arg Tyr Gln Ile Ile Thr Phe Leu Ile Ala Gly His Glu Thr Thr
                260                 265                 270
Ser Gly Leu Leu Ser Phe Ala Ile Tyr Cys Leu Leu Thr His Pro Glu
            275                 280                 285
Lys Leu Lys Lys Ala Gln Glu Glu Ala Asp Arg Val Leu Thr Asp Asp
            290                 295                 300
Thr Pro Glu Tyr Lys Gln Ile Gln Gln Leu Lys Tyr Ile Arg Met Val
305                 310                 315                 320
Leu Asn Glu Thr Leu Arg Leu Tyr Pro Thr Ala Pro Ala Phe Ser Leu
                325                 330                 335
Tyr Ala Lys Glu Asp Thr Val Leu Gly Gly Glu Tyr Pro Ile Ser Lys
            340                 345                 350
Gly Gln Pro Val Thr Val Leu Ile Pro Lys Leu His Arg Asp Gln Asn
            355                 360                 365
Ala Trp Gly Pro Asp Ala Glu Asp Phe Arg Pro Glu Arg Phe Glu Asp
            370                 375                 380
Pro Ser Ser Ile Pro His His Ala Tyr Lys Pro Phe Gly Asn Gly Gln
385                 390                 395                 400
Arg Ala Cys Ile Gly Met Gln Phe Ala Leu Gln Glu Ala Thr Met Val
                405                 410                 415
Leu Gly Leu Val Leu Lys His Phe Glu Leu Ile Asn His Thr Gly Tyr
            420                 425                 430
Glu Leu Lys Ile Lys Glu Ala Leu Thr Ile Lys Pro Asp Asp Phe Lys
            435                 440                 445
Ile Thr Val Lys Pro Arg Lys Thr Ala Ala Ile Asn Val Gln Arg Lys
            450                 455                 460
Glu Gln Ala Asp Ile Lys Ala Glu Thr Lys Pro Lys Glu Thr Lys Pro
465                 470                 475                 480
Lys His Gly Thr Pro Leu Leu Val Leu Phe Gly Ser Asn Leu Gly Thr
                485                 490                 495
Ala Glu Gly Ile Ala Gly Glu Leu Ala Ala Gln Gly Arg Gln Met Gly
            500                 505                 510
```

-continued

```
Phe Thr Ala Glu Thr Ala Pro Leu Asp Asp Tyr Ile Gly Lys Leu Pro
        515                 520                 525
Glu Glu Gly Ala Val Val Ile Val Thr Ala Ser Tyr Asn Gly Ala Pro
    530                 535                 540
Pro Asp Asn Ala Ala Gly Phe Val Glu Trp Leu Lys Glu Leu Glu Glu
545                 550                 555                 560
Gly Gln Leu Lys Gly Val Ser Tyr Ala Val Phe Gly Cys Gly Asn Arg
                565                 570                 575
Ser Trp Ala Ser Thr Tyr Gln Arg Ile Pro Arg Leu Ile Asp Asp Met
            580                 585                 590
Met Lys Ala Lys Gly Ala Ser Arg Leu Thr Ala Ile Gly Glu Gly Asp
        595                 600                 605
Ala Ala Asp Asp Phe Glu Ser His Arg Glu Ser Trp Glu Asn Arg Phe
    610                 615                 620
Trp Lys Glu Thr Met Asp Ala Phe Asp Ile Asn Glu Ile Ala Gln Lys
625                 630                 635                 640
Glu Asp Arg Pro Ser Leu Ser Ile Thr Phe Leu Ser Glu Ala Thr Glu
                645                 650                 655
Thr Pro Val Ala Lys Ala Tyr Gly Ala Phe Glu Gly Ile Val Leu Glu
            660                 665                 670
Asn Arg Glu Leu Gln Thr Ala Ala Ser Thr Arg Ser Thr Arg His Ile
        675                 680                 685
Glu Leu Glu Ile Pro Ala Gly Lys Thr Tyr Lys Glu Gly Asp His Ile
    690                 695                 700
Gly Ile Leu Pro Lys Asn Ser Arg Glu Leu Val Gln Arg Val Leu Ser
705                 710                 715                 720
Arg Phe Gly Leu Gln Ser Asn His Val Ile Lys Val Ser Gly Ser Ala
                725                 730                 735
His Met Ala His Leu Pro Met Asp Arg Pro Ile Lys Val Val Asp Leu
            740                 745                 750
Leu Ser Ser Tyr Val Glu Leu Gln Glu Pro Ala Ser Arg Leu Gln Leu
        755                 760                 765
Arg Glu Leu Ala Ser Tyr Thr Val Cys Pro Pro His Gln Lys Glu Leu
    770                 775                 780
Glu Gln Leu Val Ser Asp Asp Gly Ile Tyr Lys Glu Gln Val Leu Ala
785                 790                 795                 800
Lys Arg Leu Thr Met Leu Asp Phe Leu Glu Asp Tyr Pro Ala Cys Glu
                805                 810                 815
Met Pro Phe Glu Arg Phe Leu Ala Leu Leu Pro Ser Leu Lys Pro Arg
            820                 825                 830
Tyr Tyr Ser Ile Ser Ser Ser Pro Lys Val His Ala Asn Ile Val Ser
        835                 840                 845
Met Thr Val Gly Val Val Lys Ala Ser Ala Trp Ser Gly Arg Gly Glu
    850                 855                 860
Tyr Arg Gly Val Ala Ser Asn Tyr Leu Ala Glu Leu Asn Thr Gly Asp
865                 870                 875                 880
Ala Ala Ala Cys Phe Ile Arg Thr Pro Gln Ser Gly Phe Gln Met Pro
                885                 890                 895
Asn Asp Pro Glu Thr Pro Met Ile Met Val Gly Pro Gly Thr Gly Ile
            900                 905                 910
Ala Pro Phe Arg Gly Phe Ile Gln Ala Arg Ser Val Leu Lys Lys Glu
        915                 920                 925
```

```
Gly Ser Thr Leu Gly Glu Ala Leu Leu Tyr Phe Gly Cys Arg Arg Pro
    930                 935                 940

Asp His Asp Asp Leu Tyr Arg Glu Glu Leu Asp Gln Ala Glu Gln Asp
945                 950                 955                 960

Gly Leu Val Thr Ile Arg Arg Cys Tyr Ser Arg Val Glu Asn Glu Pro
                965                 970                 975

Lys Gly Tyr Val Gln His Leu Leu Lys Gln Asp Thr Gln Lys Leu Met
                980                 985                 990

Thr Leu Ile Glu Lys Gly Ala His Ile Tyr Val Cys Gly Asp Gly Ser
            995                1000                1005

Gln Met Ala Pro Asp Val Glu Arg Thr Leu Arg Leu Ala Tyr Glu
    1010                1015                1020

Ala Glu Lys Ala Ala Ser Gln Glu Glu Ser Ala Val Trp Leu Gln
    1025                1030                1035

Lys Leu Gln Asp Gln Arg Arg Tyr Val Lys Asp Val Trp Thr Gly
    1040                1045                1050

Met

<210> SEQ ID NO 6
<211> LENGTH: 1061
<212> TYPE: PRT
<213> ORGANISM: Bacillus subtilis GenBank / O08394

<400> SEQUENCE: 6

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
                20                  25                  30

Lys Leu Ala Glu Glu Gln Gly Pro Ile Phe Gln Ile His Thr Pro Ala
                35                  40                  45

Gly Thr Thr Ile Val Val Ser Gly His Glu Leu Val Lys Glu Val Cys
            50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Phe Thr Ser Trp Thr His Glu Pro
                85                  90                  95

Asn Trp Arg Lys Ala His Asn Ile Leu Met Pro Thr Phe Ser Gln Arg
                100                 105                 110

Ala Met Lys Asp Tyr His Glu Lys Met Val Asp Ile Ala Val Gln Leu
            115                 120                 125

Ile Gln Lys Trp Ala Arg Leu Asn Pro Asn Glu Ala Val Asp Val Pro
        130                 135                 140

Gly Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
                180                 185                 190

Leu Asp Val Gln Asp Lys Leu Met Val Arg Thr Lys Arg Gln Phe Arg
            195                 200                 205

Tyr Asp Ile Gln Thr Met Phe Ser Leu Val Asp Ser Ile Ile Ala Glu
        210                 215                 220

Arg Arg Ala Asn Gly Asp Gln Asp Glu Lys Asp Leu Leu Ala Arg Met
225                 230                 235                 240
```

```
Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Thr Tyr Phe Leu Leu Lys His Pro Asp
        275                 280                 285

Lys Leu Lys Lys Ala Tyr Glu Glu Val Asp Arg Val Leu Thr Asp Ala
    290                 295                 300

Ala Pro Thr Tyr Lys Gln Val Leu Glu Leu Thr Tyr Ile Arg Met Ile
305                 310                 315                 320

Leu Asn Glu Ser Leu Arg Leu Trp Pro Thr Ala Pro Ala Phe Ser Leu
                325                 330                 335

Tyr Pro Lys Glu Asp Thr Val Ile Gly Gly Lys Phe Pro Ile Thr Thr
            340                 345                 350

Asn Asp Arg Ile Ser Val Leu Ile Pro Gln Leu His Arg Asp Arg Asp
        355                 360                 365

Ala Trp Gly Lys Asp Ala Glu Glu Phe Arg Pro Glu Arg Phe Glu His
    370                 375                 380

Gln Asp Gln Val Pro His His Ala Tyr Lys Pro Phe Gly Asn Gly Gln
385                 390                 395                 400

Arg Ala Cys Ile Gly Met Gln Phe Ala Leu His Glu Ala Thr Leu Val
                405                 410                 415

Leu Gly Met Ile Leu Lys Tyr Phe Thr Leu Ile Asp His Glu Asn Tyr
            420                 425                 430

Glu Leu Asp Ile Lys Gln Thr Leu Thr Leu Lys Pro Gly Asp Phe His
        435                 440                 445

Ile Ser Val Gln Ser Arg His Gln Glu Ala Ile His Ala Asp Val Gln
    450                 455                 460

Ala Ala Glu Lys Ala Ala Pro Asp Glu Gln Lys Glu Lys Thr Glu Ala
465                 470                 475                 480

Lys Gly Ala Ser Val Ile Gly Leu Asn Asn Arg Pro Leu Leu Val Leu
                485                 490                 495

Tyr Gly Ser Asp Thr Gly Thr Ala Glu Gly Val Ala Arg Glu Leu Ala
            500                 505                 510

Asp Thr Ala Ser Leu His Gly Val Arg Thr Lys Thr Ala Pro Leu Asn
        515                 520                 525

Asp Arg Ile Gly Lys Leu Pro Lys Glu Gly Ala Val Val Ile Val Thr
    530                 535                 540

Ser Ser Tyr Asn Gly Lys Pro Pro Ser Asn Ala Gly Gln Phe Val Gln
545                 550                 555                 560

Trp Leu Gln Glu Ile Lys Pro Gly Glu Leu Glu Gly Val His Tyr Ala
                565                 570                 575

Val Phe Gly Cys Gly Asp His Asn Trp Ala Ser Thr Tyr Gln Tyr Val
            580                 585                 590

Pro Arg Phe Ile Asp Glu Gln Leu Ala Glu Lys Gly Ala Thr Arg Phe
        595                 600                 605

Ser Ala Arg Gly Glu Gly Asp Val Ser Gly Asp Phe Glu Gly Gln Leu
    610                 615                 620

Asp Glu Trp Lys Lys Ser Met Trp Ala Asp Ala Ile Lys Ala Phe Gly
625                 630                 635                 640

Leu Glu Leu Asn Glu Asn Ala Asp Lys Glu Arg Ser Thr Leu Ser Leu
                645                 650                 655

Gln Phe Val Arg Gly Leu Gly Glu Ser Pro Leu Ala Arg Ser Tyr Glu
```

-continued

```
                660                 665                 670
Ala Ser His Ala Ser Ile Ala Glu Asn Arg Glu Leu Gln Ser Ala Asp
            675                 680                 685

Ser Asp Arg Ser Thr Arg His Ile Glu Ile Ala Leu Pro Pro Asp Val
        690                 695                 700

Glu Tyr Gln Glu Gly Asp His Leu Gly Val Leu Pro Lys Asn Ser Gln
705                 710                 715                 720

Thr Asn Val Ser Arg Ile Leu His Arg Phe Gly Leu Lys Gly Thr Asp
                725                 730                 735

Gln Val Thr Leu Ser Ala Ser Gly Arg Ser Ala Gly His Leu Pro Leu
            740                 745                 750

Gly Arg Pro Val Ser Leu His Asp Leu Leu Ser Tyr Ser Val Glu Val
        755                 760                 765

Gln Glu Ala Ala Thr Arg Ala Gln Ile Arg Glu Leu Ala Ser Phe Thr
    770                 775                 780

Val Cys Pro Pro His Arg Arg Glu Leu Glu Leu Ser Ala Glu Gly
785                 790                 795                 800

Val Tyr Gln Glu Gln Ile Leu Lys Lys Arg Ile Ser Met Leu Asp Leu
                805                 810                 815

Leu Glu Lys Tyr Glu Ala Cys Asp Met Pro Phe Glu Arg Phe Leu Glu
            820                 825                 830

Leu Leu Arg Pro Leu Lys Pro Arg Tyr Tyr Ser Ile Ser Ser Ser Pro
        835                 840                 845

Arg Val Asn Pro Arg Gln Ala Ser Ile Thr Val Gly Val Val Arg Gly
    850                 855                 860

Pro Ala Trp Ser Gly Arg Gly Glu Tyr Arg Gly Val Ala Ser Asn Asp
865                 870                 875                 880

Leu Ala Glu Arg Gln Ala Gly Asp Asp Val Val Met Phe Ile Arg Thr
                885                 890                 895

Pro Glu Ser Arg Phe Gln Leu Pro Lys Asp Pro Glu Thr Pro Ile Ile
            900                 905                 910

Met Val Gly Pro Gly Thr Gly Val Ala Pro Phe Arg Gly Phe Leu Gln
        915                 920                 925

Ala Arg Asp Val Leu Lys Arg Glu Gly Lys Thr Leu Gly Glu Ala His
    930                 935                 940

Leu Tyr Phe Gly Cys Arg Asn Asp Arg Asp Phe Ile Tyr Arg Asp Glu
945                 950                 955                 960

Leu Glu Arg Phe Glu Lys Asp Gly Ile Val Thr Val His Thr Ala Phe
                965                 970                 975

Ser Arg Lys Glu Gly Met Pro Lys Thr Tyr Val Gln His Leu Met Ala
            980                 985                 990

Asp Gln Ala Asp Thr Leu Ile Ser  Ile Leu Asp Arg Gly  Gly Arg Leu
        995                 1000                 1005

Tyr Val  Cys Gly Asp Gly Ser  Lys Met Ala Pro Asp  Val Glu Ala
    1010                 1015                 1020

Ala Leu  Gln Lys Ala Tyr Gln  Ala Val His Gly Thr  Gly Glu Gln
    1025                 1030                 1035

Glu Ala  Gln Asn Trp Leu Arg  His Leu Gln Asp Thr  Gly Met Tyr
    1040                 1045                 1050

Ala Lys  Asp Val Trp Ala Gly  Ile
    1055                 1060
```

<210> SEQ ID NO 7

-continued

```
<211> LENGTH: 1061
<212> TYPE: PRT
<213> ORGANISM: Bacillus subtilis GenBank / D69799

<400> SEQUENCE: 7
```

Met Lys Glu Thr Ser Pro Ile Pro Gln Pro Lys Thr Phe Gly Pro Leu
1               5                   10                  15

Gly Asn Leu Pro Leu Ile Asp Lys Asp Lys Pro Thr Leu Ser Leu Ile
            20                  25                  30

Lys Leu Ala Glu Glu Gln Gly Pro Ile Phe Gln Ile His Thr Pro Ala
        35                  40                  45

Gly Thr Thr Ile Val Val Ser Gly His Glu Leu Val Lys Glu Val Cys
    50                  55                  60

Asp Glu Glu Arg Phe Asp Lys Ser Ile Glu Gly Ala Leu Glu Lys Val
65                  70                  75                  80

Arg Ala Phe Ser Gly Asp Gly Leu Phe Thr Ser Trp Thr His Glu Pro
                85                  90                  95

Asn Trp Arg Lys Ala His Asn Ile Leu Met Pro Thr Phe Ser Gln Arg
            100                 105                 110

Ala Met Lys Asp Tyr His Glu Lys Met Val Asp Ile Ala Val Gln Leu
        115                 120                 125

Ile Gln Lys Trp Ala Arg Leu Asn Pro Asn Glu Ala Val Asp Val Pro
    130                 135                 140

Gly Asp Met Thr Arg Leu Thr Leu Asp Thr Ile Gly Leu Cys Gly Phe
145                 150                 155                 160

Asn Tyr Arg Phe Asn Ser Tyr Tyr Arg Glu Thr Pro His Pro Phe Ile
                165                 170                 175

Asn Ser Met Val Arg Ala Leu Asp Glu Ala Met His Gln Met Gln Arg
            180                 185                 190

Leu Asp Val Gln Asp Lys Leu Met Val Arg Thr Lys Arg Gln Phe Arg
        195                 200                 205

Tyr Asp Ile Gln Thr Met Phe Ser Leu Val Asp Ser Ile Ile Ala Glu
    210                 215                 220

Arg Arg Ala Asn Gly Asp Gln Asp Glu Lys Asp Leu Leu Ala Arg Met
225                 230                 235                 240

Leu Asn Val Glu Asp Pro Glu Thr Gly Glu Lys Leu Asp Asp Glu Asn
                245                 250                 255

Ile Arg Phe Gln Ile Ile Thr Phe Leu Ile Ala Gly His Glu Thr Thr
            260                 265                 270

Ser Gly Leu Leu Ser Phe Ala Thr Tyr Phe Leu Leu Lys His Pro Asp
        275                 280                 285

Lys Leu Lys Lys Ala Tyr Glu Glu Val Asp Arg Val Leu Thr Asp Ala
    290                 295                 300

Ala Pro Thr Tyr Lys Gln Val Leu Glu Leu Thr Tyr Ile Arg Met Ile
305                 310                 315                 320

Leu Asn Glu Ser Leu Arg Leu Trp Pro Thr Ala Pro Ala Phe Ser Leu
                325                 330                 335

Tyr Pro Lys Glu Asp Thr Val Ile Gly Gly Lys Phe Pro Ile Thr Thr
            340                 345                 350

Asn Asp Arg Ile Ser Val Leu Ile Pro Gln Leu His Arg Asp Arg Asp
        355                 360                 365

Ala Trp Gly Lys Asp Ala Glu Glu Phe Arg Pro Glu Arg Phe Glu His
    370                 375                 380

Gln Asp Gln Val Pro His His Ala Tyr Lys Pro Phe Gly Asn Gly Gln

```
385                 390                 395                 400
Arg Ala Cys Ile Gly Met Gln Phe Ala Leu His Glu Ala Thr Leu Val
                405                 410                 415

Leu Gly Met Ile Leu Lys Tyr Phe Thr Leu Ile Asp His Glu Asn Tyr
            420                 425                 430

Glu Leu Asp Ile Lys Gln Thr Leu Thr Leu Lys Pro Gly Asp Phe His
            435                 440                 445

Ile Ser Val Gln Ser Arg His Gln Glu Ala Ile His Ala Asp Val Gln
        450                 455                 460

Ala Ala Glu Lys Ala Ala Pro Asp Glu Gln Lys Glu Lys Thr Glu Ala
465                 470                 475                 480

Lys Gly Ala Ser Val Ile Gly Leu Asn Asn Arg Pro Leu Leu Val Leu
                485                 490                 495

Tyr Gly Ser Asp Thr Gly Thr Ala Glu Gly Val Ala Arg Glu Leu Ala
            500                 505                 510

Asp Thr Ala Ser Leu His Gly Val Arg Thr Lys Thr Ala Pro Leu Asn
            515                 520                 525

Asp Arg Ile Gly Lys Leu Pro Lys Glu Gly Ala Val Val Ile Val Thr
        530                 535                 540

Ser Ser Tyr Asn Gly Lys Pro Pro Ser Asn Ala Gly Gln Phe Val Gln
545                 550                 555                 560

Trp Leu Gln Glu Ile Lys Pro Gly Glu Leu Glu Gly Val His Tyr Ala
                565                 570                 575

Val Phe Gly Cys Gly Asp His Asn Trp Ala Ser Thr Tyr Gln Tyr Val
            580                 585                 590

Pro Arg Phe Ile Asp Glu Gln Leu Ala Glu Lys Gly Ala Thr Arg Phe
            595                 600                 605

Ser Ala Arg Gly Glu Gly Asp Val Ser Gly Asp Phe Glu Gly Gln Leu
        610                 615                 620

Asp Glu Trp Lys Lys Ser Met Trp Ala Asp Ala Ile Lys Ala Phe Gly
625                 630                 635                 640

Leu Glu Leu Asn Glu Asn Ala Asp Lys Glu Arg Ser Thr Leu Ser Leu
                645                 650                 655

Gln Phe Val Arg Gly Leu Gly Glu Ser Pro Leu Ala Arg Ser Tyr Glu
            660                 665                 670

Ala Ser His Ala Ser Ile Ala Glu Asn Arg Glu Leu Gln Ser Ala Asp
            675                 680                 685

Ser Asp Arg Ser Thr Arg His Ile Glu Ile Ala Leu Pro Pro Asp Val
        690                 695                 700

Glu Tyr Gln Glu Gly Asp His Leu Gly Val Leu Pro Lys Asn Ser Gln
705                 710                 715                 720

Thr Asn Val Ser Arg Ile Leu His Arg Phe Gly Leu Lys Gly Thr Asp
                725                 730                 735

Gln Val Thr Leu Ser Ala Ser Gly Arg Ser Ala Gly His Leu Pro Leu
            740                 745                 750

Gly Arg Pro Val Ser Leu His Asp Leu Leu Ser Tyr Ser Val Glu Val
            755                 760                 765

Gln Glu Ala Ala Thr Arg Ala Gln Ile Arg Glu Leu Ala Ser Phe Thr
        770                 775                 780

Val Cys Pro Pro His Arg Arg Glu Leu Glu Glu Leu Ser Ala Glu Gly
785                 790                 795                 800

Val Tyr Gln Glu Gln Ile Leu Lys Lys Arg Ile Ser Met Leu Asp Leu
                805                 810                 815
```

```
Leu Glu Lys Tyr Glu Ala Cys Asp Met Pro Phe Glu Arg Phe Leu Glu
            820                 825                 830
Leu Leu Arg Pro Leu Lys Pro Arg Tyr Tyr Ser Ile Ser Ser Ser Pro
            835                 840                 845
Arg Val Asn Pro Arg Gln Ala Ser Ile Thr Val Gly Val Val Arg Gly
            850                 855                 860
Pro Ala Trp Ser Gly Arg Gly Glu Tyr Arg Gly Val Ala Ser Asn Asp
865                 870                 875                 880
Leu Ala Glu Arg Gln Ala Gly Asp Asp Val Val Met Phe Ile Arg Thr
                    885                 890                 895
Pro Glu Ser Arg Phe Gln Leu Pro Lys Asp Pro Glu Thr Pro Ile Ile
            900                 905                 910
Met Val Gly Pro Gly Thr Gly Val Ala Pro Phe Arg Gly Phe Leu Gln
            915                 920                 925
Ala Arg Asp Val Leu Lys Arg Glu Gly Lys Thr Leu Gly Glu Ala His
            930                 935                 940
Leu Tyr Phe Gly Cys Arg Asn Asp Arg Asp Phe Ile Tyr Arg Asp Glu
945                 950                 955                 960
Leu Glu Arg Phe Glu Lys Asp Gly Ile Val Thr Val His Thr Ala Phe
                965                 970                 975
Ser Arg Lys Glu Gly Met Pro Lys Thr Tyr Val Gln His Leu Met Ala
            980                 985                 990
Asp Gln Ala Asp Thr Leu Ile Ser  Ile Leu Asp Arg Gly  Gly Arg Leu
            995                 1000                1005
Tyr Val  Cys Gly Asp Gly Ser  Lys Met Ala Pro Asp  Val Glu Ala
     1010                1015                1020
Ala Leu  Gln Lys Ala Tyr Gln  Ala Val His Gly Thr  Gly Glu Gln
     1025                1030                1035
Glu Ala  Gln Asn Trp Leu Arg  His Leu Gln Asp Thr  Gly Met Tyr
     1040                1045                1050
Ala Lys  Asp Val Trp Ala Gly  Ile
     1055                1060

<210> SEQ ID NO 8
<211> LENGTH: 527
<212> TYPE: PRT
<213> ORGANISM: Streptomyces coelicolor GenBank / CAB66201

<400> SEQUENCE: 8

Met Ala Gln Thr Ala Arg Glu Pro Ala Arg Asp Gly Leu Pro Lys Gly
1               5                   10                  15
Phe Arg Ser Ala Glu Leu Gly Trp Pro Glu Leu His Arg Ile Pro His
            20                  25                  30
Pro Pro Tyr Arg Leu Pro Leu Leu Gly Asp Val Val Gly Ala Ser Arg
            35                  40                  45
Arg Thr Pro Met Gln Asp Ser Leu Arg Tyr Ala Arg Arg Leu Gly Pro
        50                  55                  60
Ile Phe Arg Arg Arg Ala Phe Gly Lys Glu Val Phe Val Trp Gly
65                  70                  75                  80
Ala Ala Leu Ala Ala Asp Leu Ala Asp Glu Ala Arg Phe Ala Lys His
                85                  90                  95
Val Gly Leu Gly Val Ala Asn Leu Arg Pro Val Ala Gly Asp Gly Leu
            100                 105                 110
Phe Thr Ala Tyr Asn His Glu Pro Asn Trp Gln Leu Ala His Asp Val
```

-continued

```
                115                 120                 125
Leu Ala Pro Gly Phe Ser Arg Glu Ala Met Ala Gly Tyr His Val Met
    130                 135                 140
Met Leu Asp Val Ala Ala Arg Leu Thr Gly His Trp Asp Leu Ala Glu
145                 150                 155                 160
Ala Ser Gly Arg Ala Val Asp Val Pro Gly Asp Met Thr Lys Leu Thr
                165                 170                 175
Leu Glu Thr Ile Ala Arg Thr Gly Phe Gly His Asp Phe Gly Ser Phe
            180                 185                 190
Glu Arg Ser Arg Leu His Pro Phe Val Thr Ala Met Val Gly Thr Leu
        195                 200                 205
Gly Tyr Ala Gln Arg Leu Asn Thr Val Pro Ala Pro Leu Ala Pro Trp
    210                 215                 220
Leu Leu Arg Asp Ala Ser Arg Arg Asn Ala Ala Asp Ile Ala His Leu
225                 230                 235                 240
Asn Arg Thr Val Asp Asp Leu Val Arg Glu Arg Ala Asn Gly Gly
                245                 250                 255
Thr Gly Gly Gly Thr Gly Ser Gly Ser Gly Ser Gly Asp Leu Leu Asp
                260                 265                 270
Arg Met Leu Glu Thr Ala His Pro Arg Thr Gly Glu Arg Leu Ser Pro
        275                 280                 285
Gln Asn Val Arg Arg Gln Val Ile Thr Phe Leu Val Ala Gly His Glu
    290                 295                 300
Thr Thr Ser Gly Ala Leu Ser Phe Ala Leu His Tyr Leu Ala Gln His
305                 310                 315                 320
Pro Asp Val Ala Ala Arg Ala Arg Ala Glu Val Asp Arg Val Trp Gly
                325                 330                 335
Asp Thr Glu Ala Pro Gly Tyr Glu Gln Val Ala Lys Leu Arg Tyr Val
            340                 345                 350
Arg Arg Val Leu Asp Glu Ser Leu Arg Leu Trp Pro Thr Ala Pro Gly
        355                 360                 365
Phe Ala Arg Glu Ala Arg Glu Asp Thr Val Leu Gly Gly Thr His Pro
    370                 375                 380
Met Arg Arg Gly Ala Trp Ala Leu Val Leu Thr Gly Met Leu His Arg
385                 390                 395                 400
Asp Pro Glu Val Trp Gly Ala Asp Ala Glu Arg Phe Asp Pro Asp Arg
                405                 410                 415
Phe Asp Ala Lys Ala Val Arg Ser Arg Ala Pro His Thr Phe Lys Pro
            420                 425                 430
Phe Gly Thr Gly Ala Arg Ala Cys Ile Gly Arg Gln Phe Ala Leu His
        435                 440                 445
Glu Ala Thr Leu Val Leu Gly Leu Leu Leu Arg Tyr Glu Leu Arg
    450                 455                 460
Pro Glu Pro Gly Tyr Arg Leu Arg Val Thr Glu Arg Leu Thr Leu Met
465                 470                 475                 480
Pro Glu Gly Leu Arg Leu His Leu Val Arg Arg Thr Ala Ala Pro
                485                 490                 495
Ala Pro Gly Arg Arg Thr Ala Pro Gly Ala Ala Asp Asp Ala Gly
            500                 505                 510
Asp Thr Val Ser Ala Pro Gly Cys Pro Val His Arg Ala Gly Asp
        515                 520                 525

<210> SEQ ID NO 9
```

<211> LENGTH: 1066
<212> TYPE: PRT
<213> ORGANISM: Fusarium oxysporum GenBank / BAA82526

<400> SEQUENCE: 9

```
Met Ala Glu Ser Val Pro Ile Pro Glu Pro Gly Tyr Pro Leu Ile
1               5                   10                  15

Gly Asn Leu Gly Glu Phe Thr Ser Asn Pro Leu Ser Asp Leu Asn Arg
            20                  25                  30

Leu Ala Asp Thr Tyr Gly Pro Ile Phe Arg Leu Arg Leu Gly Ala Lys
                35                  40                  45

Ala Pro Ile Phe Val Ser Ser Asn Ser Leu Ile Asn Glu Val Cys Asp
    50                  55                  60

Glu Lys Arg Phe Lys Lys Thr Leu Lys Ser Val Leu Ser Gln Val Arg
65                  70                  75                  80

Glu Gly Val His Asp Gly Leu Phe Thr Ala Phe Glu Asp Glu Pro Asn
                85                  90                  95

Trp Gly Lys Ala His Arg Ile Leu Val Pro Ala Phe Gly Pro Leu Ser
            100                 105                 110

Ile Arg Gly Met Phe Pro Glu Met His Asp Ile Ala Thr Gln Leu Cys
                115                 120                 125

Met Lys Phe Ala Arg His Gly Pro Arg Thr Pro Ile Asp Thr Ser Asp
    130                 135                 140

Asn Phe Thr Arg Leu Ala Leu Asp Thr Leu Ala Leu Cys Ala Met Asp
145                 150                 155                 160

Phe Arg Phe Tyr Ser Tyr Tyr Lys Glu Glu Leu His Pro Phe Ile Glu
                165                 170                 175

Ala Met Gly Asp Phe Leu Thr Glu Ser Gly Asn Arg Asn Arg Arg Pro
            180                 185                 190

Pro Phe Ala Pro Asn Phe Leu Tyr Arg Ala Ala Asn Glu Lys Phe Tyr
                195                 200                 205

Gly Asp Ile Ala Leu Met Lys Ser Val Ala Asp Glu Val Val Ala Ala
    210                 215                 220

Arg Lys Ala Ser Pro Ser Asp Arg Lys Asp Leu Leu Ala Ala Met Leu
225                 230                 235                 240

Asn Gly Val Asp Pro Gln Thr Gly Glu Lys Leu Ser Asp Glu Asn Ile
                245                 250                 255

Thr Asn Gln Leu Ile Thr Phe Leu Ile Ala Gly His Glu Thr Thr Ser
            260                 265                 270

Gly Thr Leu Ser Phe Ala Met Tyr Gln Leu Leu Lys Asn Pro Glu Ala
                275                 280                 285

Tyr Ser Lys Val Gln Lys Glu Val Asp Glu Val Val Gly Arg Gly Pro
    290                 295                 300

Val Leu Val Glu His Leu Thr Lys Leu Pro Tyr Ile Ser Ala Val Leu
305                 310                 315                 320

Arg Glu Thr Leu Arg Leu Asn Ser Pro Ile Thr Ala Phe Gly Leu Glu
                325                 330                 335

Ala Ile Asp Asp Thr Phe Leu Gly Gly Lys Tyr Leu Val Lys Lys Gly
            340                 345                 350

Glu Ile Val Thr Ala Leu Leu Ser Arg Gly His Val Asp Pro Val Val
                355                 360                 365

Tyr Gly Asn Asp Ala Asp Lys Phe Ile Pro Glu Arg Met Leu Asp Asp
    370                 375                 380

Glu Phe Ala Arg Leu Asn Lys Glu Tyr Pro Asn Cys Trp Lys Pro Phe
```

-continued

```
            385                 390                 395                 400
Gly Asn Gly Lys Arg Ala Cys Ile Gly Arg Pro Phe Ala Trp Gln Glu
                405                 410                 415

Ser Leu Leu Ala Met Val Val Leu Phe Gln Asn Phe Asn Phe Thr Met
                420                 425                 430

Thr Asp Pro Asn Tyr Ala Leu Glu Ile Lys Gln Thr Leu Thr Ile Lys
                435                 440                 445

Pro Asp His Phe Tyr Ile Asn Ala Thr Leu Arg His Gly Met Thr Pro
                450                 455                 460

Thr Glu Leu Glu His Val Leu Ala Gly Asn Gly Ala Thr Ser Ser Ser
465                 470                 475                 480

Thr His Asn Ile Lys Ala Ala Ala Asn Leu Asp Ala Lys Ala Gly Ser
                485                 490                 495

Gly Lys Pro Met Ala Ile Phe Tyr Gly Ser Asn Ser Gly Thr Cys Glu
                500                 505                 510

Ala Leu Ala Asn Arg Leu Ala Ser Asp Ala Pro Ser His Gly Phe Ser
                515                 520                 525

Ala Thr Thr Val Gly Pro Leu Asp Gln Ala Lys Gln Asn Leu Pro Glu
                530                 535                 540

Asp Arg Pro Val Val Ile Val Thr Ala Ser Tyr Glu Gly Gln Pro Pro
545                 550                 555                 560

Ser Asn Ala Ala His Phe Ile Lys Trp Met Glu Asp Leu Asp Gly Asn
                565                 570                 575

Asp Met Glu Lys Val Ser Tyr Ala Val Phe Ala Cys Gly His His Asp
                580                 585                 590

Trp Val Glu Thr Phe His Arg Ile Pro Lys Leu Val Asp Ser Thr Leu
                595                 600                 605

Glu Lys Arg Gly Gly Thr Arg Leu Val Pro Met Gly Ser Ala Asp Ala
                610                 615                 620

Ala Thr Ser Asp Met Phe Ser Asp Phe Glu Ala Trp Glu Asp Ile Val
625                 630                 635                 640

Leu Trp Pro Gly Leu Lys Glu Lys Tyr Lys Ile Ser Asp Glu Glu Ser
                645                 650                 655

Gly Gly Gln Lys Gly Leu Leu Val Glu Val Ser Thr Pro Arg Lys Thr
                660                 665                 670

Ser Leu Arg Gln Asp Val Glu Glu Ala Leu Val Val Ala Glu Lys Thr
                675                 680                 685

Leu Thr Lys Ser Gly Pro Ala Lys Lys His Ile Glu Ile Gln Leu Pro
                690                 695                 700

Ser Ala Met Thr Tyr Lys Ala Gly Asp Tyr Leu Ala Ile Leu Pro Leu
705                 710                 715                 720

Asn Pro Lys Ser Thr Val Ala Arg Val Phe Arg Arg Phe Ser Leu Ala
                725                 730                 735

Trp Asp Ser Phe Leu Lys Ile Gln Ser Glu Gly Pro Thr Thr Leu Pro
                740                 745                 750

Thr Asn Val Ala Ile Ser Ala Phe Asp Val Phe Ser Ala Tyr Val Glu
                755                 760                 765

Leu Ser Gln Pro Ala Thr Lys Arg Asn Ile Leu Ala Leu Ala Glu Ala
                770                 775                 780

Thr Glu Asp Lys Asp Thr Ile Gln Glu Leu Glu Arg Leu Ala Gly Asp
785                 790                 795                 800

Ala Tyr Gln Ala Glu Ile Ser Pro Lys Arg Val Ser Val Leu Asp Leu
                805                 810                 815
```

```
Leu Glu Lys Phe Pro Ala Val Ala Leu Pro Ile Ser Ser Tyr Leu Ala
            820                 825                 830

Met Leu Pro Pro Met Arg Val Arg Gln Tyr Ser Ile Ser Ser Ser Pro
            835                 840                 845

Phe Ala Asp Pro Ser Lys Leu Thr Leu Thr Tyr Ser Leu Leu Asp Ala
            850                 855                 860

Pro Ser Leu Ser Gly Gln Gly Arg His Val Gly Val Ala Thr Asn Phe
865                 870                 875                 880

Leu Ser His Leu Thr Ala Gly Asp Lys Leu His Val Ser Val Arg Ala
                885                 890                 895

Ser Ser Glu Ala Phe His Leu Pro Ser Asp Ala Glu Lys Thr Pro Ile
                900                 905                 910

Ile Cys Val Ala Ala Gly Thr Gly Leu Ala Pro Leu Arg Gly Phe Ile
                915                 920                 925

Gln Glu Arg Ala Ala Met Leu Ala Ala Gly Arg Thr Leu Ala Pro Ala
            930                 935                 940

Leu Leu Phe Phe Gly Cys Arg Asn Pro Glu Ile Asp Asp Leu Tyr Ala
945                 950                 955                 960

Glu Glu Phe Glu Arg Trp Glu Lys Met Gly Ala Val Asp Val Arg Arg
                965                 970                 975

Ala Tyr Ser Arg Ala Thr Asp Lys Ser Glu Gly Cys Lys Tyr Val Gln
                980                 985                 990

Asp Arg Val Tyr His Asp Arg Ala Asp Val Phe Lys Val Trp Asp Gln
                995                 1000                1005

Gly Ala  Lys Val Phe Ile Cys  Gly Ser Arg Glu Ile  Gly Lys Ala
         1010                 1015                 1020

Val Glu  Asp Val Cys Val Arg  Leu Ala Ile Glu Lys  Ala Gln Gln
         1025                 1030                 1035

Asn Gly  Arg Asp Val Thr Glu  Glu Met Ala Arg Ala  Trp Phe Glu
         1040                 1045                 1050

Arg Ser  Arg Asn Glu Arg Phe  Ala Thr Asp Val Phe  Asp
         1055                 1060                 1065

<210> SEQ ID NO 10
<211> LENGTH: 1115
<212> TYPE: PRT
<213> ORGANISM: Gibberella moniliformis GenBank / AAG27132

<400> SEQUENCE: 10

Met Ser Ala Thr Ala Leu Phe Thr Arg Arg Ser Val Ser Thr Ser Asn
1               5                   10                  15

Pro Glu Leu Arg Pro Ile Pro Gly Pro Lys Pro Leu Pro Leu Leu Gly
            20                  25                  30

Asn Leu Phe Asp Phe Asp Phe Asp Asn Leu Thr Lys Ser Leu Gly Glu
        35                  40                  45

Leu Gly Lys Ile His Gly Pro Ile Tyr Ser Ile Thr Phe Gly Ala Ser
    50                  55                  60

Thr Glu Ile Met Val Thr Ser Arg Glu Ile Ala Gln Glu Leu Cys Asp
65                  70                  75                  80

Glu Thr Arg Phe Cys Lys Leu Pro Gly Gly Ala Leu Asp Val Met Lys
                85                  90                  95

Ala Val Val Gly Asp Gly Leu Phe Thr Ala Glu Thr Ser Asn Pro Lys
            100                 105                 110

Trp Ala Ile Ala His Arg Ile Ile Thr Pro Leu Phe Gly Ala Met Arg
```

```
                    115                 120                 125
Ile Arg Gly Met Phe Asp Asp Met Lys Asp Ile Cys Glu Gln Met Cys
    130                 135                 140

Leu Arg Trp Ala Arg Phe Gly Pro Asp Glu Pro Leu Asn Val Cys Asp
145                 150                 155                 160

Asn Met Thr Lys Leu Thr Leu Asp Thr Ile Ala Leu Cys Thr Ile Asp
                165                 170                 175

Tyr Arg Phe Asn Ser Phe Tyr Arg Glu Asn Gly Ala Ala His Pro Phe
                180                 185                 190

Ala Glu Ala Val Val Asp Val Met Thr Glu Ser Phe Asp Gln Ser Asn
                195                 200                 205

Leu Pro Asp Phe Val Asn Asn Tyr Val Arg Phe Arg Ala Met Ala Lys
    210                 215                 220

Phe Lys Arg Gln Ala Ala Glu Leu Arg Arg Gln Thr Glu Glu Leu Ile
225                 230                 235                 240

Ala Ala Arg Arg Gln Asn Pro Val Asp Arg Asp Asp Leu Leu Asn Ala
                245                 250                 255

Met Leu Ser Ala Lys Asp Pro Lys Thr Gly Glu Gly Leu Ser Pro Glu
            260                 265                 270

Ser Ile Val Asp Asn Leu Leu Thr Phe Leu Ile Ala Gly His Glu Thr
    275                 280                 285

Thr Ser Ser Leu Leu Ser Phe Cys Phe Tyr Tyr Leu Leu Glu Asn Pro
            290                 295                 300

His Val Leu Arg Arg Val Gln Gln Glu Val Asp Thr Val Val Gly Ser
305                 310                 315                 320

Asp Thr Ile Thr Val Asp His Leu Ser Ser Met Pro Tyr Leu Glu Ala
                325                 330                 335

Val Leu Arg Glu Thr Leu Arg Leu Arg Asp Pro Gly Pro Gly Phe Tyr
                340                 345                 350

Val Lys Pro Leu Lys Asp Glu Val Ala Gly Lys Tyr Ala Val Asn
                355                 360                 365

Lys Asp Gln Pro Leu Phe Ile Val Phe Asp Ser Val His Arg Asp Gln
    370                 375                 380

Ser Thr Tyr Gly Ala Asp Ala Asp Glu Phe Arg Pro Glu Arg Met Leu
385                 390                 395                 400

Lys Asp Gly Phe Asp Lys Leu Pro Pro Cys Ala Trp Lys Pro Phe Gly
                405                 410                 415

Asn Gly Val Arg Ala Cys Val Gly Arg Pro Phe Ala Met Gln Gln Ala
                420                 425                 430

Ile Leu Ala Val Ala Met Val Leu His Lys Phe Asp Leu Val Lys Asp
                435                 440                 445

Glu Ser Tyr Thr Leu Lys Tyr His Val Thr Met Thr Val Arg Pro Val
    450                 455                 460

Gly Phe Thr Met Lys Val Arg Leu Arg Gln Gly Gln Arg Ala Thr Asp
465                 470                 475                 480

Leu Ala Met Gly Leu His Arg Gly His Ser Gln Glu Ala Ser Ala Ala
                485                 490                 495

Ala Ser Pro Ser Arg Ala Ser Leu Lys Arg Leu Ser Ser Asp Val Asn
            500                 505                 510

Gly Asp Asp Thr Asp His Lys Ser Gln Ile Ala Val Leu Tyr Ala Ser
            515                 520                 525

Asn Ser Gly Ser Cys Glu Ala Leu Ala Tyr Arg Leu Ala Ala Glu Ala
    530                 535                 540
```

-continued

```
Thr Glu Arg Gly Phe Gly Ile Arg Ala Val Asp Val Asn Asn Ala
545                 550                 555                 560

Ile Asp Arg Ile Pro Val Gly Ser Pro Val Ile Leu Ile Thr Ala Ser
                565                 570                 575

Tyr Asn Gly Glu Pro Ala Asp Ala Gln Glu Phe Val Pro Trp Leu
                580                 585                 590

Lys Ser Leu Glu Ser Gly Arg Leu Asn Gly Val Lys Phe Ala Val Phe
                595                 600                 605

Gly Asn Gly His Arg Asp Trp Ala Asn Thr Leu Phe Ala Val Pro Arg
610                 615                 620

Leu Ile Asp Ser Glu Leu Ala Arg Cys Gly Ala Glu Arg Val Ser Leu
625                 630                 635                 640

Met Gly Val Ser Asp Thr Cys Asp Ser Ser Asp Pro Phe Ser Asp Phe
                645                 650                 655

Glu Arg Trp Ile Asp Glu Lys Leu Phe Pro Glu Leu Glu Thr Pro His
                660                 665                 670

Gly Pro Gly Gly Val Lys Asn Gly Asp Arg Ala Val Pro Arg Gln Glu
                675                 680                 685

Leu Gln Val Ser Leu Gly Gln Pro Arg Ile Thr Met Arg Lys Gly
690                 695                 700

Tyr Val Arg Ala Ile Val Thr Glu Ala Arg Ser Leu Ser Ser Pro Gly
705                 710                 715                 720

Val Pro Glu Lys Arg His Leu Glu Leu Leu Pro Lys Asp Phe Asn
                725                 730                 735

Tyr Lys Ala Gly Asp His Val Tyr Ile Leu Pro Arg Asn Ser Pro Arg
                740                 745                 750

Asp Val Val Arg Ala Leu Ser Tyr Phe Gly Leu Gly Glu Asp Thr Leu
                755                 760                 765

Ile Thr Ile Arg Asn Thr Ala Arg Lys Leu Ser Leu Gly Leu Pro Leu
770                 775                 780

Asp Thr Pro Ile Thr Ala Thr Asp Leu Leu Gly Ala Tyr Val Glu Leu
785                 790                 795                 800

Gly Arg Thr Ala Ser Leu Lys Asn Leu Trp Thr Leu Val Asp Ala Ala
                805                 810                 815

Gly His Gly Ser Arg Ala Ala Leu Leu Ser Leu Thr Glu Pro Glu Arg
                820                 825                 830

Phe Arg Ala Glu Val Gln Asp Arg His Val Ser Ile Leu Asp Leu Leu
                835                 840                 845

Glu Arg Phe Pro Asp Ile Asp Leu Ser Leu Ser Cys Phe Leu Pro Met
850                 855                 860

Leu Ala Gln Ile Arg Pro Arg Ala Tyr Ser Phe Ser Ser Ala Pro Asp
865                 870                 875                 880

Trp Lys Pro Gly His Ala Thr Leu Thr Tyr Thr Val Val Asp Phe Ala
                885                 890                 895

Thr Pro Ala Thr Gln Gly Ile Asn Gly Ser Ser Lys Ser Lys Ala Val
                900                 905                 910

Gly Asp Gly Thr Ala Val Val Gln Arg Gln Gly Leu Ala Ser Ser Tyr
                915                 920                 925

Leu Ser Ser Leu Gly Pro Gly Thr Ser Leu Tyr Val Ser Leu His Arg
930                 935                 940

Ala Ser Pro Tyr Phe Cys Leu Gln Lys Ser Thr Ser Leu Pro Val Ile
945                 950                 955                 960
```

-continued

```
Met Val Gly Ala Gly Thr Gly Leu Ala Pro Phe Arg Ala Phe Leu Gln
                965                 970                 975

Glu Arg Arg Met Ala Ala Glu Gly Ala Lys Gln Arg Phe Gly Pro Ala
                980                 985                 990

Leu Leu Phe Phe Gly Cys Arg Gly  Pro Arg Leu Asp Ser  Leu Tyr Ser
            995                 1000                1005

Val Glu  Leu Glu Ala Tyr Glu  Thr Ile Gly Leu Val  Gln Val Arg
    1010                 1015                1020

Arg Ala  Tyr Ser Arg Asp Pro  Ser Ala Gln Asp Ala  Gln Gly Cys
    1025                 1030                1035

Lys Tyr  Val Thr Asp Arg Leu  Gly Lys Cys Arg Asp  Glu Val Ala
    1040                 1045                1050

Arg Leu  Trp Met Asp Gly Ala  Gln Val Leu Val Cys  Gly Gly Lys
    1055                 1060                1065

Lys Met  Ala Asn Asp Val Leu  Glu Val Leu Gly Pro  Met Leu Leu
    1070                 1075                1080

Glu Ile  Asp Gln Lys Arg Gly  Glu Thr Thr Ala Lys  Thr Val Val
    1085                 1090                1095

Glu Trp  Arg Ala Arg Leu Asp  Lys Ser Arg Tyr Val  Glu Glu Val
    1100                 1105                1110

Tyr Val
    1115

<210> SEQ ID NO 11
<211> LENGTH: 32
<212> TYPE: DNA
<213> ORGANISM: Artificial sequence
<220> FEATURE:
<223> OTHER INFORMATION: Amplification primer

<400> SEQUENCE: 11
acaggatcca tcgatgctta ggaggtcata tg                                    32

<210> SEQ ID NO 12
<211> LENGTH: 25
<212> TYPE: DNA
<213> ORGANISM: Artificial sequence
<220> FEATURE:
<223> OTHER INFORMATION: Amplification primer

<400> SEQUENCE: 12
gctcatgttt gacagcttat catcg                                            25
```

THERMOSTABLE PEROXIDE-DRIVEN CYTOCHROME P450 OXYGENASE VARIANTS AND METHODS OF USE

BACKGROUND OF THE INVENTION

1. Field of the Invention

This invention relates to variants of cytochrome P450 oxygenases. Specifically, the invention relates to thermostable variants of cytochrome P450 oxygenases capable of improved peroxide-driven hydroxylation, and methods of making thermostable variants.

2. Background Information

One of the great challenges of contemporary catalysis is the controlled oxidation of hydrocarbons. Processes for controlled, stereo- and regioselective oxidation of hydrocarbon feed stocks to more valuable and useful products such as alcohols, ketones, acids, and peroxides would have a major impact on the chemical and pharmaceutical industries. However, selective oxyfunctionalization of hydrocarbons remains one of the great challenges for contemporary chemistry. Despite decades of effort, including recent advances, the insertion of oxygen into unactivated carbon-hydrogen bonds (hydroxylation) remains difficult to achieve with high selectivity and high yield. Many chemical methods for hydroxylation require severe conditions of temperature or pressure, and the reactions are prone to over-oxidation, producing a range of products, many of which are not desired.

Enzymes are an attractive alternative to chemical catalysts. In particular, mono-oxygenases have unique properties that distinguish them from most chemical catalysts. Most impressive is their ability to catalyze the specific hydroxylation of non-activated C—H, one of the most useful biotransformation reactions, which is often difficult to achieve by chemical means, especially in water, at room temperature and atmospheric pressure. These cofactor-dependent oxidative enzymes have multiple domains and function via complex electron transfer mechanisms to transport a reduction equivalent to the catalytic heme center.

Cytochrome P450 monooxygenases ("P450s") are a group of widely-distributed heme-containing enzymes that insert one oxygen atom from diatomic oxygen into a diverse range of hydrophobic substrates, often with high regio- and stereoselectivity. The second oxygen atom is reduced to $H_2O$. The active sites of all cytochrome P450s contain an iron protoporphyrin IX with cysteinate as the fifth ligand, and the final coordination site is left to bind and activate molecular oxygen. Their ability to catalyze these reactions with high specificity and selectivity makes P450s attractive catalysts for chemical synthesis and other applications, including oxidation chemistry, and for many of the P450-catalyzed reactions, no chemical catalysts come close in performance. These enzymes are able to selectively hydroxylate a wide range of compounds, including fatty acids, aromatic compounds, alkanes, alkenes, and natural products. Unfortunately, P450s are generally limited by low turnover rates, and they generally require an expensive cofactor, NADH or NADPH, and at least one electron transfer partner protein (reductase). Furthermore, the enzymes are large, complex, and expensive.

Wild-type P450s are in some cases capable of using peroxides as a source of oxygen and electrons via a peroxide "shunt" pathway, though the efficiency of this route is low. This secondary mechanism for substrate oxidation offers the opportunity to take advantage of P450 catalysis without the need for a cofactor, and eliminates the rate-limiting electron transfer step carried out by the reductase. However, low efficiency is a major limitation. Further, wild-type enzymes capable of peroxide-driven hydroxylation, such as chloroperoxidase (CPO) and CYP152B1 are generally limited in their substrate specificity to hydroxylation of activated C—H bond carbons, i.e., carbon atoms adjacent to a functional group such as an aromatic ring, a carbonyl group, a heteroatom, etc.

One particular P450 enzyme, cytochrome P450 BM-3 from *Bacillus megaterium* ("P450 BM-3"; EC 1.14.14.1) also known as CYP102, is a water-soluble, catalytically self-sufficient P450 containing a heme (monooxygenase/hydroxylase) domain which is 472 amino acids in length and a reductase domain that is 585 amino acids in length. The total length of the enzyme is 1048 amino acids. The heme domain is generally considered to end at position 472 and it is followed by a short linker before the reductase domain begins. Because of the presence of an independent reductase domain within the protein itself, P450 BM-3 does not require an additional or extraneous reductase for activity, but it does require an electron source, such as the cofactor nicotinamide adenine dinucleotide phosphate (NADPH). Nucleotide and amino acid sequences for P450 BM-3 are provided in FIGS. 1 and 2, respectively, which are the sequences for P450 BM-3 from the GenBank database, accession nos. J04832 (SEQ ID NO:1) and P14779 (SEQ ID NO:2), respectively.

P450 BM-3 hydroxylates fatty acids with a chain length between C12 and C18 at subterminal positions, and the regioselectivity of oxygen insertion depends on the chain length. The optimal chain length of saturated fatty acids for P450 BM-3 is 14-16 carbons. P450 BM-3 is also known to hydroxylate the corresponding fatty acid amides and alcohols and forms epoxides from unsaturated fatty acids. The minimum requirements for activity are substrate, diatomic oxygen, and the cofactor NADPH.

It has been demonstrated that ω-para-nitrophenoxycarboxylic acids (pNCAs) can be used as surrogate substrates for BM-3. When this substrate is hydroxylated at the ω position to produce ω-oxycarboxylic acid, the yellow chromophore p-nitrophenolate (pNP) is produced, allowing for easy detection of activity when screening mutant libraries.

Mutant P450 BM-3 enzymes with modified activity have now been reported in the literature. For example, an F87A mutant was found to display a higher activity for the 12-pNCA substrate, and, under NADPH-driven catalysis, resulted in complete terminal hydroxylation of 12-pNCA, whereas the wild-type enzyme stopped at about 33% conversion. It has also been reported that the F87A mutant has a higher stability in $H_2O_2$ solutions. (The convention in the art, which is adopted herein, is to refer to a mutant with reference to the native amino acid residue at a position in the sequence, followed by the amino acid at that position in the mutant, e.g., F87 refers to the phenylalanine at position 87 in the wild-type sequence, and F87A refers to the phenylalanine at position 87 in the wild-type sequence which has been changed to alanine in the variant. The numbering of the amino acid residues starts with the amino acid residue following the initial methionine residue). It has been shown that $H_2O_2$-driven hydroxylation to be much faster with the F87A mutation, as well as with an F87G mutation.

Powerful techniques for creating enzymes with modified or improved properties are now available, such as directed evolution (Arnold, 1998), in which iterative cycles of random mutagenesis, recombination and functional screening for improved enzymes accumulate the mutations that confer the desired properties. For example, mutants of cytochrome $P450_{cam}$ or P450 BM-3 that hydroxylate the activated C—H bonds of naphthalene or 12-pNCA substrate, respectively, in the absence of co-factors through the "peroxide-shunt" pathway, herein termed "peroxygenases," have been created and identified using such techniques. In addition, P450 BM-3 mutants that can hydroxylate a variety of nonnatural substrates, including octane, several aromatic compounds and heterocyclic compounds have been reported.

While the activity of enzymes has thus been improved and modified, a continuing problem is that enzymes are often poorly stable under conditions encountered during production, storage or use. For example, improving enzyme resistance to thermal denaturation has been a major focus of protein engineering efforts. Improved thermostability often correlates with longer shelf-life, longer life-time during use (even at low temperatures), and a higher temperature optimum for activity. Stabilizing the relatively unstable cytochrome P450 enzymes by protein engineering is a particularly challenging problem, however, partly because the P450s comprise multiple subunits and contain thermolabile co-factors. Two thermostable cytochrome P450s (CYP119 and CYP175A1) from thermophilic organisms have recently been described and their (heme domain) crystal structures determined. CYP119 exhibits a melting temperature of ~91° C. Aromatic stacking, salt-link networks and shortened loops are believed to help stabilize these enzymes. Unfortunately, the functions of these P450s are not known, and reported activities are low (e.g., 0.35 min$^{-1}$ in the NADH-driven hydroxylation of lauric acid. While the International Patent application published as WO 02/083868 found that the mutations M145A, L324I, I366V, and E442K in the P450 BM-3 heme domain promoted thermostability, the overall thermostability of the peroxygenase mutant was not higher than that of the wild-type heme domain.

Thus, there is a need in the art for useful oxidation catalysts which are stable and do not require expensive cofactors or coenzymes for efficient oxidation and for methods of preparing the same. This invention addresses these and other needs in the art.

SUMMARY OF THE INVENTION

The present invention is based, in part, on the discovery of P450 BM-3 mutations improving the thermostability of variants that have a significantly improved ability to use peroxide as an oxygen source.

Thus, the invention provides an isolated variant of a cytochrome P450 BM-3 comprising the amino acid sequence of SEQ ID NO:3, the variant comprising at least a first mutation in an amino acid residue selected from K9, I58, F87, E93, H100, F107, K113, A135, M145, 145A, A184, N186, D217, M237, E244, S274, L324, I366, K434, E442, and V446 of SEQ ID NO:3, and at least a second mutation in an amino acid residue selected from L52, S106, N239, and V340.

The invention also provides a method of thermostabilizing a variant of a wild-type cytochrome P450 oxygenase heme domain, the variant having a mutation in a first amino acid residue, the method comprising: preparing a protein library of variants of the parent having an additional mutation in a second amino acid residue, which second amino acid is located no more than 10 Ångströms from the first amino acid in the wild-type enzyme, and selecting any variant having a higher thermostability than the parent.

The invention also provides a variant of a wild-type cytochrome P450 oxygenase heme domain comprising a mutation in a first amino acid residue, which mutation promotes a higher ability to utilize peroxide as an oxygen source for oxidation of a substrate than the wild-type enzyme, and an additional mutation in a second amino acid residue, which second amino acid is located no more than 10 Ångströms from the first amino acid in the wild-type enzyme, which variant has a higher thermostability than the wild-type enzyme.

The above features and many other advantages of the invention will become better understood by reference to the following detailed description when taken in conjunction with the accompanying drawings.

BRIEF DESCRIPTION OF THE DRAWINGS

FIGS. 1A and 1B show the nucleic acid sequence of cytochrome P450 BM-3, GenBank Accession No. J04832 (SEQ ID NO:1).

FIG. 2 shows the amino acid sequence of cytochrome P450 BM-3, GenBank Accession No. P14779 (SEQ ID NO:2).

FIGS. 4A and 4B shows the Sequence alignments of P450 BM-3 heme domain with (SEQ ID NO:3) with the heme domain of exemplary P450 enzymes (SEQ ID NO:7, from amino acid 2 to 454; SEQ ID NO:4; SEQ ID NO:8, from amino acid 51 to 483; SEQ ID NO:9, from amino acid 7 to 456; and SEQ ID NO:10, from amino acid 19 to 474) listed in Table 2.

FIG. 7A to 7D shows the four residue positions where mutations acquired during directed evolution of thermostability (L52, S106, E442, and M145) lie adjacent to positions (in the heme domain structure) where mutations were previously acquired during evolution of peroxygenase activity.

DETAILED DESCRIPTION OF THE INVENTION

Figure 3:
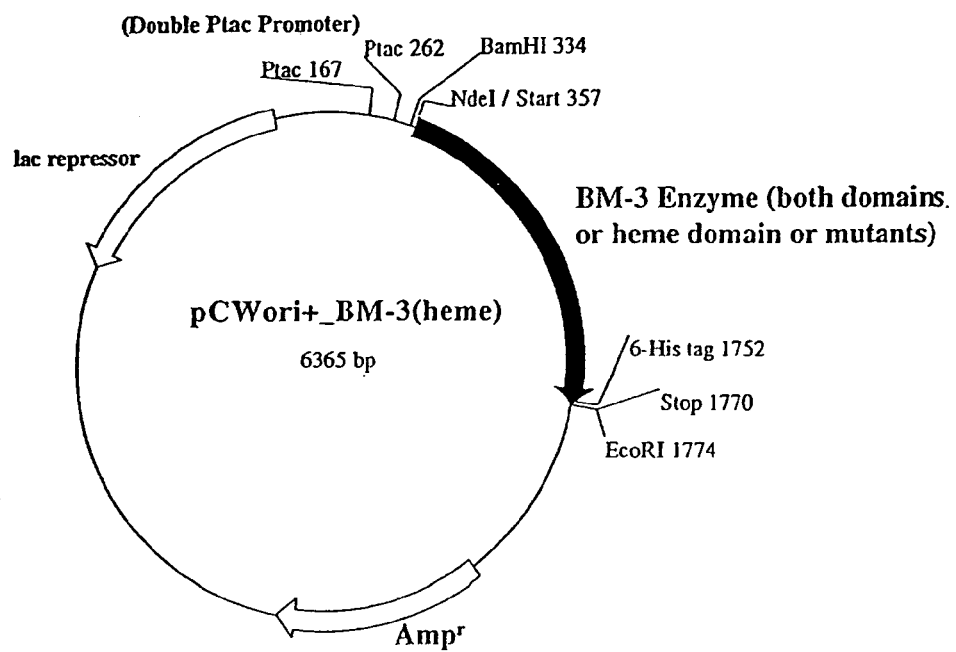
FIG. 3 shows the pCWori+ vector used for expression of, e.g., wild-type P450 BM-3, P450 variants, or heme domains of P450 variants.

Mutations in certain amino acid residues or regions of a P450 enzyme can, as shown herein, thermostabilize or stabilize an enzyme or enzyme mutant. In particular, peroxygenase variants according to the present invention are more stable or thermostable than previously described peroxygenase mutants, i.e., mutants of P450 enzymes more capable of using hydrogen peroxide for substrate oxidation than the corresponding wild-type enzyme. While many peroxygenase mutants previously known in the art can function efficiently without the reductase domain and are not dependent on cofactor, they have often suffered from a lower stability or thermostability than the wild-type enzyme. The present invention addresses this problem by providing P450 variants which retain or substantially retain the improved peroxide-driven activity of a peroxygenase mutant while preserving or improving thermostability as compared to the wild-type enzyme or corresponding region (e.g., heme domain) of the wild-type enzyme. For example, the 5H6 mutant described in Example 5 is more stable than the wild-type enzyme as well as the wild-type heme domain, and also has a many-fold higher peroxygenase activity over both the wild-type heme domain and the prior art mutant F87A.

Preferred mutation sites in the thermostable peroxygenase variants include those that correspond to L52, S106, A184, and V340 in the P450 BM-3 heme region (SEQ ID NO:3). For non-P450 BM-3 enzymes, the corresponding wild-type enzyme preferably has at least 30, 40, 50, 60, 70, 80, 85, 90, 95, 96, 97, 98, or 99% sequence identity to SEQ ID NO:3, and the mutated amino acid residues align with one or more of L52, S106, A184, and V340 in SEQ ID NO:3. In one embodiment, the amino acid substitutions at the respective sites are L521, S106R, A184V, and V340M. In another embodiment, the variant further comprises mutations in amino acid residues corresponding to I58, F87, H100, F107, A135, N239, S274, L324, I366, K434, E442, and V446. Preferably, the corresponding amino acid substitutions are I58V, F87A, H100R, F107L, A135S, N239H, S274T, L3241, I366V, K434E, E442K, and V4461. In yet another embodiment, the thermostable peroxygenase variant further comprises a deletion of a histidine residue in a C-terminal 6-residue His-tag. See, Tables 2A, 2B, and 3 below.

Also described herein is a method of thermostabilizing or stabilizing a P450 peroxygenase mutant, as well as thermostabilized or stabilized peroxygenase mutants. This method is based, in part, on the discovery that thermostabilizing mutations can be found in amino acid residues close to amino acid residues previously mutated to introduce peroxygenase activity. Preferably, the amino acids are adjacent; either in the amino acid sequence or in the 3-dimensional structure of the wild-type enzyme when folded, i.e., there is no other amino acid substantially in-between the two amino acid residues. In a preferred embodiment, in the wild-type enzyme, the amino acid in which the thermostabilizing mutation is introduced is within 15, preferably within 10, and most preferably within 7 Ångströms of the amino acid in which the peroxygenase mutation is introduced. Optimally, the two amino acid residues are within a 5-7 Ångström distance in the wild-type enzyme.

Exemplary pairs of adjacent amino acid residues include L52 and I58; S106 and F107; S274 and M145; and K434 and E442. (See FIG. 7). In an exemplary embodiment, a peroxygenase mutant comprising a mutation in an amino acid residue corresponding to at least one of I58, F107, S274, and K434 of SEQ ID NO:3 can be thermostabilized by introducing an additional mutation in the amino acid residue corresponding to L52, S106, M145, and E442, respectively. Preferably, the amino acid substitutions promoting peroxygenase activity correspond to one or more of I58V, F107L, S274T, and K434E, and the thermostabilizing amino acid substitutions preferably correspond to one or more of L521, S106R, M145A, and E442K.

Accordingly, a peroxygenase mutant of a wild-type enzyme can be stabilized or thermostabilized by creating a library of variants of the peroxygenase mutant having mutations in amino acid residues within 15, preferably 10, and more preferably within 7 Ångströms from a previously introduced mutation, and the resulting library screened for thermostability as described in the Examples. The order in which the peroxygenase and thermostabilizing mutation are introduced is not important. Thus, in an alternative embodiment, the thermostabilizing mutation can be introduced within 15, 10, or 7 Angstroms of a residue in which a mutation is known or believed to promote peroxygenase activity before the actual peroxygenase mutation is made. For example, a library of variants having a thermostabilizing mutation can be prepared in a first step, and the postulated peroxygenase mutation subsequently introduced into selected variants or the entire library. The library is then screened for peroxygenase activity and/or thermostability, preferably a thermostability or stability comparable or higher than that of the corresponding wild-type enzyme, and a higher peroxygenase activity than the corresponding wild-type enzyme.

The improved P450 BM-3 heme domain variants provided by the invention are useful for hydroxylation and other oxidation reactions on a variety of substrates, and in particular, substrates with alkyl chains, such as fatty acids, alkanes, long-chain alcohols and detergents. These BM3 catalyzed reactions can proceed without cofactor, in the presence of peroxide. The improved variants require lower concentrations of peroxide to achieve the same conversion, or require less time at a given peroxide concentration to achieve the same conversion than the wild-type heme domain. The use of a thermostable variant comprising the heme domain without the reductase domain allows more functional protein to be made per unit volume of fermentation and therefore improves the efficiency of enzyme production.

The use of P450 variants lacking the reductase provides important advantages during production of the catalyst (fermentation). In particular, the heme domain is not functional in the absence of its reductase or peroxide. The expression of functional cytochrome P450 can inhibit the growth of *E. coli* cells. Expression is also likely to have a deleterious effect on other host cells as well, limiting the ability of the cells to be used to produce large amounts of catalyst. It is therefore very beneficial to be able to make a variant lacking the reductase domain, because such a protein has no activity in the absence of peroxide, is not deleterious to the fermentation process and reduces the host cell toxicity, the reduced size of the protein and concomitant metabolic load for its production leads to higher expression in any organism, and the heme domain alone is more easily engineered to be stable, since only the heme domain and not the whole protein would have to be stabilized. The host cells can therefore be grown to high density and high P450 expression levels can be achieved.

Another major advantage of using a peroxygenase variant lacking the reductase domain is the lower susceptibility of the protein to damage by proteolysis (the linker between heme domain and reductase domain is known to be highly susceptible to proteolytic cleavage) and other denaturants. The significance of these features of the variants of the invention becomes evident during production and purification of the catalysts, as well as during its application, for example, in a washing machine or chemical reactor.

Applications for the variants of the present invention include their use as additives to a laundry detergent where the enzyme would serve to modify the properties of surfactants in the detergent by catalyzing a chemical reaction during the wash or rinse. Peroxide is often used in laundry applications, and it can be used to drive the P450-catalyzed reaction. The chemical reaction would alter the properties, e.g., solubility, of surfactants added to the detergent or of oily stains on clothing, making them easier to remove from the clothing. That the peroxide-dependent variant are also more stable or thermostable are especially advantageous for preparing enzymes less sensitive to long-term storage, and in such applications when elevated temperatures are desired. Enzymes which are stable at elevated temperatures typically have maximum activity at higher temperatures compared to less stable counterparts.

Another application for the variants of the present invention is in chemical synthesis. The heme domain mutants described here can be used with inexpensive peroxide to catalyze the same transformations as the holoenzyme with molecular oxygen and NADPH, and the synthesis can, if desired, be conducted at a higher temperature to increase the reaction rate, if needed. A suitable system for chemical synthesis would involve the slow addition of peroxide to a mixture containing enzyme and substrate, and allowing the chemical reaction to proceed at room temperature or higher. Organic solvents can be used to improve the solubility of the substrate in the reaction mixture.

A particular advantage of using the P450 BM-3 variants of the invention is that P450 BM-3 catalyzed oxidation is not restricted to activated C—H bond carbons, i.e., carbon atoms adjacent to electron-rich groups (aromatics, heteroatoms, carbonyl groups, etc.). For example, in fatty-acid oxidation, while a P450 enzyme, such as CYP152B1, is capable of peroxide-driven oxidation, it can only hydroxylate the alpha-carbon (the carbon adjacent to the acid carbonyl) (Matsunaga et al., 2000). Chloroperoxidase (CPO) is also capable of peroxide-driven hydroxylation on a variety of substrates, yet only at activated carbon positions (van Deurzen et al., 1997). The P450 BM-3 enzymes of the invention are capable of peroxide-driven hydroxylation of completely unactivated, carbon atoms in the substrate. In addition to having improved peroxide-driven hydroxylation activity, the P450 BM-3 variants described in the invention also demonstrate improved peroxide-driven epoxidation activity, such as in the epoxidation of styrene to styrene oxide.

In all of the possible applications, the peroxide-driven chemistry offers significant safety advantages over using molecular oxygen. Peroxide is comparatively inexpensive, is available in concentrated form, and does not pose the explosion hazard of enriched oxygen in industrial settings. This is particularly important when the substrate is flammable or explosive, such as propane or alkenes in general.

The following defined terms are used throughout the present specification, and should be helpful in understanding the scope and practice of the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

"Cytochrome P450 monooxygenase" or "P450 enzyme" means an enzyme in the superfamily of P450 haem-thiolate proteins, which are widely distributed in bacteria, fungi, plants and animals. The enzymes are involved in metabolism of a plethora of both exogenous and endogenous compounds. Usually, they act as terminal oxidases in multicomponent electron transfer chains, called here P450-containing monooxygenase systems. The unique feature which defines whether an enzyme is a cytochrome P450 enzyme is traditionally considered to be the characteristic absorption maximum ("Soret band") near 450 nm observed upon binding of carbon monoxide (CO) to the reduced form of the heme iron of the enzyme. Reactions catalyzed by cytochrome P450 enzymes include epoxidation, N-dealkylation, O-dealkylation, S-oxidation and hydroxylation. The most common reaction catalyzed by P450 enzymes is the monooxygenase reaction, i.e., insertion of one atom of oxygen into a substrate while the other oxygen atom is reduced to water.

"Heme domain" refers to an amino acid sequence within an oxygen carrier protein, which sequence is capable of binding an iron-complexing structure such as a porphyrin. Compounds of iron are typically complexed in a porphyrin (tetrapyrrole) ring that may differ in side chain composition. Heme groups can be the prosthetic groups of cytochromes and are found in most oxygen carrier proteins. Exemplary heme domains include that of P450 BM-3 ($P450_{BM-P}$), SEQ ID NO:3, as well as truncated or mutated versions of these that retain the capability to bind the iron-complexing structure. The skilled artisan can readily identify the heme domain of a specific protein using methods known in the art.

An "oxidation", "oxidation reaction", or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it loses electrons. A compound is "reduced" when it gains electrons. An oxidation reaction can also be called an "electron transfer reaction" and encompass the loss or gain of electrons or protons from a substance. Non-limiting examples of oxidation reactions include hydroxylation (e.g., $RH+O_2+2H^++2e^-$? $ROH+H_2O$) and epoxidation (alkene+$2H^++2e^-\rightarrow$epoxyalkene+$H_2O$).

A "peroxygenase" is an enzyme capable of functioning as an $H_2O_2$-driven hydroxylase, i.e., inserting an oxygen from the peroxide into its substrate. Peroxygenase reactions include, but are not limited to, hydroxylation and epoxidation. In the case of many P450 enzymes, a "peroxygenase" can be a heme domain operating via the peroxide shunt pathway, using $H_2O_2$ or another peroxide as an oxygen source, in the absence of NADPH or other co-factor and/or a reductase domain. A "peroxygenase mutant" or "peroxygenase variant" as described herein is a cytochrome P450 enzyme having at least one mutation resulting in a higher peroxygenase activity than the corresponding wild-type parent enzyme.

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

A "protein" or "polypeptide", which terms are used interchangeably herein, comprises one or more chains of chemical building blocks called amino acids that are linked together by chemical bonds called peptide bonds.

A "secondary structural element" is a 3-dimensional structure in a protein or protein variant. These secondary structural elements are formed by segments of the amino acid sequence which fold to certain conformations. As used herein, secondary structural elements include the "α-helix" or "helix", a rod-like structure wherein a polypeptide segment is folded by twisting into a right handed screw stabilized by hydrogen-bonding; "beta-pleated sheets," also termed "beta sheets" or simply "β" herein, wherein different segments of a polypeptide sequence run side by side, either parallel or anti-parallel; and the polypeptide segments joining different helices and/or beta sheets, called "loops."

An "enzyme" means any substance, preferably composed wholly or largely of protein, that catalyzes or promotes, more or less specifically, one or more chemical or biochemical reactions. The term "enzyme" can also refer to a catalytic polynucleotide (e.g., RNA or DNA).

A "native" or "wild-type" protein, enzyme, polynucleotide, gene, or cell, means a protein, enzyme, polynucleotide, gene, or cell that occurs in nature.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. Table 1 outlines which amino acids correspond to which codon(s).

TABLE 1

Amino Acids, Corresponding Codons, and Functionality/Property

| Amino Acid | SLC | DNA codons | Side Chain Property |
|---|---|---|---|
| Isoleucine | I | ATT, ATC, ATA | Hydrophobic |
| Leucine | L | CTT, CTC, CTA, CTG, TTA, TTG | Hydrophobic |
| Valine | V | GTT, GTC, GTA, GTG | Hydrophobic |
| Phenylalanine | F | TTT, TTC | Aromatic side chain |
| Methionine | M | ATG | Sulphur group |
| Cysteine | C | TGT, TGC | Sulphur group |
| Alanine | A | GCT, GCC, GCA, GCG | Hydrophobic |
| Glycine | G | GGT, GGC, GGA, GGG | Hydrophobic |
| Proline | P | CCT, CCC, CCA, CCG | Secondary amine |
| Threonine | T | ACT, ACC, ACA, ACG | Aliphatic hydroxyl |
| Serine | S | TCT, TCC, TCA, TCG, AGT, AGC | Aliphatic hydroxyl |
| Tyrosine | T | TAT, TAC | Aromatic side chain |
| Tryptophan | W | TGG | Aromatic side chain |
| Glutamine | Q | CAA, CAG | Amide group |
| Asparagine | N | AAT, AAC | Amide group |

TABLE 1-continued

Amino Acids, Corresponding Codons, and Functionality/Property

| Amino Acid | SLC | DNA codons | Side Chain Property |
|---|---|---|---|
| Histidine | H | CAT, CAC | Basic side chain |
| Glutamic acid | E | GAA, GAG | Acidic side chain |
| Aspartic Acid | D | GAT, GAC | Acidic side chain |
| Lysine | K | AAA, AAG | Basic side chain |
| Arginine | R | CGT, CGC, CGA, CGG, AGA AGG, | |
| Stop codons | Stop | TAA, TAG, TGA | |

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge (see Table 1).

Amino acids other than those indicated as conserved may differ in a protein or enzyme so that the percent protein or amino acid sequence similarity between any two proteins of similar function may vary and can be, for example, at least 30%, preferably at least 50%, more preferably at least 70%, even more preferably 80%, and most preferably at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are the default settings, or those that results in the highest sequence similarity.

As used herein, amino acid residues are "adjacent" when they are within 15, preferably within 10, and more preferably within 7 Angstroms from each other in the 3-dimensional enzyme or protein structure. The enzyme structure can be the structure when bound to substrate or not bound to substrate. Adjacent amino acid residues can be next to each other in the primary amino acid sequence or they can be adjacent as a result of the folded structure. Preferably, no other amino acid fully or partially blocks direct interaction between adjacent amino acid residues.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. Preferred activity units for expressing activity include the catalytic constant ($k_{cat}=V_{max}/E$; $V_{max}$ is maximal turnover rate; E is concentration of enzyme); the Michaelis-Menten constant ($K_m$); and $k_{cat}/K_m$. Such units can be determined using well-established methods in the art of enzymes.

The "stability" or "resistance" of an enzyme means its ability to function, over time, in a particular environment or under particular conditions. One way to evaluate stability or resistance is to assess its ability to resist a loss of activity over time, under given conditions. Enzyme stability can also be evaluated in other ways, for example, by determining the relative degree to which the enzyme is in a folded or unfolded state. Thus, one enzyme has improved stability or resistance over another enzyme when it is more resistant than the other enzyme to a loss of activity under the same conditions, is more resistant to unfolding, or is more durable by any suitable measure. For example, a more "organic-solvent" resistant enzyme is one that is more resistant to loss of structure (unfolding) or function (enzyme activity) when exposed to an organic solvent or co-solvent (e.g., DMSO, tetrahydrofuran (THF), methanol, ethanol, propanol, dioxane, or dimethylformamide (DMF)).

The "thermostability" of an enzyme means its ability to function, optionally function over time, in at elevated temperatures. One way to evaluate thermostability is to assess the ability of the enzyme to resist a loss of activity over time at various temperatures. A more "thermostable" enzyme is more resistant to at least one of loss of structure (unfolding) or function (enzyme activity) when exposed to higher temperatures, for example, at temperatures of at least 35, preferably at least 45, and, even more preferably, at least 55 degrees Celsius. Thermostability can be evaluated by determining the temperature ($T_{50}$) at which half of the enzyme population is unfolded after a 10-minute incubation. Thermostability can also be compared and expressed as the temperature at which half of the initial activity is retained after a 10 minute incubation after an increase from one temperature to another, i.e., from X° C. to Y degrees ° C.

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate. Preferred substrates for hydroxylation using the cytochrome P450 enzymes of the invention include para-nitrophenoxycarboxylic acids ("pNCAs") such as 12-pNCA, as well as decanoic acid, styrene, myristic acid, lauric acid, and other fatty acids and fatty acid-derivatives. For alkane/alkene-substrates, propane, propene, ethane, ethene, butane, butene, pentane, pentene, hexane, hexene, cyclohexane, octane, octene, p-nitrophenoxyoctane (8-pn-pane), and various derivatives thereof, can be used. The term "derivative" refers to the addition of one or more functional groups to a substrate, including, but not limited to, alcohols, amines, halogens, thiols, amides, carboxylates, etc.

The term "cofactor" refers any substance that is necessary or beneficial to the activity of an enzyme. A "coenzyme" means a proteinaceous cofactor that interacts directly with and serves to promote a reaction catalyzed by an enzyme. Many coenzymes also serve as carriers. For example, NAD+ and NADP+ carry hydrogen atoms from one enzyme to another (in the form NADH and NADPH, respectively). An "ancillary protein" means any protein substance that is necessary or beneficial to the activity of an enzyme.

The terms "oxygen donor", "oxidizing agent" and "oxidant" mean a substance, molecule or compound which donates oxygen to a substrate in an oxidation reaction. Typically, the oxygen donor is reduced (accepts electrons). Exemplary oxygen donors, which are not limiting, include molecular oxygen or dioxygen (O2) and peroxides, including alkyl peroxides such as t-butyl hydroperoxide, cumene hydroperoxide, peracetic acid, and most preferably hydrogen peroxide ($H_2O_2$). A "peroxide" is any compound other than molecular oxygen ($O_2$) having two oxygen atoms bound to each other.

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases. An "oxidase" is an oxidation enzyme that catalyzes a reaction in which molecular oxygen (dioxygen or O2) is reduced, for example by donating electrons to (or receiving protons from) hydrogen.

A "luminescent" substance means any substance which produces detectable electromagnetic radiation, or a change in electromagnetic radiation, most notably visible light, by any mechanism, including color change, UV absorbance, fluorescence and phosphorescence. Preferably, a luminescent substance according to the invention produces a detectable color, fluorescence or UV absorbance. The term "chemiluminescent agent" means any substance which enhances the detectability of a luminescent (e.g., fluorescent) signal, for example by increasing the strength or lifetime of the signal.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.).

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. A coding sequence is "under the control" of transcriptional and translational control sequences in a cell when RNA polymerase transcribes the coding sequence into mRNA, which is then trans-RNA spliced and translated into the protein encoded by the coding sequence. Preferably, the coding sequence is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. A gene encoding a protein of the invention for use in an expression system, whether genomic DNA or cDNA, can be isolated from any source, particularly from a human cDNA or genomic library. Methods for obtaining genes are well known in the art, e.g., Sambrook et al (supra).

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background.

Polynucleotides are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that hybridize include those which anneal under suitable stringency conditions and which encode polypeptides or enzymes having the same function, such as the ability to catalyze an oxidation, oxygenase, or coupling reaction of the invention.

The term "expression system" means a host cell and compatible vector under suitable conditions, e.g. for the expression of a protein coded for by foreign DNA carried by the vector and introduced to the host cell. Common expression systems include bacteria (e.g., *E. coli* and *B. subtilis*) or yeast (e.g., *S. cerevisiae*) host cells and plasmid vectors, and insect host cells and Baculovirus vectors. As used herein, a "facile expression system" means any expression system that is foreign or heterologous to a selected polynucleotide or polypeptide, and which employs host cells that can be grown or maintained more advantageously than cells that are native or heterologous to the selected polynucleotide or polypeptide, or which can produce the polypeptide more efficiently or in higher yield. For example, the use of robust prokaryotic cells to express a protein of eukaryotic origin would be a facile expression system. Preferred facile expression systems include *E. coli*, *B. subtilis* and *S. cerevisiae* host cells and any suitable vector.

The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA, that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes. Preferred vectors are described in the Examples, and include without limitations pcWori+ (FIG. 3), pET-26b(+), pXTD14, pYEX-S1, pMAL, and pET22-b(+). Other vectors may be employed as desired by one skilled in the art. Routine experimentation in biotechnology can be used to determine which vectors are best suited for used with the invention, if different than as described in the Examples. In general, the choice of vector depends on the size of the polynucleotide sequence and the host cell to be employed in the methods of this invention.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

A polynucleotide or polypeptide is "over-expressed" when it is expressed or produced in an amount or yield that is substantially higher than a given base-line yield, e.g. a yield that occurs in nature. For example, a polypeptide is over-expressed when the yield is substantially greater than the normal, average or base-line yield of the native polypolypeptide in native host cells under given conditions, for example conditions suitable to the life cycle of the native host cells.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity which can be achieved using conventional purification techniques known in the art.

The 3-dimensional conformation of a P450 enzyme can be determined by X-ray crystallography techniques known to the skilled artisan, or may, in the case where crystallographic data is already publicly available, be simply visualized using software such as the free-ware program Swiss PDB Viewer (available via the ExPASy (Expert Protein Analysis System) proteomics server of the Swiss Institute of Bioinformatics (SIB) website). For example, crystallographic data for the P450 BM-3 heme domain has been published (Li and Poulos, 1994). The same type of software can be applied for determining the distances between selected amino acid residues in the properly conformed wild-type enzyme, or to determine which amino acid residues lie within a selected radius from a reference residue. Such techniques are described at, e.g., the Swiss PDB-viewer web site (accessed via the U.S. web site of expasy.org/spdbv on Aug. 7, 2003).

Crystal structures of wildtype P450 enzymes such as BM-3 with and without substrate reveal large conformational changes upon substrate binding at the active site (Haines et al., 2001; Li and Poulos, 1997; Paulsen and Ornstein, 1995; and Chang and Loew, 2000). The substrate free structure displays an open access channel with 17 to 21 ordered water molecules. Substrate recognition serves as a conformational trigger to close the channel, which dehydrates the active site, increases the redox potential, and allows dioxygen to bind to the heme.

Thermostabilizing mutations may be found in amino acid residues adjacent to an amino acid residue in which an activity or peroxygenase mutation has been introduced in the conformation where the P450 enzyme is with or without substrate. The skilled artisan can determinet whether the distance between residues should be determined when the enzyme has substrate bound or not on a case-by-case basis. For example, this may depend on whether the enzyme will be stored with substrate bound, or used with a particular substrate after storage. Although thermal denaturation may occur over time regardless of whether substrate is bound, many enzymes can be stabilized by the presence of substrate. However, in most thermostability studies of P450 enzymes conducted so far, thermal inactivation is usually measured in the absence of substrate.

Suitable non-P450 BM-3 enzymes preferably have a heme domain at least 30, 40, 50, 60, 70, 80, 85, 90, 95, 96, 97, 98, or 99% sequence identity to SEQ ID NO:3. In an alternative embodiment, the cDNA encoding the non-P450 BM-3 enzymes can hybridize to cDNA encoding SEQ ID NO:3 under conditions of low, medium, or high stringency. Such hybridization conditions are well known in the art. Preferably, although not necessarily, the amino acid substitutions of the invention which are in non-P450 BM-3 enzymes are in conserved residues. FIGS. 4A and 4B show alignment of non-BM-3 enzymes with SEQ ID NO:3, and indicates which residues are identical ("*"), and conserved (":"). For example, the residues aligned with residue L52, F87, H100, S106, M145, A184, M237, S274, V340, and K434 in P450 BM-3 are identical or conserved.

Figure 5:
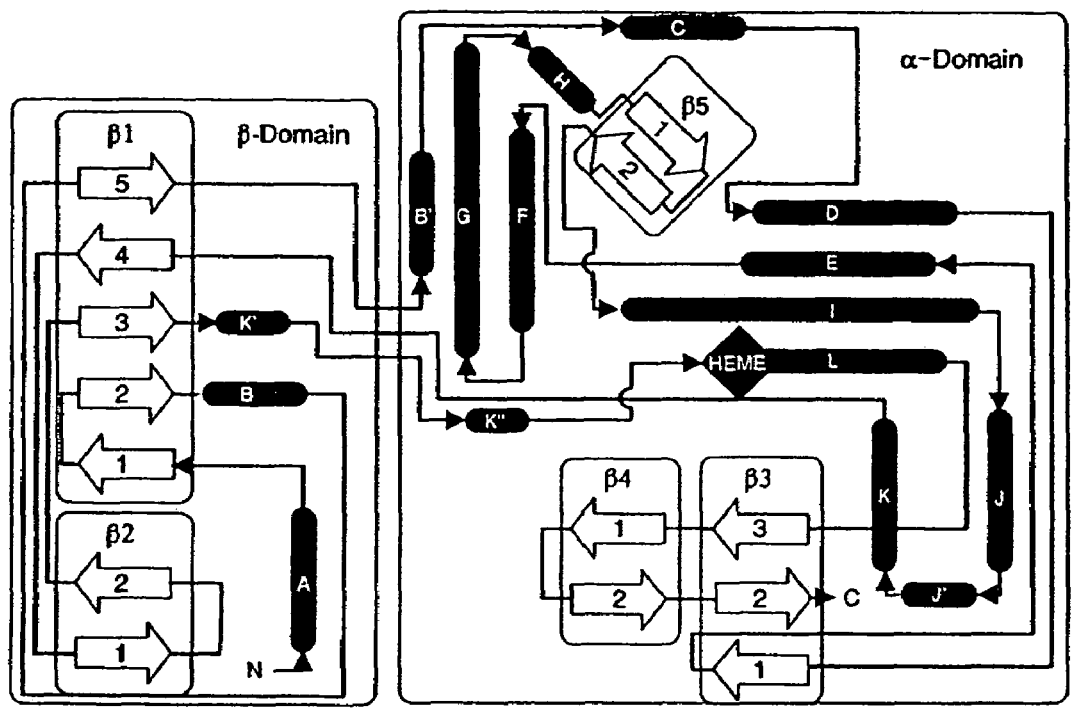
FIG. 5 shows the representative topology diagram of the heme domain of P450s. Helices are represented by black bars, and the length of each of the bars is in approximate proportion to the length of the helix. The strands of β-sheets are shown with arrows. The strands are grouped by the secondary structural elements which they comprise. The structural elements are grouped into the α-helical-rich domain and the β-sheet-rich domain. The heme is shown by the square at the NH$_2$-terminal end of the L-helix. With only minor modifications, this topology diagram could be used for other P450s (Peterson et al., 1995).

While many P450 enzymes may not share a high sequence similarity, the heme-containing domains of P450s do display close structural similarity (Miles et al., 2000). The heme domain ($P450_{BM-P}$) can correspond to the first 464 (SEQ ID NO:3) or 472 amino acid residues of a full-length sequence corresponding to P450 BM-3. Therefore, the positions of the various mutations described for the P450 BM-3 heme domain could be translated to similar positions in different P450s having very low sequence similarity to P450 BM-3 using molecular modeling of those P450s based on sequence homology. Examples of using such techniques to model various P450s based on sequence homology with P450 BM-3 are available (Lewis et al., 1999). The same mutations described here, when placed in their corresponding positions in other P540 structures (as determined by modeling) would confer similar improvements in peroxide shunt pathway activity and/or thermostability. In this regard, FIG. 5 shows a topological view of a cytochrome P450 enzyme, including the various domains, herein also termed "secondary structural elements", of cytochrome P450 enzymes and the mutations contemplated by the present invention in each of those domains. While the topological view presented in FIG. 5 is that of $P450_{BM-P}$, with only minor modifications, this topology diagram may be used for other P450s.

The activity of P450 BM-3 on saturated fatty acids follows the order $C_{15}=C_{16}>C_{14}>C_{17}>C_{13}>C_{18}>C_{12}$ (Oliver et al., 1997). On the $C_{16}$ fatty acid, $k_{cat}=81$ s$^{-1}$ and $K_m=1.4\times10^{-6}$ M ($k_{cat}/K_m=6.0\times10^7$ M$^{-1}$s$^{-1}$). With the $C_{12}$ fatty acid, $k_{cat}=26$ s$^{-1}$, $K_m=136\times10^{-6}$ M and $k_{cat}/K_m=1.9\times10^5$ M$^{-1}$s$^{-1}$ (Oliver et al., 1997). Usually, there is little difference in activity if the C-terminal portion of the heme domain is truncated or substituted. For example, if the last 9-10 residues are substituted for a 6-histidine-tag ("His$_6$") or some other suitable peptide sequence, or deleted, the oxidation capacity of the heme domain is not significantly affected. One of skill in the art can easily determine whether a substitution in or deletion of one or more amino acids in the C-terminal sequence affects the heme domain activity or thermostability.

Described herein are several mutations that have been identified to improve the thermostability of P450 peroxygenases. Thus, a P450 variant of the invention can comprise at least one of these thermostabilizing mutations, optionally in combination with another mutations selected from the ones described in Table 2A, a mutation not described in Table 1A, or no other mutation. The variant P450 enzymes of the invention retain or achieve a higher ability to use the peroxide-shunt pathway, a lesser or no dependency on cofactor, and/or a higher thermostability, than the corresponding wild-type P450. Preferred amino acid mutations are those listed in Table 2A. The skilled artisan could easily identify other P450 variants, including variants comprising truncated, deleted, and inserted amino acid sequences, that comprise one or more of these mutations and that show enhanced peroxide-utilization and thermostability in a suitable assay as compared to the corresponding wild-type P450.

Table 2A described preferred mutation sites for P450 variants (left column), wherein methionine is position zero. Also indicated within parenthesis after each mutated amino acid residue is the location of the amino acid residue (compare to FIG. 5). Preferably, although not necessarily, the amino acid substitution is among those set forth in the right column of Table 2A. A P450 BM-3 full-length or, more preferably, heme domain variants can comprise at least one, preferably at least three, and more preferably at least 7, and even more preferably eleven of the amino acid mutations in Table 2A. Optimally, the P450 variant includes at least one mutation in an amino acid residue selected from L52, S106, A184, and V340. Exemplary P450 mutants include those that have at least 30, 40, 50, 60, 70, 80, 85, 90, 95, 96, 97, 98, or 99% sequence identity to SEQ ID NO:3 and comprise at least one of the mutations in Table 2A.

In one embodiment, a P450 BM-3 peroxygenase variant comprises mutations at amino acid residues F87, H100, M145, M237, S274, and/or K434. In another preferred embodiment, the P450 BM-3 variant also comprises a mutation in one or more of L52, S106, A184, and V340. Most preferably, the mutations are L521, F87A, H100R, S106R, M145V, M145A, A184V, M237L, S274T, V340M, and K434E. Optionally, residue 469 is deleted. However, also contemplated and encompassed by the present invention are amino acid mutations at these positions which are function-conservative to the aforementioned amino acid substitutions. For example, the mutations M145V, M145A, M145I, and M145G, are function-conserved variants because the methionine has been replaced by a hydrophobic amino acid residue.

TABLE 2A

Cytochrome P450 Mutated Amino Acid Residues, their Location and Mutations

| Amino Acid Residue of SEQ ID NOS: 3 (Location) | Amino Acid Mutation |
|---|---|
| K9 (N-terminal) | K9I |
| L52 (beta sheet 1-2) | L52I |
| I58 (helix B) | I58V |
| F87 (loop between helices B' & C - lies above heme (distal side) | F87A or F87S |
| E93 (start of helix C) | E93G |
| H100 (helix C) | H100R |
| S106 (loop between helices C & D) | S106R |
| F107 (loop between helices C & D) | F107L |
| K113 (start of helix D) | K113E |
| A135 (loop between helices D & E) | A135S |
| M145 (helix E) | M145V or M145A |
| A184 (helix F) | A184V |
| N186 (helix F) | N186S |
| D217 (helix G) | D217V |
| M237 (helix H) | M237L |
| N239 (end of helix H) | N239H |
| E244 (loop between helix H and beta sheet 5-1) | E244G |
| S274 (helix I) | S274T |
| L324 (end of helix K) | L324I |
| V340 (beta sheet 2-1) | V340M |
| I366 (helix K") | I366V |
| K434 (beta sheet 4-1) | K434E |
| E442 (end of beta sheet 4-2) | E442K |
| V446 (beta sheet 3-2) | V446I |
| H469 (His-tag) | deleted |

In addition, the invention provides P450 BM-3 mutants having specific nucleic acid and amino acid sequences. The nucleic acid sequences include those which encode the P450 BM-3 variants represented in Table 2B, where the right column lists the amino acid mutations present in each specific variant enzyme. The amino acid sequences include those which have the combinations of amino acid mutations in Table 2B, where all mutations refer to SEQ ID NOS:2 or 3, starting at position zero. The present invention also provides P450 BM-3 nucleic acids encoding silent mutations, as described in the Examples. A particularly preferred mutant according to the present invention is 5H6.

TABLE 2B

P450 BM-3 Full-Length or Heme Domain Peroxygenases

| Designation | Amino Acid Mutations in Wild-Type P450 BM-3 (SEQ ID NO: 2) or Wild-Type P450 BM-3 Heme Domain (SEQ ID NO: 3) |
|---|---|
| 2H1 | K434E |
| 1F8 | K9I, H100R |
| 2E10 | K113E, K434E |
| 2E10-1 | F87A, K113E, D217V, and K434E |
| 2E10-3 | F87A, E93G, K113E, N186S, and K434E |
| 2E10-4 | F87A, K113E, M237L, and K434E |
| step B3 | F87A, H100R, M145V, S274T, and K434E |
| step B6 | F87A, H100R, M145V, M237L, and K434E |
| 21B3 | I58V, F87A, H100R, F107L, A135S, M145V, N239H, S274T, K434E, and V446I |
| TH3 | I58V, F87A, H100R, F107L, A135S, M145V, N239H, S274T, L324I, I366V, K434E, E442K, and V446I |
| TH4 | I58V, F87A, H100R, F107L, A135S, M145V, N239H, S274T, L324I, I366V, K434E, E442K, and V446I |
| 5H6 | L52I, I58V, F87A, H100R, S106R, F107L, A135S, A184V, N239H, S274T, L324I, V340M, I366V, K434E, E442K, V446I, and deletion of H469. |

A peroxygenase mutant has a peroxide-driven oxidation activity at least twice, more preferably at least five, and even more preferably at least 100 times that of the corresponding wild-type P450 in the absence of co-factor, can be thermo-stabilized as described herein. Preferably, the peroxygenase is a variant of a P450 BM-3 heme domain. The P450 BM-3 variants of the invention have an at least two-fold improvement in the ability to oxidize a chosen substrate in the absence of co-factor and presence of $H_2O_2$ as compared to either wild-type P450 BM-3 or the F87A mutant, or the heme domains thereof. Even more preferably, the improvement for this property as compared to wild-type is at least 3-fold, at least 4-fold, at least 5-fold, at least 10-fold, at least 20-fold, at least 40-fold, or at least 80-fold. For peroxide activity compared to F87A, the improvements for this property is at least 10-fold to about 20-fold. The peroxide-driven oxidation activity of the P450 BM-3 variant can, in addition, be at least 10 times that of the mutant F87A.

As shown in the examples, F87A in combination with H100R, M145A, M145V, M237L, S274T, and K434E were noted as especially effective mutations for improving peroxide-shunt activity. These mutations were present in products of recombination, in which the point mutations of several different mutants, (each with different point mutations accumulated from several rounds of error-prone PCR), were allowed to assemble in all combinations. In this manner, improved recombinant products with only beneficial or neutral mutations can be screened for and isolated, and all deleterious mutations removed. Mutation K434E was also noted to have appeared in two separately evolved mutants ("2H1" and "2E10"), again indicating that this mutation is especially effective in improving peroxide shunt activity. It was also found that F87S supported the shunt pathway better than wild-type, although to a lesser degree than F87A.

The peroxygenase variant may comprise a first mutation at a position corresponding to F87 of SEQ ID NO:3 and at least one second mutation in a secondary structure element of the heme domain selected from the group consisting of the N-terminus, β1-2, helix B, a loop between helices B' and C, helix C, a loop between helices C and D, helix D, a loop between helices D and E, helix E, helix F, helix G, helix H, a loop between helix H and beta sheet (β) 5-1, helix I, helix K, helix K", β4-1, β4-2, and β3-2. The at least one second mutation can be in a secondary structural element selected from the group consisting of the loop between helices B' and C, helix C, helix I, and β4-1, or may be a combination thereof. In a preferred embodiment, the isolated nucleic acid encodes a variant having a higher thermostability than the parent. For example, the mutation in the loop between helices B' and C is at an amino acid residue corresponding to amino acid residue F87 of SEQ ID NO:3, the mutation in β1-2 is at an amino acid residue corresponding to amino acid residue L52 of SEQ ID NO:3, the mutation in helix C is at an amino acid residue corresponding to an amino acid residue of SEQ ID NO:3 selected from E93 and H100, the mutation in the loop between helices C and D is at an amino acid residue corresponding to an amino acid residue of SEQ ID NO:3 selected from S106 and F107, the mutation in helix E is at an amino acid residue corresponding to amino acid residue M145 of SEQ ID NO:3, the mutation in helix F is at an amino acid residue corresponding to an amino acid residue of SEQ ID NO:3 selected from A184 and N186, the mutation in helix H is at an amino acid residue corresponding to an amino acid residue of SEQ ID NO:3 selected from M237 and N239, the mutation in helix I is at an amino acid residue corresponding to amino acid residue S274 of SEQ ID NO:3, the mutation in helix K is at an amino acid residue corresponding to an amino acid residue of SEQ ID NO:3 selected from L324 and V340, and the mutation in β4-1 is at an amino acid residue corresponding to amino acid residue K434 of SEQ ID NO:3.

These peroxygenases can then be modified to increase thermostability as compared to the peroxygenase variant, preferably to the same level as the wild-type P450, and even more preferably to a higher thermostability than the wild-type P450. In this thermostabilization process, the peroxygenase capability remains higher than that of the wild-type P450. As shown in Examples 4 and 5, mutations suitable for improving thermostability, preferably while retaining or improving oxidation activity via peroxide shunt pathway, include L521, S106R, M145A, A184V, L324I, V340M, I366V, and E442K. In one embodiment, the thermostabilizing mutations are located in proximity to a mutation which improves oxygenase activity via the peroxide shunt pathway. For example, the thermostabilizing mutation may be located in an adjacent secondary structural element or no more than about 50, preferably no more than 20, and even more preferably no more than 10 amino acids from a mutation improving activity. In a particular embodiment, the thermostabilizing mutations stabilize a P450 BM-3 mutant comprising at least one, preferably at least two, and even more preferably all of the mutations I58V, F107L, S274T, and K434E. Accordingly, a P450 BM-3 variant comprising at least one, preferably at least two, and most preferably all of these mutations, or a nucleic acid encoding such mutants, is a preferred embodiment of the invention. In addition, amino acids which are function-conservative to the amino acid introduced instead of the wild-type amino acid can be used as well. For example, at residue M145, the methionine can be substituted for an alanine, valine, isoleucine, glycine, or any other hydrophobic amino acid (see Table 3) to create a variant P450 BM-3 of the invention.

Moreover, peroxygenase variants may be derived from P450 enzymes other than P450 BM-3. These peroxygenases have a higher ability to use peroxide as an oxygen donor, and a lesser or no dependency on cofactor. In particular, one may construct a P450 peroxygenase mutant based on the sequence of a non-P450 BM-3 enzyme by aligning the sequences and identifying those residues in the non-P450 BM-3 sequence that correspond to the following residues of SEQ ID NO:2: K9, I58, F87, E93, H100, F107, K113, A135, M145, M145, N186, D217, M237, N239, E244, S274, L324, I366, K434, E442, and V446. Once one has identified the residues of the non-P450 BM-3 enzyme that correspond to those of identified above from SEQ ID NOS:2 or 3, one may make an appropriate amino acid substitution to derive a peroxygenase variant. For example, CYP102A3 or CYPE BACSU (GenBank Accession No. 008336) is a P450 that can be used to make a variant of the present invention. The heme domain of CYP102A3 has 67% identity to that of P450 BM-3. By aligning the heme domains of CYP102A3 and P450 BM-3, one can identify those residues of CYP102A3 that correspond with the P450 BM-3 residues identified in Table 2A and make like substitutions to the CYP102A3 sequence. Another example is the K434E mutation, which could be translated into a K437E mutation in the P450 enzyme GenBank Accession No. A69975. These and other exemplary non-BM3 enzymes are identified in Table 3, but the skilled artisan could identify other P450s that may be modified in accordance with the present invention.

TABLE 3

Preferred Non-BM3 Variants

| Non-BM-3 enzyme | Organism | % Identity of Heme Domain to P450 BM-3 Heme Domain | GenBank Accession Number (SEQ ID NO) |
|---|---|---|---|
| CYP 102A3/ CYPE BACSU | Bacillus subtilis | 67% | O08336 (SEQ ID NO: 4) A69975 (SEQ ID NO: 5) |
| CYP 102A2 CYPD BACSU | Bacillus subtilis | 66% | O08394 (SEQ ID NO: 6) D69799 (SEQ ID NO: 7) |
| — | Streptomyces coelicolor A3(2) | 45% | CAB66201 (SEQ ID NO: 8) |
| P450$_{foxy}$ | Fusarium oxysporum | 41% | BAA82526 (SEQ ID NO: 9) |
| — | Gibberella moniliformis | 36% | AAG27132 (SEQ ID NO: 10) |

Any method can be used to "translate" the P450 BM-3 mutation onto another cytochrome P450 enzyme, and such methods are well known in the art. For example, sequence alignment software such as SIM (alignment of two protein sequences), LALIGN (finds multiple matching subsegments in two sequences), Dotlet (a Java applet for sequence comparisons using the dot matrix method); CLUSTALW (available via the World Wide Web as freeware), ALIGN (at Genestream (IGH)), DIALIGN (multiple sequence alignment based on segment-to-segment comparison, at University of Bielefeld, Germany), Match-Box (at University of Namur, Belgium), MSA (at Washington University), Multalin (at INRA or at PBIL), MUSCA (multiple sequence alignment using pattern discovery, at IBM), and AMAS (Analyse Multiply Aligned Sequences). A person of skill can choose suitable settings, or simply use standard default settings, in these programs to align P450 BM-3 with another cytochrome P450 enzyme. See FIG. 4 for representative sequence alignments, and Table 3 for representative non-BM-3 enzymes to which the mutations of the invention can be translated.

Alternatively, sequence alignments of P450 BM-3 with other cytochrome P450 enzymes can be taken from the literature, and amino acid residues corresponding to the mutated amino acid residues of the invention identified. For example, such information can be derived from Ortiz de Montellano (1995) (see, especially, FIG. 11 on page 163 and FIG. 1 on page 187), hereby incorporated by reference. Once the corresponding amino acid residues have been identified, a person of skill can test various mutations of these amino acid residues to identify those that yield improved peroxide shunt utilization ability or improved thermostability as compared to the cytochrome P450 wild-type enzyme. Preferably, the amino acid substitution corresponds to the one(s) listed in Table 2A for the P450 BM-3 mutation, or a function-conservative amino acid thereof.

The non-P450 BM-3 peroxygenase variant can thereafter be thermostabilized the in accordance with the present invention. For example, one may identify those amino acid residues that correspond to L52, S106, M145, and/or E442 of P450 BM-3, and make a substitution in one or more of these residues. Alternatively, one may select amino acid residues that are within 15, 10, or 7 Angstroms of one or more amino acid residues which has been mutated to improve peroxygenase activity, create a library of variants having mutations in these residues, and screen for improved thermostability. The mutation in the non-BM-3 sequence introduced to improve peroxygenase activity preferably results in one or more of the following amino acid substitutions: K91, I58V, F87A, E93G, H100R, F107L, K113E, A135S, M145V, N186S, D217V, M237L, N239H, E244G, S274T, L324I, I366V, K434E, and V446I, where the amino acid residue number refers to the corresponding P450 BM-3 residue. Similarly, the mutation in the non-BM-3 sequence introduced to improve thermostability preferably results in one or more of the following amino acid substitutions: L52I, S106R, M145A, A184V, E442K, and V340M.

Preparation of Mutant or Variant P450 Enzymes

One technique to create peroxygenase mutants or thermostable variants of wild-type or parent cytochrome P450 enzymes, including P450 BM-3, is directed evolution. General methods for generating libraries and isolating and identifying improved proteins according to the invention using directed evolution are described briefly below. More extensive descriptions can be found in, for example, Arnold (1998); U.S. Pat. Nos. 5,741,691; 5,811,238; 5,605,793 and 5,830,721; and International Applications WO 98/42832, WO 95/22625, WO 97/20078, WO 95/41653 and WO 98/27230. The basic steps in directed evolution are (1) the generation of mutant libraries of polynucleotides from a parent or wild-type sequence; (2) (optional) expression of the mutant polynucleotides to create a mutant polypeptide library; (3) screening the polynucleotide or polypeptide library for a desired property of a polynucleotide or polypeptide; and (4) selecting mutants which possess a higher level of the desired property; and (5) repeating steps (1) to (5) using the selected mutant(s) as parent(s) until one or more mutants displaying a sufficient level of the desired activity have been obtained. The property can be, but is not limited to, ability to use peroxide as an oxygen source.

The parent protein or enzyme to be evolved can be a wild-type protein or enzyme, or a variant or mutant which has an improved property such as improved peroxygenase activity or thermostability. The parent polynucleotide can be retrieved from any suitable commercial or non-commercial source. The parent polynucleotide can correspond to a full-length gene or a partial gene, and may be of various lengths. Preferably, the parent polynucleotide is from 50 to 50,000 base pairs. It is contemplated that entire vectors containing the nucleic acid encoding the parent protein of interest may be used in the methods of this invention.

Whether applied in the context of directed evolution or specific protein design based on modelling, any method can be used for generating mutations in the parent polynucleotide sequence to provide a library of evolved polynucleotides, including error-prone polymerase chain reaction, cassette mutagenesis (in which the specific region optimized is replaced with a synthetically mutagenized oligonucleotide), oligonucleotide-directed mutagenesis, parallel PCR (which uses a large number of different PCR reactions that occur in parallel in the same vessel, such that the product of one reaction primes the product of another reaction), random mutagenesis (e.g., by random fragmentation and reassembly of the fragments by mutual priming); site-specific mutations (introduced into long sequences by random fragmentation of the template followed by reassembly of the fragments in the presence of mutagenic oligonucleotides); parallel PCR (e.g., recombination on a pool of DNA sequences); sexual PCR; and chemical mutagenesis (e.g., by sodium bisulfite, nitrous acid, hydroxylamine, hydrazine, formic acid, or by adding nitrosoguanidine, 5-bromouracil, 2-aminopurine, and acridine to the PCR reaction in place of the nucleotide precursor; or by adding intercalating agents such as proflavine, acriflavine, quinacrine); irradiation (X-rays or ultraviolet light, and/ or subjecting the polynucleotide to propagation in a host cell that is deficient in normal DNA damage repair function); or DNA shuffling (e.g., in vitro or in vivo homologous recombination of pools of nucleic acid fragments or polynucleotides). Any one of these techniques can also be employed under low-fidelity polymerization conditions to introduce a low level of point mutations randomly over a long sequence, or to mutagenize a mixture of fragments of unknown sequence. The following sections describe some of the mutagenesis techniques that can be employed to generate the products of the invention.

Error prone PCR is a well-known technique relying on, for example, the intrinsic infidelity of Taq-based PCR, which can be used to mutate or mutagenize a mixture of fragments of unknown sequences (Caldwell, R. C.; Joyce, G. F. PCR Methods Applic. 2, 28 (1992); Leung, D. W. et al. Technique 1, (1989); Gramm, H. et al. Proc. Natl. Acad. Sci. USA 89, 3576 (1992)).

Cassette mutagenesis (Stemmer, W. P. C. et al. Biotechniques 14, 256 (1992); Arkin, A. and Youvan, D.C. Proc. Natl. Acad. Sci. USA 89, 7811 (1992); Oliphant, A. R. et al. Gene 44, 177 (1986); Hermes, J. D. et al. Proc. Natl. Acad. Sci. USA 87, 696 (1990); Delagrave et al. Protein Engineering 6, 327 (1993); Delagrave et al. Bio/Technology 11, 1548 (1993); Goldman, E. R. and Youvan D.C. Bio/Technology 10,1557 (1992)), is a technique in which the specific region optimized is replaced with a synthetically mutagenized oligonucleotide. These techniques can also be employed under low fidelity polymerization conditions to introduce a low level of point mutations randomly over a long sequence, or to mutagenize a mixture of fragments of unknown sequence.

Oligonucleotide directed mutagenesis, which replaces a short sequence with a synthetically mutagenized oligonucleotide, may also be employed to generate evolved polynucleotides having improved expression or novel substrate specificity.

Alternatively, nucleic acid shuffling, which uses a method of in vitro or in vivo, generally homologous, recombination of pools of nucleic acid fragments or polynucleotides, can be employed to generate polynucleotide molecules having variant sequences of the invention.

The polynucleotide sequences for use in the invention can also be altered by chemical mutagenesis. Chemical mutagens include, for example, sodium bisulfite, nitrous acid, hydroxylamine, hydrazine or formic acid. Other agents that are analogues of nucleotide precursors include nitrosoguanidine, 5 bromouracil, 2 aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X rays or ultraviolet light, or by subjecting the polynucleotide to propagation in a host (such as E. coli) that is deficient in the normal DNA damage repair function. Generally, plasmid DNA or DNA fragments so mutagenized are introduced into E. coli and propagated as a pool or library of mutant plasmids.

Where there are regions of known or suspected importance for an enzyme activity or property, saturation mutagenesis has proven useful to generate mutants with improved functions. In this technique, particularly suitable for preparing a library of mutations in an amino acid close to an amino acid mutated to introduce peroxygenase activity, a pool of mutants with all possible amino acid substitutions at one or more residues of interest is generated, and mutants with desired properties are isolated by an efficient selection or screening procedure (Miyazaki, K. and Arnold, F. H. (1999) J. Mol.

Evol. 49, 716-720. Howitz, M. S. and Loeb, L. A. (1986). Proc. Natl. Acad. Sci. USA. 83, 7406-7409). Commercially available kits, such as the QuikChange7 Site-Directed Mutagenesis kit (Stratagene) can be used to carry out saturation mutagenesis. The QuikChange7 kit allows for point mutations to be made without performing error-prone PCR, thus allowing for a high degree of accuracy. A "saturation mutagenesis library" is a library of variants of a parent protein, wherein each variant protein has a mutation in the same amino acid residue.

Once the evolved polynucleotide molecules are generated they can be cloned into a suitable vector selected by the skilled artisan according to methods well known in the art. If a mixed population of the specific nucleic acid sequence is cloned into a vector it can be clonally amplified by inserting each vector into a host cell and allowing the host cell to amplify the vector and/or express the mutant or variant protein or enzyme sequence. Any one of the well-known procedures for inserting expression vectors into a cell for expression of a given peptide or protein may be used. Suitable vectors include plasmids and viruses, particularly those known to be compatible with host cells that express oxidation enzymes or oxygenases. *E. coli* is one exemplary preferred host cell. Other exemplary cells include other bacterial cells such as *Bacillus* and *Pseudomonas, archaebacteria*, yeast cells such as *Saccharomyces cerevisiae*, insect cells and filamentous fungi such as any species of *Aspergillus* cells. For some applications, plant, human, mammalian or other animal cells may be preferred. Suitable host cells may be transformed, transfected or infected as appropriate by any suitable method including electroporation, $CaCl_2$ mediated DNA uptake, fungal infection, microinjection, microprojectile transformation, viral infection, or other established methods.

The mixed population of polynucleotides or proteins may then be tested or screened to identify the recombinant polynucleotide or protein having a higher level of the desired activity or property. The mutation/screening steps can then be repeated until the selected mutant(s) display a sufficient level of the desired activity or property. Briefly, after the sufficient level has been achieved, each selected protein or enzyme can be readily isolated and purified from the expression system, or media, if secreted. It can then be subjected to assays designed to further test functional activity of the particular protein or enzyme. Such experiments for various proteins are well known in the art, and are described below and in the Examples below.

The directed evolution process can be aimed at producing enzyme variants, most preferably enzyme comprising only the entire or partial heme domain, which can use a peroxide, for example peracetic acid, t-butyl hydroperoxide, cumene hydroperoxide, or hydrogen peroxide, and/or which aremore thermostable than its parent. Mutations that enhance the efficiency of peroxide-based oxidation by BM-3 or other cytochrome P450 enzymes can serve to enhance the peroxide shunt activity of the enzyme variants. The mutations described here can be combined with mutations for improving alkane-oxidation activity or organic solvent resistance, for example, and tested for their contributions to peroxide-driven alkane and alkene oxidation.

The evolved enzymes can be used in biocatalytic processes for, e.g., hydroxylation in the absence of molecular oxygen and cofactor, alkane hydroxylation, or for improving yield of reactions involving oxidation of substrates with low solubility in aqueous solutions. The enzyme variants of the invention can be used in biocatalytic processes for production of chemicals from hydrocarbons, particularly alkanes and alkenes, in soluble or immobilized form. Furthermore, the enzyme variants can be used in live cells or in dead cells, or it can be partially purified from the cells. One preferred process would be to use the enzyme variants in any of these forms (except live cells) in an organic solvent, in liquid or even gas phase, or for example in a super-critical fluid like $CO_2$. Another preferred process is to use the enzyme variants in laundry detergents.

The method of screening for selection of mutants or variants, for further testing or for the next round of mutation, will depend on the desired property sought. For example, in this invention, polypeptides encoded by recombinant nucleic acids which encode cytochrome P450 enzymes can be screened for improved use of the "peroxide-shunt" pathway, with less or no dependency on co-factor, and/or for improved thermostability. Such tests are well known in the art. Exemplary tests are provided in the Examples.

In a broad aspect, a screening method to detect oxidation comprises combining, in any order, substrate, oxygen donor, and test oxidation enzyme. The assay components can be placed in or on any suitable medium, carrier or support, and are combined under predetermined conditions. The conditions are chosen to facilitate, suit, promote, investigate or test the oxidation of the substrate by the oxygen donor in the presence of the test enzyme, and may be modified during the assay. The amount of oxidation product, i.e., oxidized substrate, is thereafter detected using a suitable method. Further, as described in WO 99/60096, a screening method can comprise a coupling enzyme such as horseradish peroxidase to enable or enhance the detection of successful oxidation.

In one embodiment, it is not necessary to recover test enzyme from host cells that express them, because the host cells are used in the screening method, in a so-called "whole cell" assay. In this embodiment, substrate, oxygen donor, and other components of the screening assay, are supplied to the transformed host cells or to the growth media or support for the cells. In one form of this approach, the test enzyme is expressed and retained inside the host cell, and the substrate, oxygen donor, and other components are added to the solution or plate containing the cells and cross the cell membrane and enter the cell. Alternatively, the host cells can be lysed so that all intracellular components, including any recombinantly expressed intracellular enzyme variant, can be in direct contact with any added substrate, oxygen donor, and other components. A particularly suitable whole-cell screening assay for P450 BM-3 mutants has been presented by Schwaneberg et al. (2001).

Resulting oxygenated products are detected by suitable means. For example, an oxidation product may be a colored, luminescent, or fluorescent compound, so that transformed host cells that produce more active oxidation enzymes "light up" in the assay and can be readily identified, and can be distinguished or separated from cells which do not "light up" as much and which produce inactive enzymes, less active enzymes, or no enzymes. A fluorescent reaction product can be achieved, for example, by using a coupling enzyme, such as laccase or horseradish peroxidase, which forms fluorescent polymers from the oxidation product. A chemiluminescent agent, such as luminol, can also be used to enhance the detectability of the luminescent reaction product, such as the fluorescent polymers. Detectable reaction products also include color changes, such as colored materials that absorb measurable visible or UV light.

To screen for improved use of the peroxide-shunt pathway and/or a lesser dependency on NADPH co-factor for P450 BM-3 variants, a substrate such as 12-pNCA can be added to the enzyme, and 12-pNCA conversion initiated by adding peroxide (e.g., 1 mM $H_2O_2$). The rate of oxidation of the 12-pNCA substrate can be monitored by measuring the change in absorbance at 398 nm with time, which indicates the rate of formation of the co-product para-nitrophenolate (pNP).

A rapid, reproducible screen that is sensitive to small changes (<2-fold) in activity is desirable (Arnold, 1998). For example, if an alkane-substrate is desired, an alkane analog such as 8-pnpane (see Example 1), can be prepared that generates yellow color upon hydroxylation. This "surrogate" substrate with a C8 backbone and a p-nitrophenyl moiety is an analog of octane, and allows use of a colorimetric assay to conveniently screen large numbers of P450 BM-3 or other cytochrome P450 mutants for increased hydroxylation activity in microtiter plates (Schwaneberg et al., 1999(a); Schwaneberg et al., 2001). Hydroxylation of 8-pnpane generates an unstable hemiacetal which dissociates to form (yellow) p-nitrophenolate and the corresponding aldehyde. The hydroxylation kinetics of hundreds of mutants can then be monitored simultaneously in the wells of a microtiter plate using a plate reader (Schwaneberg et al., 2001). This method is particularly suitable for detecting P450 variants with improved alkane-oxidation activity.

Enzyme variants displaying improved levels of the desired activity or property in the screening assay(s) can then be expressed in higher amounts, retrieved, optionally purified, and further tested for the activity or property of interest.

The cytochrome P450 variants can be selected for a desired property or activity can be further evaluated by any suitable test or tests known in the art to be useful to assess the property or activity. For example, the enzyme variants can be evaluated for their ability to use hydrogen peroxide or another peroxide as an oxygen source, their ability to function in the absence of co-factor, and/or their thermostability. Preferably, the activity of the corresponding wild-type P450 enzyme or a "control" variant is analyzed in parallel, as a control.

An assay for ability to use hydrogen peroxide as oxygen source and/or ability to function in the absence of co-factor essentially comprises contacting the cytochrome P450 variant with a specific amount of a substrate such as, e.g., 12-pNCA or laurate, in the presence of peroxide, e.g., hydrogen peroxide ($H_2O_2$) with low or no amounts of oxygen donor and/or cofactor, while including any other components that are necessary or desirable to include in the reaction mixture, such as buffering agents. After a sufficient incubation time, the amount of oxidation product formed, or, alternatively, the amount of intact non-oxidized substrate remaining, is estimated. For example, the amount of oxidation product and/or substrate could be evaluated chromatographically, e.g., by mass spectroscopy (MS) coupled to high-pressure liquid chromatography (HPLC) or gas chromatography (GC) columns, or spectrophotometrically, by measuring the absorbance of either compound at a suitable wavelength. By varying specific parameters in such assays, the Michaelis-Menten constant ($K_m$) and/or maximum catalytic rate ($V_{max}$) can be derived for each substrate as is well known in the art. In addition, in particular by HPLC and GC techniques, particularly when coupled to MS, can be used to determine not only the amount of oxidized product, but also the identity of the product and therefore the selectivity of the variants. For example, laurate can be oxidized at various carbon positions. When using a fatty acid surrogate substrate such as 12-pNCA, the kinetics of a P450 enzyme reaction can be estimated by monitoring the formation of the chromophore co-product pNP using a spectrophotometer. The total amount of pNP formed is also easily measured and is a good indication of the total amount of substrate oxidized in the reaction. Peroxygenase activities can be measured at room temperature, using a colorimetric assay with 12-p-nitrophenoxycarboxylic acid (12-pNCA) as substrate. In Example 5, using such an assay, it was found that 5H6 retains ~50% of the high activity of 21B3 and is almost ten times as active as HF87A (Table 9).

Figure 8:
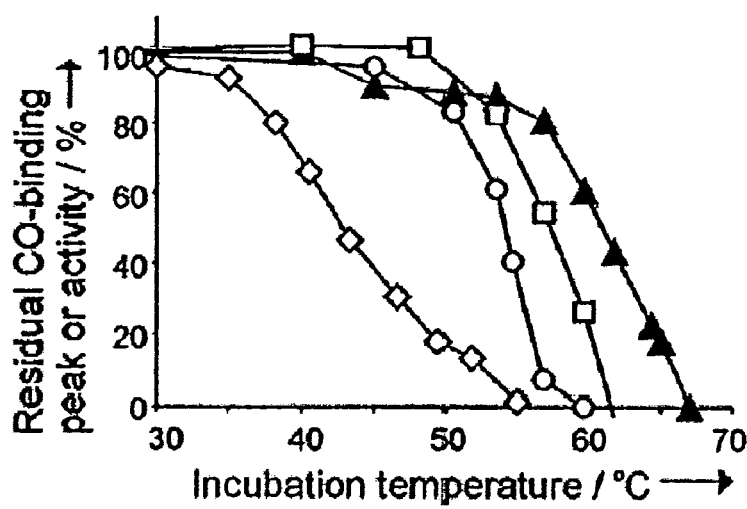
FIG. 8 shows the percentage of 450 nm CO-binding peak of cytochrome P450 BM-3 heme domain, HWT (white square); heme domain of F87A mutant, HF87A (white circle); and 5H6 (black triangle), remaining after 10-minute incubation at the indicated temperatures. For the holoenzyme, BWT (white diamond), the percentage of initial NADPH-driven activity remaining after 10-minute incubations is shown.

To characterize the thermostability of a peroxygenase variant, the fraction of folded heme domain remaining after heat-treatment can be measured. This can be determined from the fraction of the ferrous heme-CO complex that retains the 450 nm absorbance peak characteristic of properly-folded P450. FIG. 8 shows the percentage of properly-folded heme domain protein remaining after 10-minute incubations at different, elevated temperatures. To allow comparison to the wildtype full-length enzyme (BWT), whose stability is limited by the stability of the reductase domain and therefore cannot be determined from the CO-binding measurement, one can determine the residual (NADPH-driven) activity of BWT following 10-minute incubations at the same temperatures. By fitting the data in FIG. 8 to a two-state model, half-denaturation temperatures for the 10-minute heat incubations ($T_{50}$) can be calculated. The $T_{50}$ value thus corresponds to the temperature at which half of the enzyme population is denatured after 10 minutes of incubation. According to the invention, a thermostabilized peroxygenase preferably has a $T_{50}$ temperature higher than that of at least one of the corresponding wild-type enzyme, wild-type heme domain, or non-stabilized peroxygenase parent. In a preferred embodiment, the $T_{50}$ of the thermostabilized peroxygenase is at least 3° C., more preferably at least 5° C., even more preferably at least 10° C., and optimally at least 15° C. higher than that of at least one of the corresponding wild-type enzyme, wild-type heme domain, or non-stabilized peroxygenase parent.

Another useful indicator of thermostability is to conduct an oxidation reaction at one or more temperatures. The temperatures can be in the range of, e.g., about room temperature to about 100 degrees Celsius, more preferably from about 35 degrees to about 70 degrees Celsius. Alternatively, thermostability can be evaluated by measuring the amount of room temperature activity retained following incubation at an elevated temperature. A variant's activity is measured at room temperature as the amount of oxidation product or bi-product formed, or remaining amount of substrate. A sample of the variant is then subject to partial heat inactivation by incubating the sample at a controlled, elevated temperature for a set time. The sample is then rapidly cooled to room temperature and the activity of the sample is measured exactly as the activity was measured before the inactivation. The fraction of initial activity retained by the incubated sample is an indicator of the thermostability of the enzyme variant, and, optionally, compared to wild-type enzyme or a control variant. Such assays can be conducted at several temperatures and for various lengths of time.

Figure 9:
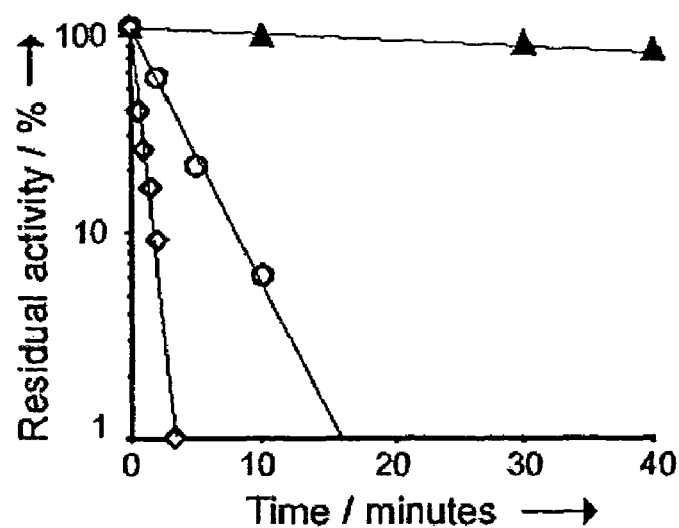
FIG. 9 shows the heat-inactivation of cytochrome P450 BM-3 holoenzyme BWT (white diamond) and peroxygenase mutants HF87A (white circle) and 5H6 (black triangle), calculated as the percentage of activity remaining after incubation at 57.5° C. for the indicated periods of time. Peroxygenase activity was measured for HF87A and 5H6, while NADPH-driven activity was measured for BWT.

Another useful indicator of enzyme stability comes from the rate of inactivation at high temperature. FIG. 9 shows the percentage of activity that remains for different P450 enzyme variants upon heating at 57.5° C. The activities decay exponentially with time (first-order), and the half-life (t½) of each corresponding catalytic system is shown in Table 8. The heme domain of F87A (HF87A; which is less thermostable than the heme domain of wild-type P340 BM-3 (HWT); see FIG. 8) is significantly more resistant to inactivation at 57.5° C. compared to full-length wild-type P450 BM-3 (BWT). The half-life of HF87A is also higher than that of BWT at room temperature. The half-life of 5H6 at 57.5° C. is 50 times longer than that of HF87A and 250 times that of BWT. The fraction of peroxygenase activity remaining after heat treatment correlated with the fraction of remaining CO-binding peak for HF87A and 5H6. Residual activity of HWT cannot be correlated to the remaining CO-binding peak because HWT has essentially no peroxygenase activity.

EXAMPLES

The invention is illustrated in the following examples, which are provided by way of illustration and are not intended to be limiting.

Example 1

Cytochrome P450 BM-3 Heme Domain Mutants More Active in Peroxide-Driven Hydroxylation This example demonstrates the improved activity of P450 BM-3 mutants using hydrogen peroxide instead of NADPH.

Materials and Methods

All chemical reagents were procured from Aldrich™, Sigma™, or Fluka™. Enzymes used for DNA manipulations were purchased from New England Biolabs, Stratagene™, and Boehringer Mannheim™, unless otherwise noted.

All P450 enzymes described here were expressed in catalase-deficient *E. coli* (Nakagawa et al., 1996) using the isopropyl-β-D-thiogalactopyranoside (IPTG)-inducible pCWori+ vector (Barnes et al., 1991), which is under the control of the double Ptac promoter and contains an ampicillin resistance coding region. Expression was accomplished by growth in terrific broth (TB) supplemented with 0.5 mM thiamine, trace elements (Joo et al., 1999), 1 mM 6-aminolevulinic acid, and 0.5-1 mM IPTG at 30° C. for ~18 hrs.

Library Generation

With the exception of one generation, in which the mutant library was created by recombination, libraries were generated under standard error-prone PCR conditions (Zhao et al., 1999). Specifically, 100 µl reactions contained 7 mM $Mg^{2+}$, 0.2 mM dNTPs plus excess concentrations of dCTP and either dTTP or dATP (0.8 mM each), 20 fmole template DNA (as plasmid), 30 pmole of each outside primer, 10 µl Taq buffer (Roche) and 1 µl (5 units) Taq polymerase (Roche). Due to the high concentration of $Mg^{2+}$ and excess of two dNTPs it was determined that no $Mn^{2+}$ was necessary to generate mutant libraries with a suitable fitness landscape (30% to 40% "dead" clones). PCR was performed in a PTC200 thermocycler (MJ Research). The temperature cycle used was: 94° C. for 1 min followed by 29 cycles of 94° C. for 1 min then 55° C. for 1 min then 72° C. for 1:40.

One round of recombination was performed, which resulted in mutants "step B6" and "step B3". StEP recombination was performed essentially as described (Zhao et al., 1999) using HotStarTaq DNA Polymerase (Qiagen). The parent genes used for the recombination included variants "2H1", "1F8-1", "1F8-2", "2E10-1", "2E10-2", "2E10-3", and "2E10-4". A 50 µl PCR reaction contained ~160 ng total template DNA (comprised of approximately equal concentrations of the seven mutant genes), 0.2 mM dNTPs, 5 pmole outside primers, 5 µl Qiagen Hotstar buffer (containing 15 mM $Mg^{2+}$), and 2.5 U HotstarTaq polymerase. PCR was performed in a PTC200 thermocycler (MJ Research). The temperature protocol was as follows: (hot start) 95° C. for 3 min, followed by 100 cycles of 94° C. for 30 sec and 58° C. for 8 sec.

The library that generated thermostable mutant TH4 was made using the GeneMorph PCR Mutagenesis Kit (Stratagene). A parent DNA template concentration of ~500 pg/50 µl was chosen based on the resulting library's suitable fitness landscape (approximately 50% of the library containing essentially inactive variants).

For all PCR manipulations on the entire BM-3 heme domain gene the forward primer sequence was:

(SEQ ID NO:11)
5'-ACAGGATCCATCGATGCTTAGGAGGTCATATG-3' and the reverse primer sequence was:

5'-GCTCATGTTTGACAGCTTATCATCG-3'.  (SEQ ID NO:12)

The heme domain gene was cloned into the pCWori vector using the unique restriction sites BamHI at the start of the gene and EcoRI at the end. The resulting plasmid was transformed into the catalase-deficient *E. coli* strain and colonies were selected on agar plates containing ampicillin (100 µg/ml).

Preparation of 12-pNCA

The 12-pNCA surrogate substrate was prepared as previously described (Schwaneberg et al., 1999(a)) except hydrolysis of the ester was carried out nonenzymatically by refluxing the ester in a 1:1 mixture of THF and a basic (1 M KOH) aqueous solution. TLC and proton NMR analyses showed no detectable impurities in the isolated substrate.

P450 Quantification by CO-Binding

P450 enzyme concentrations were quantified by CO-binding difference spectra of the reduced heme as described (Omura et al., 1964). In general, 50 µl of purified enzyme or enzyme lysate was added to 750 µL of a freshly prepared solution of sodium hydrosulfite (~10 mg/ml) and the P450 was allowed to be reduced for about one minute. The absorbance of this solution was then blanked in a spectrometer before bubbling CO through the reduced enzyme solution for one minute. After another 30 seconds the difference spectrum was measured from 500 nm to 400 nm, and the absorbance value at 490 nm was subtracted from the 450 nm peak. The extinction coefficient for all P450 enzymes was taken to be 91,000 M-1 $cm^{-1}$ (Omura et al., 1964).

Screening for Peroxide Shunt Pathway Activity

Colonies resulting from transformation of a mutant library made by either error-prine PCR or StEP recombination were picked into 1 ml deep-well plates containing LB media (300 µl) and ampicillin (100 µg/ml). Plates were incubated at 30° C., 270 rpm, and 80% relative humidity. After 24 hours, 20 µl of culture liquid from each well was used to inoculate 300 µl of TB media containing ampicillin (100 µg/ml), thiamine (0.5 mM), and trace elements (Joo et al., 1999) contained in a new 1 ml deep-well plate. This plate with TB cultures was grown at 30° C., 270 rpm for approximately three hours before the cells in each well were induced by the addition of δ-aminolevulinic acid (1 mM) and isopropyl-β-D-thiogalactopyranoside (IPTG) (0.5 mM). Cultures were then grown for an additional 18 hours for maximum enzyme expression. All deep-well plates were grown in a Kühner ISF-1-W shaker with humidity control.

After cell growth the plates were centrifuged and supernatants were discarded. Cell pellets were frozen at −20° C.

before lysing. Lysis was accomplished by resuspending the cell pellets in 300-700 μl Tris-HCl buffer (100 mM, pH 8.2) containing lysozyme (0.5-1 mg/ml) and deoxyribonuclease I (1.5-4 Units/ml). The pellets were resuspended and lysed by mixing using a Beckman Multimek 96-channel pipetting robot for approximately 15 minutes before centrifugation. An appropriate volume (10-50 μl) of the resulting cell lysates containing soluble P450 heme domain mutants were used in the activity assay.

All enzyme activity measurements using p-nitrophenoxy-derivative substrates were performed by monitoring the formation of p-nitrophenolate (pNP) (398 nm) at room temperature using a 96-well plate spectrophotometer (SPECTRAmax, Molecular Devices). A typical reaction in a well contained 130 μl 100 mM Tris-HCl buffer pH 8.2, 10 μl stock solution of substrate in DMSO, and 10 μl enzyme solution (purified or as lysate). Reactions were initiated by the addition of 10 μl $H_2O_2$ stock solution. Typical final concentrations were 250 μM substrate (12-pNCA), 1-50 mM $H_2O_2$, and 0.1-1.0 μM P450.

The 398 nm absorbance reading for each well was blanked before addition of $H_2O_2$ so that end point turnovers could be calculated. Rates of peroxide shunt pathway activity for the mutants were calculated as the rate of pNP formation over time (or the increase in absorbance at 398 nm over time). The value for (extinction coefficient)*(path length) for pNP under the exact conditions used in the spectrophotometer assay was calculated from a standard curve generated with known concentrations of pNP. This factor was used to quantify turnover of substrate. The DMSO concentrations used were shown to have no significant effect on the extinction coefficient of pNP.

The most active mutants in a generation were streaked out on agar plates to obtain single colonies. Single colonies were then picked for rescreening. Rescreening was performed as described above, except 10 ml TB cultures were grown instead of deep-well plate cultures. Cell pellets from the centrifuged 10 ml TB cultures were resuspended in 1 ml Tris-HCl (100 mM, pH 8.2) and lysed by sonication. Cell lysates were centrifuged and P450 concentrations in the lysates were then quantified by CO-binding. Specific activities and total enzyme turnover values were then determined to verify that the selected mutants indeed showed improved activity over the parent enzyme. Specific activity is defined as moles of product formed/mole of P450/minute, where product is pNP, quantified by the absorbance at 398 nm. Total turnover is defined as the total number of moles of product produced per mole of enzyme.

Screening for Thermostability

Screening for thermostability was accomplished in the same manner as screening for activity, with the addition of a heat inactivation step. After the activities of the lysates from a deep-well plate have been screened as described above, 50 μl aliquots of each lysate were pipetted from the plate and into a 96-well PCR plate (GeneMate). These aliquots were heated to an appropriate temperature (48° C.-56° C.) in a PTC200 thermocycler (MJ Research) for 10-15 minutes, rapidly cooled to 4° C., and then brought to room temperature. The residual activities of these heat-inactivated lysates were then measured in the same manner that the initial activities were measured. Thermostability was defined as the fraction of initial activity remaining after the heat inactivation. Incubation temperatures were chosen so that the parent of a generation of mutants retained 20%-30% of its residual activity. As examples, the mutant library that was generated with mutant 21B3 as the parent gene was screened by heating to 48.5° C. for 10 minutes. The mutant library that resulted in thermostable mutant TH4 was screened by heating to 56° C. for 15 minutes. Criteria for selection of mutants was that they be both more thermostable than their parent, and able to maintain the same (or nearly the same) peroxide shunt pathway activity as the parent.

General Assay for Measuring P450 Activity

In general, and unless otherwise stated, enzyme activities were measured using p-nitrophenoxy-derivative substrates (e.g. 12-pNCA) by monitoring the formation of p-nitrophenolate (pNP) (398 nm) at room temperature using a 96-well plate spectrophotometer (SPECTRAmax, Molecular Devices), as described above. Typical reactions in a well contained 130 μl 100 mM Tris-HCl buffer pH 8.2, 10 μl stock solution of substrate (e.g. 4 mM 12-pNCA) in DMSO, and 10 μl enzyme solution (purified or as lysate). Peroxide shunt pathway activities were measured by the addition of $H_2O_2$ (1-50 mM), while NADPH-driven hydroxylation by full length P450 enzymes was measured by addition of NADPH (0.2-1 mM).

Quantification of enzyme rates and total turnover numbers were performed as described above. Briefly, P450 enzyme concentrations were determined by CO-binding. Product concentrations were determined as the concentration of para-nitrophenolate (pNP) produced in a well, which was determined from standard curves prepared by varying concentrations of pNP and recording the absorbance at 398 nm. Initial rates were determined as the rate of pNP formation in the first few seconds of the reaction, before there was any noticeable change in reaction rate.

Purification of P450 BM-3 Variants

Purification of full-length wild-type P450 BM-3 and full length P450 BM-3 F87A was performed essentially as described (Schwaneberg et al., 1999(b)) using an Äkta explorer system (Pharmacia Biotech) and SuperQ-650M column packing (Toyopearl).

Purification of the heme domain enzymes took advantage of the 6-His sequence cloned into the C-terminus of each enzyme by using the QIAexpressionist kit (Qiagen) for purification under native conditions. Briefly, cultures were grown for protein expression, as described above. Cells were centrifuged, resuspended in lysis buffer (10 mM imidazole, 50 mM NaH2PO4, pH 8.0, 300 mM NaCl), and lysed by sonication. Cell lysates were centrifuged, filtered, and loaded onto Qiagen Ni-NTA column. The column was washed with wash buffer (20 mM imidazole, 50 mM NaH2PO4, pH 8.0, 300 mM NaCl), and the bound P450 was then eluted with elution buffer (200 mM imidazole, 50 mM NaH2PO4, pH 8.0,300 mM NaCl).

Aliquots of the purified protein were placed into liquid nitrogen and stored at −80° C. When used, the frozen aliquots were rapidly thawed and buffer-exchanged with 100 mM Tris-HCl, pH 8.2 using a PD-10 Desalting column (Amersham Pharmacia Biotech). P450 concentrations were then determined by the CO-binding difference spectrum.

Determination of shunt pathway activity and product distributions with myristic acid, lauric acid, decanoic acid, and styrene.

A typical reaction contained 1-4 μM purified P450 heme domain enzyme and 1-2 mM substrate in 500 μl 100 mM Tris-HCl, pH 8.2 (for reactions with styrene the solution also contained 1% DMSO). Reactions were initiated by the addition of 1-10 mM $H_2O_2$. For determining rates, the reactions were stopped at specific time points (e.g., 1, 2, and 4 minutes) by the addition of 7.5 µl 6 M HCl for the reactions on fatty acids. Reactions using styrene as substrate were stopped by the addition of 1 ml pentane followed by vigorous shaking. For determining total turnover values, the reactions were allowed to continue until the enzyme was completely inactivated by the peroxide. At the end of each reaction an internal standard was added prior to extraction. For reactions with myristic and lauric acid, 30 nmoles of 10-hydroxydecanoic acid was used as the internal standard. For reactions with dodecanoic acid, 30 nmoles of 12-hydroxylauric acid was added the internal standard. Finally, 200 nmoles of 3-chlorostyrene oxide was added as the internal standard for styrene reactions.

Reactions with styrene were extracted twice with 1 ml pentane. The pentane layer was evaporated down to ~200 µl to concentrate the products. Fatty acid reactions were extracted twice with 1 ml ethyl acetate. The ethyl acetate layer was dried with sodium sulfate and then evaporated to dryness in a vacuum centrifuge. The resulting product residue was dissolved in 100 µl of a 1:1 pyridine:BSTFA (bis-(trimethylsilyl-trifluoroacetamide) mixture containing 1% trimethylchlorosilane (TMCS). This mixture was heated at 80° C. for 30 minutes to allow for complete derivitization of the acid and alcohol groups to their respective trimethylsilyl esters and ethers.

Reaction products were identified by GC/MS using a Hewlett Packard 5890 Series II gas chromatograph coupled with a Hewlett Packard 5989A mass spectrometer. Quantification of lauric acid, decanoic acid, and styrene reaction products was accomplished using a Hewlett Packard 5890 Series II Plus gas chromatograph equipped with a flame ionization detector (FID). The GCs were fitted with an HP-5 column. Authentic standards for each hydroxylated isomer of the fatty acids were not available, so standard curves were generated using the available ω-hydroxylated standards (12-hydroxylauric acid and 10-hydrodecanoic acid). Authentic standard samples were prepared in the same fashion as the reaction samples, except the enzyme was inactivated by the addition of HCl before the addition of peroxide. All peak areas were normalized by dividing by the peak area of the internal standard added to each sample. It was assumed that the FID response is the same for all regioisomers of a given hydroxylated fatty acid. For styrene, the only product detected was styrene oxide, for which the authentic standard was available.

Reactions that were stopped one minute after the addition of peroxide were used to estimate the initial rates of peroxide shunt pathway activity on each substrate. The quantity of product in the reaction mixture was determined from the standard curve and divided by the quantity of P450 present in the reaction, giving an estimate of the initial rate (nmol product/nmol P450/min).

Results

Both wild-type BM-3 and the F87A mutant were tested for shunt pathway activity using 12-pNCA as substrate. Whereas $H_2O_2$-driven activity could not be detected with the wild-type BM-3, the F87A mutant was able to use $H_2O_2$ for 12-pNCA hydroxylation at detectable levels (~50 nmol product/mol P450/min when using 10 mM $H_2O_2$ and ~90 nmol product/nmol P450/min using 50 mM $H_2O_2$). The Km,app of BM-3 F87A for $H_2O_2$ was estimated to be ~15 mM using enzyme from lysates. The enzyme is very short-lived in the presence of peroxide: in 50 mM $H_2O_2$ most activity is lost after ~2 minutes.

A comparison of NADPH-driven versus $H_2O_2$-driven activity in cell lysates containing BM-3 F87A showed that shunt pathway activity was retained for longer periods than NADPH activity. Whereas less than 10% of the lysate's NADPH activity remained after sitting one day at room temperature, the same lysate retained more than 63% of the shunt pathway activity. This is likely to be due to the labile link between the heme domain and the reductase domain. This may also be in part due to a greater instability of the reductase domain compared to the heme domain, or a greater instability of one or more protein components involved in the electron transfer process used by the NADPH pathway compared to the heme domain. Regardless, this is strong evidence that it is easier to engineer stability in the heme domain alone than in the full length BM-3 enzyme.

When using hydrogen peroxide instead of NADPH, the reductase domain of P450 BM-3 is not necessary and only places an added burden on the E. coli host during protein expression. Therefore a nucleotide sequence encoding the heme domain alone was cloned into the pCWori+ vector, which was found to result in approximately four-fold higher molar expression.

The P450 BM-3 heme domain was considered to be composed of the first 463 amino acids of the full-length BM-3 protein (not including the start methionine, which is considered to be amino acid numbered zero). The sequence coding for six histidines was cloned onto the end of the BM-3 heme domain gene, resulting in a 469 amino acid protein. P450 heme domain mutant F87A containing a 6-His tag was chosen as the starting point for directed evolution experiments. That is, the gene coding for this variant served as parent template used for generating the first mutant library to be screened for improvements in shunt pathway activity. The addition of the 6-His tag had a negligible effect on shunt pathway activity for the F87A mutant.

E. coli naturally produces catalase and the presence of catalase in the lysate was problematic in the development of a screening assay for shunt pathway activity. Bubbles were formed from the catalase reaction, and $H_2O_2$ concentrations were rapidly reduced. Therefore a catalase-free E. coli strain was used, in which the genes that code for catalase were knocked out of the host genome (Nakagawa et al., 1996). This strain prevented bubble formation, and allowed maintaining steady concentrations of $H_2O_2$, resulting in a sensitive screening system.

As described above, P450 BM-3 heme domain mutant F87A (F87A mutation in SEQ ID NO:3) was used as the starting point for directed evolution of $H_2O_2$-driven hydroxylation of the surrogate substrate 12 p-nitrophenoxy-carboxylic acid (12-pNCA). Mutant libraries were screened for activity in both 1 mM $H_2O_2$ and 50 mM $H_2O_2$ in efforts to improve activity and stability in $H_2O_2$. Mutagenesis by error-prone PCR and screening generated F87A heme domain variants with up to five-fold improved total-shunt pathway activity. Generating heme domains or the full length enzyme makes no difference since the shunt pathway activity is the same, and the reductase portion has no influence.

The first generation resulted in mutants "2H1", "1F8" and "2E10". Two separate second generation libraries were then created and screened, resulting in mutants "1F8-1" and "1F8-2" (where "1F8" was the parent gene), and "2E10-1", "2E10-2", "2E10-3", and "2E10-4" (where "2E10" was the parent gene).

Mutant 2E10-1 had an initial rate of ~50 nmol/nmol P450/min in 1 mM $H_2O_2$, while the rate with F87A is ~10 nmol/nmol P450/min. Sequencing of several improved variants revealed a number of mutations that confer these improvements. The mutants and known mutations are listed in Table 4.

TABLE 4

Mutations from error-prone PCR resulting in BM-3 heme domain variants showing improved $H_2O_2$-driven hydroxylation. All mutants additionally comprise the F87A substitution.

| Base Change | Amino Acid Change | Variant where Mutation First Appears |
|---|---|---|
| A26T | K9I | 1F8 |
| A213G | (SILENT) | 2H1 |
| A278G | E93G | 2E10-3* |
| A299G | H100R | 1F8 |
| A337G | K113E | 2E10 |
| A650T | N186S | 2E10-3* |
| A650T | D217V | 2E10-1 |
| A709T | M237L | 2E10-4* |
| A731G | E244G | 1F8 |
| G735A | (SILENT) | 1F8 |
| A885G | (SILENT) | 2E10-3* |
| T1188A | (SILENT) | 2E10 |
| A1300G | K434E | 2E10 and 2H1 |

*Parent is 2E10

Mutation K434E was noted to have appeared in two separately evolved mutants ("2H1" and "2E10"), indicating that this mutation is especially effective in improving peroxide shunt activity. Additional improved mutants include 1F8-1 and 1F8-2 (whose parent is 1F8) and 2E10-2 (whose parent is 2E10).

Example 2

Improved Hydrogen Peroxide-Driven Hydroxylation by Evolved Cytochrome P450 BM-3 Heme Domain This Example describes the discovery of novel cytochrome P450 BM-3 variants that use hydrogen peroxide ($H_2O_2$) for substrate hydroxylation more efficiently than the wild-type enzyme.

Materials and Methods

The same materials and methods were used in this Example as those described in Example 1. However, in Example 2, StEP recombination was carried out with error-prone mutants. A 50 μl PCR reaction contained ~160 ng total template DNA (comprised of approximately equal concentrations of the seven mutant genes), 0.2 mM dNTPs, 5 pmole outside primers, 5 μl Qiagen Hotstar buffer (containing 15 mM $Mg^{2+}$), and 2.5 U HotstarTaq polymerase. PCR was performed in a PTC200 thermocycler (MJ Research). The temperature protocol was as follows: (hot start) 95° C. for 3 min, followed by 100 cycles of 94° C. for 30 sec and 58° C. for 8 sec. Genes from seven mutants were used and resulted in some improvements.

Results

One round of StEP recombination (Zhao et al., 1999) was performed, which resulted in mutants "stepB6" and "stepB3". StEP recombination was performed essentially as described (Zhao et al., 1999) using HotStarTaq DNA Polymerase (Qiagen). The parent genes used for the recombination included variants "2H1", "1F8-1", "1F8-2", "2E10-1", "2E10-2", "2E10-3", AND "2E10-4".

Mutant libraries were screened for activity on the surrogate substrate 12-p-nitrophenoxy-carboxylic acid (12-pNCA) in both 1 mM $H_2O_2$ and 50 mM $H_2O_2$. A combination of error-prone PCR and recombination of improved mutants by staggered extension process (StEP) resulted in variants with improved shunt pathway activity. Mutant "stepB3" had a total activity that was seven-fold higher than the BM-3 F87A mutant in 50 mM $H_2O_2$ and a total turnover in 1 mM $H_2O_2$ that was four times higher than F87A. Sequencing of this mutant revealed five mutations in the DNA sequence, corresponding to four amino acid changes (see Table 5).

Another variant found in the StEP library, "stepB6", showed similar activity to "stepB3", but has a lower apparent Km for $H_2O_2$ (about 8 mM) and has CO-binding difference spectrum peaks at both 450 nm and 420 nm. This spectral property is typically indicative of a misfolded and inactive P450, and indicates a change in the electron character of the proximal ligand. The 420 nm CO-binding peak has been observed with other heme enzymes that more readily bind $H_2O_2$ (e.g., peroxidases). The sequence of "step B6" was only one amino acid change different from "stepB3". The mutations are listed in Table 5.

One goal of this experiment was to combine the properties of a mutant active at high peroxide concentrations with the properties of another mutant active at low peroxide levels. This indeed worked. Mutant "stepB6" showed improved activity under both conditions: more than six-times faster than the F87A mutant in 1 mM $H_2O_2$ and more than five-fold higher total turnover than F87A in 50 mM $H_2O_2$.

TABLE 5

Mutations in "stepB3" and "stepB6" P450 BM-3 variants (in addition to F87A)

| Base Substitution | Amino Acid Substitution | Step B3 | Step B6 |
|---|---|---|---|
| A299G | H100R | X | X |
| A433G | M145V | X | X |
| A709T | M237L | — | X |
| T820A | S274T | X | — |
| T1188A | (SILENT) | X | X |
| A1300G | K434E | X | X |

The mutations in the step B3 and B6 variants were recognized as particularly important for improved peroxide-utilization, since these mutations were present in products of recombination, whereby the point mutations of seven different mutants (each with different point mutations accumulated from previous rounds of error-prone PCR) were allowed to assemble in all possible combinations. In this manner it is easy to screen for and isolate improved recombinant products with only beneficial or neutral mutations, and all deleterious mutations removed.

Example 3

Improved Peroxide-Driven Hydroxylation by Evolved Cytochrome P450 BM-3 Heme Domain This Example describes a novel cytochrome P450 BM-3 variant that use hydrogen peroxide ($H_2O_2$) for substrate hydroxylation more efficiently than the wild-type enzyme.

Methods and Results

Further rounds of directed evolution to improve peroxide shunt pathway activity were carried out starting with mutant "stepB3". Error-prone PCR was used to generate mutant libraries, and screening was performed as described above using 1 mM $H_2O_2$. After two rounds of evolution mutant "21B3" was isolated.

After reacting wild-type, F87A and 21B3 with laurate, the reaction products were extracted, dried, and derivatized to the trimethylsilyl esters and ethers. The regiospecificity was quite different for the wild-type compared to F87A and 21B3. The F87A mutation appears to broaden regiospecificity and shift hydroxylation away from the terminal positions. Whereas the wild-type BM-3 typically oxidizes fatty acids exclusively at positions ω-1, ω-2, and ω-3 under the NADPH pathway (as well as under the peroxide shunt pathway, although at much lower levels), mutant F87A hydroxylates fatty acids at positions ω-1, ω-2, ω-3, ω-4, and ω-5 under the NADPH and peroxide shunt pathways. GC analysis of the reaction mixture showed that the total product area relative to the internal standard (IS) area for 21B3, heme domain mutant F87A, and wild-type was 8.9, 1.1, and 0.11, respectively. The relative ratios of the hydroxylated positions varies with the substrate and appears to be the same in evolved mutants "21B3" and "TH4", which contain the F87A mutation. Sequencing of mutant 21B3 revealed 13 mutations in the DNA sequence, corresponding to 9 amino acid changes (in addition to F87A). The mutations are listed in Table 6.

TABLE 6

Mutations in peroxide-dependent mutant "21B3"
(in addition to F87A).

| Base Change | Amino Acid Change |
|---|---|
| A172G | I58V |
| A195T | (SILENT) |
| A299G | H100R |
| C321A | F107L |
| G403T | A135S |
| A433G | M145V |
| A684G | (SILENT) |
| A715C | N239H |
| T810C | (SILENT) |
| T820A | S274T |
| T1188A | (SILENT) |
| A1300G | K434E |
| G1336A | V446I |

For characterization, enzymes were purified by binding the 6-His tag to a Ni-NTA agarose column (Qiagen), washing, and eluting with imidazole (as described above). The imidazole was then removed in a buffer exchange column. Mutant "21B3" was found to be more than fifteen times more active than mutant F87A on 12-pNCA using 5 mM $H_2O_2$ (490 nmol/nmol P450/min versus 30 nmol/nmol P450/min). The total turnover of 12-pNCA achieved by mutant "21B3" was approximately twelve times higher than mutant F87A (~1000 versus ~80 in 5 mM $H_2O_2$).

Similar improvements in activity were seen with real fatty acid substrates by GC analysis. Using laurate (dodecanoic acid) and 5 mM $H_2O_2$, mutant 21B3 was approximately eight times more active than F87A (~28 nmol/nmol P450/min vs. ~3 nmol/nmol P450/min using 10 mM $H_2O_2$). The GC data indicated that wild-type BM-3 is capable of only single to perhaps triple total turnovers under the shunt pathway.

Similar activity results were also found with myristic acid, decanoic acid, and styrene. Decanoic acid was oxidized by "21B3" at an initial rate of ~82 nmol/nmol P450/min, whereas the initial rate with F87A was ~10 nmol/nmol P450/min using 10 mM $H_2O_2$. Finally, the peroxide-driven oxidation of styrene to styrene oxide by "21B3" had an initial rate of ~50 nmol/nmol P450/min using 10 mM $H_2O_2$, while the rate with F87A was not detectable. It should be noted that the shunt pathway activity of mutant "21B3" on styrene is higher than the normal NADPH-driven activity of wild-type BM-3 on this same substrate (~30 nmol/nmol P450/min using 0.2 mM NADPH).

The initial 12-pNCA hydroxylation rate for P450 BM-3 variant 21B3 at various peroxide concentrations was compared to that of the F87A variant and wild-type enzyme heme domains. The same results have been verified with the full protein, as described in the Materials and Methods section. The 21B3 heme domain variant was found to yield a peak initial 12-pNCA conversion rate of 780 mole product per mole enzyme per minute at 25 mM $H_2O_2$, whereas the initial rates for the F87A heme domain at this peroxide concentration was only 76 mole product per mole enzyme per minute. The rates for wild-type BM-3 were not detectable.

In addition, the total turnover of 12-pNCA of 21B3 in the peroxide shunt pathway was compared to the corresponding F87A and wild-type enzymes at various concentrations of $H_2O_2$. This assay was carried out as described above (see Materials and Methods). At concentrations of 1, 5, and 10 mM $H_2O_2$, the total substrate turnover of 21B3 was about 17, 12, and 10 times higher than the F87A variant, whereas the total turnover of the wild-type enzyme was barely distinguishable. The turnover units are total moles of product made per mole of P450 up to the point that it has lost all activity.

EXAMPLE 4

Peroxide-Dependent, Thermostable Cytochrome P450 BM-3 Variants

It was noticed that the stability of the evolved peroxide-driven mutants was lower than that of the original F87A parent. Stability of these mutants is an important factor when considering possible applications. Mutants with greater thermostability could be used at elevated temperatures and would potentially have even greater activity at elevated temperatures. Therefore this example sought to improve the thermostability of the peroxide-dependent mutants without sacrificing activity.

Starting with mutant "21B3", directed evolution to improve thermostability while retaining maximum peroxide shunt pathway activity was performed using error-prone PCR to generate mutant libraries. Libraries were screened using 1-5 mM $H_2O_2$. After screening three generations of libraries created with error-prone PCR (as described above), thermostable mutant "TH3" was isolated. An additional library was generated with "TH3" as the parent using the GeneMorph PCR Mutagenesis Kit (Stratagene), resulting in thermostable mutant "TH4".

TABLE 7

Mutations in peroxide-dependent, thermostable P450 BM-3
variant "TH4", in addition to F87A. (Percentage values
represent the changes in codon usage by E. Coli)

| Base Change(s) | Amino Acid Change |
|---|---|
| A172G | I58V |
| A195T | SILENT (S); 14% to 15% |
| A299G | H100R |
| C321A | F107L |
| G403T | A135S |
| A433G + T434C | M145A |
| A684G | SILENT (E); 67% to 33% |
| A715C | N239H |

TABLE 7-continued

Mutations in peroxide-dependent, thermostable P450 BM-3 variant "TH4", in addition to F87A. (Percentage values represent the changes in codon usage by *E. Coli*)

| Base Change(s) | Amino Acid Change |
| --- | --- |
| T810C | SILENT (S); 16% to 26% |
| T820A | S274T |
| T970A | L324I |
| A1096G | I366V |
| T1188A | SILENT (G); 33% to 13% |
| A1300G | K434E |
| T1309C | SILENT (L); 14% to 4% |
| G1324A | E442K |
| G1336A | V446I |

The only difference between the mutations in TH4 and the mutations in the mutant from the previous generation (mutant "TH3", which was the parent used to generate the library that resulted in TH4) is that previously occurring mutation M145V was changed to M145A. Thus, throughout the course of evolving shunt pathway activity and stability, a single codon was mutated on two separate occasions, resulting in an amino acid (Ala) that could not be reached by a single base mutation.

The thermostability of the TH4 variant was compared to the 21B3 and F87A P450 BM-3 variants by comparing the ratios of residual activity to initial activity of each enzyme after incubation at various temperatures in the range of 35-65° C. for 10 minutes. Activities before and after heat inactivation were measured using $H_2O_2$ and 12-pNCA as described in the Methods. This test was conducted in the absence of cofactor. The results showed that TH4 retained activity to a higher degree than F87A variant, which, in turn, was more stable than 21B3. Additionally, TH4 had essentially the same initial activity as "21B3". Thus, of these enzyme variants, TH4 was most thermostable (at least as stable as the original parent (F87A)), and retained peroxide activity essentially equal to that of 21B3. Because of its stability, TH4 has a greater applicability for higher temperature environments, where its activity will also be higher. The mutations that appear to play a particular role in thermostability are therefore M145A, L324I, I366V, and E442K (those which have been accumulated throughout the thermostability directed evolution process).

Different peroxides were also tested, including cumene hydroperoxide, t-butyl hydroperoxide, and peracetic acid, for their utilization by the P450 BM-3 variants. Of the different peroxides, $H_2O_2$ was found to be most effective in the 12-pNCA assay, where 12-pCNA is hydroxylated at C-12, followed by peracetic acid, for both the BM-3 F87A mutant and the evolved variants.

EXAMPLE 5

Thermostable P450 BM-3 Peroxygenase Variants

The laboratory-evolved P450 BM-3 heme domain variant TH4, which has significantly improved peroxygenase activity ($H_2O_2$-driven hydroxylation) compared to the wild-type enzyme, and improved peroxygenase activity as well as thermostability as compared to the heme domain of the F87A mutant (HF87A), is described above. This Example describes further improving thermostability to a level better than the wild-type enzyme heme region without sacrificing the improved peroxygenase activity over the wild-type enzyme.

Methods

General Remarks. All chemical reagents were procured from Aldrich™, Sigma™, or Fluka™. Restriction enzymes were purchased from New England Biolabs™ and Roche™. Deep-well plates (96 wells, 1 ml volume per well) for growing mutant libraries were purchased from Becton Dickinson™. Flat-bottom 96-well microplates (300 µl per well) for screening mutant library activities were purchased from Rainin™.

Enzyme Expression and Purification. P450 BM-3 enzymes were expressed in catalase-deficient *E. coli* (Nakagawa et al., 1996) using the α-D-thiogalactopyranoside (IPTG)-inducible pCWori+ vector (Barnes et al., 1991). The heme domain consisted of the first 463 amino acids of P450 BM-3 followed by a 6-His sequence at the C-terminus, which had no significant influence on activity. Cultures for protein production were grown and proteins were purified as described (Cirino and Arnold, 2002(a)). Purified enzyme samples were stored at −80° C. until use, at which time they were thawed at room temperature and then kept on ice. Concentrations of properly-folded P450 enzyme were determining from the 450 nm CO-binding difference spectra of the reduced heme, as described (Omura and Sato, 1964).

Preparation of Mutant Libraries. Error-prone PCR libraries were prepared using standard protocols (Cirino et al., 2003). Starting with 21B3 as the parent, three rounds of error-prone PCR (using Taq DNA polymerase (Roche)) followed by screening were performed, and the most thermostable mutant which did not lose peroxygenase activity was chosen as the parent for the next generation. Two additional generations were prepared with the GeneMorph™ PCR Mutagenesis Kit (Stratagene). In the final generation leading to mutant 5H6, a recombinant library was prepared by DNA shuffling (Stemmer, 1994) using Pfu Ultra DNA Polymerase™ (Stratagene). Parents for the recombinant library included HF87A, mutants from the previous generation which were more stable but less active, and mutants with increased activity.

Mutant Library Screening. Screening was performed as described below, subjecting cell lysates to a heat inactivation step and screening for residual activity (see also (Cirino and Georgescu, 2003)). Briefly, cultures expressing mutants were grown in 96-well deep-well plates. After cell growth, the plates were centrifuged, cell pellets were frozen at −20° C., and the cells were lysed in Tris-HCl buffer (100 mM, pH 8.2) containing lysozyme (0.5-1 mg/ml) and deoxyribonuclease 1 (1.5-4 Units/ml). Clarified cell lysates were transferred to 96-well microplates for activity measurements at room temperature (described below). Lysates were also transferred to 96-well PCR plates (GeneMate) and heated to an appropriate temperature (48° C.-57.5° C.) in a PTC200 thermocycler (MJ Research) for 10-15 minutes, rapidly cooled to 4° C., and then brought to room temperature. The residual activities of these heat-treated lysates were then measured in the same manner as the initial activities. Clones showing a higher fraction of activity remaining after heat treatment and high initial activity were characterized further.

Activity Assay. Activity on 12-pNCA (Schwaneberg et al., 1999) was determined by monitoring the formation of p-nitrophenolate (pNP) (398 nm) at room temperature using a 96-well plate spectrophotometer (SPECTRAmax Plus, Molecular Devices), as described. Reaction wells contained Tris-HCl buffer (140 µl of 100 mM, pH 8.2), a stock solution of substrate (10 µl of 4 mM 12-pNCA) in DMSO, and purified enzyme or clarified lysate. Reactions were initiated by the addition of an $H_2O_2$ stock solution (10 µl). Data for accurate determination of 12-pNCA turnover rates with purified enzyme were collected using a BioSpec1601 spectrophotometer (Shimadzu), where absorbance changes could be registered every 0.1 seconds. Typical final concentrations were 250 µM 12-pNCA, 6% DMSO, 1-10 mM $H_2O_2$, and 0.1-1.0 µM P450. The extinction coefficient for pNP was determined from standard pNP solutions prepared under identical reaction conditions. NADPH-driven activity of BWT was determined spectrophotometrically from the initial rate of NADPH consumption (measured as the decrease in 340 nm absorbance) in the presence of myristic acid, as described (Yeom and Sligar, 1997).

Data for $T_{50}$ Determination. Purified enzyme samples (~20 µM) in Tris-HCl buffer (100 mM, pH 8.2) were incubated for 10 minutes at different temperatures. Samples were then cooled on ice, and the concentration of properly-folded heme domain (diluted 8×) was estimated from the 450 nm CO-binding difference spectra and compared to the CO-binding peak prior to heat treatment. Residual NADPH-consumption activity was measured for BWT. Data in FIG. 8 represent average values from at least two experiments.

Data for t½ Determination. Concentrated purified enzyme (70 µM) was added to pre-heated (57.5° C.) Tris-HCl buffer (100 mM, pH 8.2) and incubated at 57.5° C. Samples were removed at time intervals, quenched by dilution into cold buffer, brought to room temperature, and assayed for residual activity. Data in FIG. 9 represent average values from at least two experiments.

Results

TH4 was used as the parent of a random mutagenesis library. Since no variants which were both more stable and more active than TH4 were identified in this first library, the genes of mutants which were either more active or more thermostable were recombined using DNA shuffling to produce a recombinant library. Screening the recombinant library resulted in thermostable variant 5H6.

TABLE 8

Thermostability and activity parameters for evolved and parental P450s. BWT = full-length, wildtype P450 BM-3; HWT = wildtype P450 BM-3 heme domain; HF87A = P450 BM-3 heme domain containing mutation F87A; 21B3 & 5H6 = evolved heme domain peroxygenase variants.

| Mutant | $T_{50}$ for 10-minute incubations[a] (° C.) | t½ at 57.5° C.[b] (minutes) | Peroxygenase Activity[c] (minute$^{-1}$) |
|---|---|---|---|
| BWT | 43 | 0.46 | <5 |
| HWT | 57 | n.d. | <5 |
| HF87A | 54 | 2.3 | 23 |
| 21B3 | 46 | n.d. | 430 |
| 5H6 | 61 | 115 | 220 |

[a]Calculated from the data in FIG. 8, fit to two-state denaturation equation.
[b]Calculated from the data in FIG. 9, fit to a first-order exponential decay equation.
[c]Reported as initial rates at room temperature on 12-pNCA in 10 mM $H_2O_2$ and 6% DMSO.
n.d.: not determined.

Figure 6A:
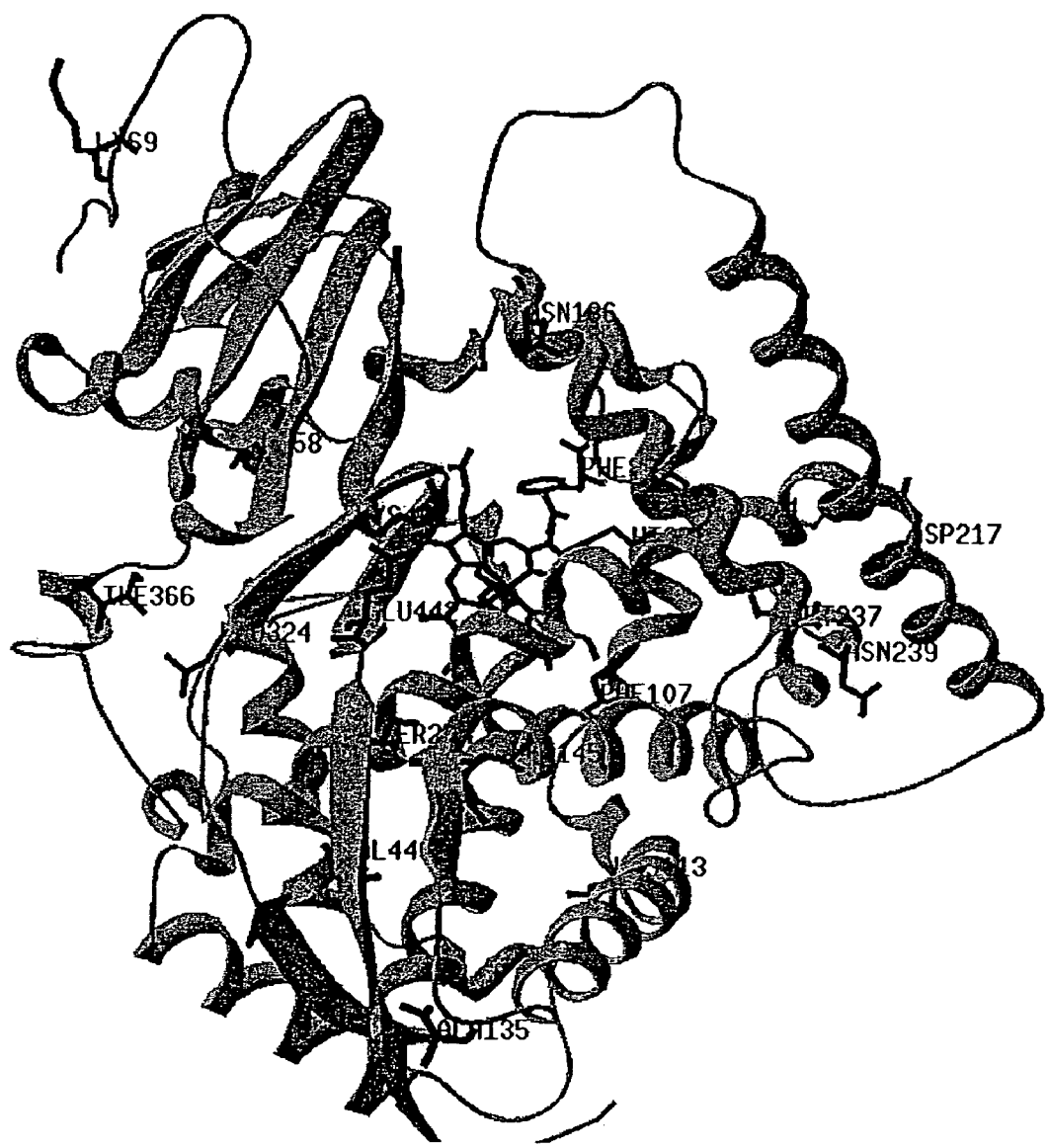
FIG. 6 shows the ribbon drawing of the wild-type cytochrome P450 BM-3 heme domain with conserved secondary structure elements labeled as described in FIG. 5. (A) and (B) each show different views of the P450 BM-3 heme domain, indicating the sites of various mutations described herein. (C) Mutations acquired during evolution of peroxygenase activity and which appear in mutant 21B3 (See WO 02/083868 by Cirino et al.) are shown as black balls. Mutations acquired through further directed evolution of thermostability and which appear in mutant 5H6 are shown in grey balls. The atomic coordinates of P450 BM-3 described in Li and Poulos (1994) were used to create this image with the free-ware program Swiss PDB Viewer (available via the ExPASy (Expert Protein Analysis System) proteomics server of the Swiss Institute of Bioinformatics (SIB) website).
Figure 6B:
Figure 6C:

According to this measure of stability, variant 5H6 ($T_{50}$=61° C.) is more thermostable than the natural catalytic system, BWT ($T_{50}$=43° C.) and the wild-type heme domain ($T_{50}$=57° C.). It is also significantly more thermostable than HF87A and 21B3. The substitutions found in 5H6 are listed in Table 9, and are depicted in FIG. 6C.

TABLE 9

Mutations in thermostable peroxygenase variant 5H6, in addition to F87A. (Percentage values represent the changes in codon usage by E. coli)

| Base Change(s) | Amino Acid Change |
|---|---|
| T154A | L52I |
| A172G | I58V |
| A195T | SILENT (S); 14% to 15% |
| A299G | H100R |
| C318G | S106R |
| C321A | F107L |
| G403T | A135S |
| C489T | SILENT (N); 52% to 48% |
| C551T | A184V |
| A684G | SILENT (E); 67% to 33% |
| A715C | N239H |
| T810C | SILENT (S); 16% to 26% |
| T820A | S274T |
| T970A | L324I |
| G1018A | V340M |
| A1096G | I366V |
| T1188A | SILENT (G); 33% to 13% |
| A1300G | K434E |
| T1309C | SILENT (L); 14% to 4% |
| G1324A | E442K |
| G1336A | V446I |
| CAT (1405, 1406, 1407) DELETED | H469 DELETED |

Throughout the course of evolving shunt pathway activity and stability, the codon for residue position 145 was changed on two separate occasions: from ATG to GTG in 21B3 (mutation M145V) and then to GCG (mutation M145A, which could not be reached by a single base mutation). This mutation was removed during DNA shuffling, resulting in mutant 5H6.

Thermostable peroxygenase 5H6 contains five new amino acid substitutions compared to TH4, which includes the reversion of M145A back to M145: L52I, S106R, M145, A184V, and V340M. 5H6 also contains a deletion resulting in the removal of one His residue from the 6-His sequence included at the C-terminus. Substitutions L52I, A184V, and V340M are conservative with regard to hydrophobicity and size. The serine residue at position 106 was converted to a positively charged Arg residue (S106R). These mutations increased the enzyme's stability. According to the P450 BM-3 heme domain crystal structure, substitutions S106R and V340M are located on the protein surface; the others are buried.

Altogether, four thermostabilizing mutations are close to positions where mutations that improved peroxygenase activity accumulated in earlier experiments: L52I (in β-sheet 1-2) is adjacent to I58V (helix B) from 21B3, S106R (in a loop connecting helices C and D) lies next to mutation F107L from 21B3, E442K (in β-sheet 4-2) lies adjacent to K434E (in β-sheet 4-1) from 21B3, and the reversion to M145 (helix E) is adjacent to S274T (helix I) from 21B3. See FIG. 7. Without being bound to any specific theory, the new stabilizing mutations may therefore alleviate structural perturbations introduced by the original mutations which improved peroxygenase activity.

Enzyme thermostabilization can lead to a shift in the activity-temperature profile to higher temperatures, reflecting the higher stability of the folded protein (Daniel et al., 2001). Measurements of peroxygenase activity at different temperatures, however, showed no significant increase in the optimum temperature for activity for 5H6 compared to HF87A (both were in the range 25-30° C.).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application and in the appended bibliography, the disclosures of which are incorporated herein by reference in their entireties for all purposes.

BIBLIOGRAHY

Appel D, et al. J Biotechnol 2001;88:167-171.
Arnold F H. Acc Chem Res 1998;3:125-131.
Aust S D. Redox Report 1999;4: 195-7.
Barnes H J, et al. Proc Natl Acad Sci USA 1991;88:5597-601.
Beratan, D N T. Protein Electron Transfer, 1996, Oxford: Bios Scientific Publishers.
Boddupalli S S, et al. J Biol Chem 1990;265:4233-4239.
Capdevila J H, et al. J Biol Chem 1996;271:22663-22671.
Chang Y T and Loew G. Biochemistry 2000;39:2484-2498.
Chen H Y, et al. Science 2000;287:1995-1997.
Cirino P C and Arnold F H, Adv. Synth. Catal. 2002(a);344: 932 et seq.
Cirino P C and Arnold F H, Curr Opin Chem Biol. 2002(b); 6(2):130-5.
Cirino P C, et al., in: Directed Evolution Library Creation: Methods and Protocols (Eds.: Arnold F H, Georgiou G), Humana Press, Totowa, N.J., 2003, pp. 3 et seq.
Cirino P C and Georgescu R, in: Directed Enzyme Evolution: Screening and Selection Methods (Eds.: Arnold F H, Georgiou G), Humana Press, Totowa, N.J., 2003, 117-125.
Cirino P C and Arnold F H, Angew Chem-Int Edit 2003;42: 3299-3301. Daniel R M, et al., Trends Biochem. Sci. 2001, 26, 223 et seq.
Farinas E, et al. Adv Syn Catal 2001;343:601-606.
Gordon et al., Chem Biol 1999;6:R269-R272.
Groves J T and Han Y-H. In: Cytochrome P450: Structure, Mechanism, and Biochemistry (Ed.: Ortiz de Montellano, P. R.), Plenum Press, New York, N.Y., 1995, pp. 3-48.
Haines D C, et al. Biochemistry 2001;40:13456-13465.
Hartmann M, and Ernst S. Angew Chem Int Ed 2000;39:888-890.
Joo H, et al. Chem Biol 1999;6:699-706.
Graham-Lorence S E, et al. J Biol Chem 1997:272:1127-1135.
Lehmann M and Wyss M, Curr. Opin. Biotechnol. 2001;12, 371 et seq.
Lehmann M, et al., Biochim. Biophys. Acta 2000;1543:408 et seq.
Lewis D F V. Cytochromes P450: Structure, Function and Mechanism. 1996, London: Taylor & Francis.
Lewis D F V, et al. Toxicology 1999; 139: 53-79.
Li H, et al. J Biol Chem 1991;18:11909-14.
Li Q, et al. Biochem Biophys Res Commun 2001;280:1258-1261.
Li H, and Poulos T L. Nature Struct Biol 1997;4:140-146.
Li H and Poulos T L, Acta Crystallogr 1994;D51:21-32.
Lipman D J and Pearson W R. Science 1985;227;1435-1441.
Martinek K and Mozhaev V V, in Thermostability of Enzymes (Ed.: Gupta Minn.), Springer-Verlag, Berlin, 1993, pp. 76-82.
Matsunaga I, et al. Lipids 2000;4:365-371.
McLean M A, et al., Biochem. Biophys. Res. Commun. 1998; 252:166 et seq.
Miles C S, et al. Biochim Biophys Acta 2000;1543:383-407.
Miura Y and Fulco A J. Biochim Biophys Acta 1975;388,: 305-317.
Moser C C. et al. J Bioenerg Biomembr 1995;27:263-274.
Munro A W, et al. Eur J Biochem 1996;239:403-409.
Munro A W, et al., Trends Biochem. Sci. 2002;27:250 et seq.
Nakagawa et al., Biosci Biotechnol Biochem 1996;60:415-20.
Narhi L O, and Fulco, A J. J Biol Chem 1986;261:7160-7169.
Narhi L O, and Fulco, A J. J Biol Chem 1987;262:6683-6690.
Oliver C F, et al. Biochemistry 1997;36: 1567-72.
Omura T, and Sato, R J. J Biol Chem 1964;239:2379-2385.
Ortiz de Montellano (Ed.), "Cytochrome P450; Structure, Mechanism, and Biochemistry, 2nd Ed., Plenum Press, New York (1995).
Park S Y, et al., J. Inorg. Biochem. 2002;91:491 et seq.
Park S Y, et al., Acta Crystallogr. D Biol. Crystallogr. 2000;56 (Pt 9): 1173 et seq.
Paulsen M D and Ornstein R L. Proteins 1995;21:237-243.
Pearson W R and Lipman D J. Proc Natl Acad Sci USA 1988;85:2444-2448.
Peterson J A and Graham-Lorence S E, "Bacterial P450s: Structural Similarities and Functional Differences". In: Cytochrome P450: Structure, Mechanism, and Biochemistry. 2nd Ed., edited by Ortiz de Montellano, PR. Plenum Press, New York, 1995.
Puchkaev A V, et al., Arch. Biochem. Biophys. 2003;409:52 et seq.
Ravichandran K G et al., J. Deisenhofer, Science 1993;261: 731 et seq.
Ruettinger R T and Fulco A J. J Biol Chem 1981;256:5728-5734.
Ruettinger R T, et al. J Biol Chem 1989;264: 10987-10995.
Schwaneberg et al., J Biomolecular Screening 2001:6; 111-7.
(a) Schwaneberg U, et al. Anal Biochem 1999;269:359-66.
(b) Schwaneberg U, et al. J. Chromatogr. A. 1999;848:149-159.
Shilov A E and Shul'pin G B. Chem. Rev., 1997; 97:2879-2932.
Stemmer W P, Nature 1994;370:389 et seq.
Thomas J M, et al. Acc Chem Res 2001;34:191-200.
van Deurzen M P J et al. Tetrahderon 1997;53:13183-13220.
Wintrode P L and Arnold F H, in: Evolutionary Protein Design, Vol. 55 (Ed.: F. H. Arnold), Academic Press, San Diego, 2001, pp. 161 et seq.
Yano J K, et al., J. Biol. Chem. 2000;275:31086 et seq.
Yeom H and Sligar S G, Arch. Biochem. Biophys. 1997;337: 209 et seq.
Zhao H et al. In: Manual of Industrial Microbiology and Biotechnology 2nd Edition (Eds.: Demain and Davies), ASM Press, Washington D.C., 1999, pp.597-604.

Patent Literature

U.S. Pat. No. 5,741,691
U.S. Pat. No. 5,811,238
U.S. Pat. No. 5,605,793
U.S. Pat. No. 5,830,721
WO 99/60096
WO 98/42832
WO 95/22625
WO 97/20078
WO 95/41653
WO 98/27230
WO 02/083868

What is claimed is:

1. An isolated variant of a cytochrome P450 BM-3 comprising an amino acid sequence that is at least 95% identical to the sequence of SEQ ID NO:13, the variant comprising a first mutation at amino acid residue M145 of SEQ ID NO:13, and a second mutation at amino acid residue N239, of SEQ ID NO:13, wherein the variant has peroxygenase activity.

2. The isolated variant of claim 1, comprising mutations in at least three amino acid residue selected from K9, I58, F87, E93, H100, F107, K113, A135, M145, 145A, A184, N186, D217, M237, E244, S274, L324, I366, K434, E442, and V446 of SEQ ID NO:13, and mutations in at least three amino acid residues selected from L52, S106, N239, and V340 of SEQ ID NO:13.

3. The isolated variant of claim 1, comprising a mutation in L52, I58, F87, H100, S106, F107, A135, A184, N239, S274, L324, V340, I366, K434, E442, and V446 of SEQ ID NO:13.

4. The isolated variant of claim 1, wherein the variant cytochrome P450 BM-3 does not include a reductase domain.

5. The isolated variant of claim 1, wherein the variant has a higher thermostability than a wild-type P450 BM-3.

6. The isolated variant of claim 1, wherein the variant has a higher thermostability than a wild-type cytochrome P450 BM-3 heme domain.

7. The isolated variant of claim 1, wherein the first mutation comprises an M145A or M145V mutation.

8. The isolated variant of claim 1, wherein the second mutation comprises N239H.

9. The isolated variant of claim 1, wherein the variant comprises at least 6 mutations selected from K9I, L52I, I58V, F87A, F87S, E93G, H100R, S106R, F107L, K113E, A135S, M145A, M145V, A184V, N186S, D217V, M237L, N239H, E244G, S274T, L324I, V340M, I366V, K434E, E442K, and V446I of SEQ ID NO:13.

10. The isolated variant of claim 1, wherein the variant comprises the mutations L52I, I58V, F87A, H100R, S106R, F107L, A135S, A184V, N239H, S274T,L324I, V340M, I366V, K434E, E442K, and V446I of SEQ ID NO:13.

11. An isolated variant of a parent cytochrome P450 oxygenase heme domain, the parent cytochrome P450 oxygenase heme domain and having at least 95% sequence identity to SEQ ID NO:13; and the variant comprising a first mutation no more than 10 Angstroms from the first mutation, the second mutation promoting a higher thermostability in the variant, wherein the polypeptide has oxygenase or peroxygenase activity.

12. The isolated polypeptide of claim 11, wherein the polypeptide has a higher capability of using peroxide as an oxygen donor than a wild-type cytochrome P450 oxygenase.

13. The isolated polypeptide of claim 11, having a $T_{50}$ higher than a wild-type cytochrome P450 oxygenase.

14. The isolated variant of claim 7, comprising a third mutation at a residue selected from the group consisting of K9, I58, F87, E93, H 100, F107, K113, A135, A184, N186, D217, M237, E244, S274, L324, I366, K434, E442, V446 and any combination thereof of SEQ ID NO:13.

15. The isolated variant of claim 14, wherein the third mutation comprises K9I, I58V, F87A, F87S, E93G, H100R, F107L, K113E,A135S,A184V, N186S, D217V, M237L, E244G, S274T, L324I, 1366V, K434E, E442K, V446I and any combination thereof.

16. The isolated variant of claim 8, comprising a fourth mutation at a residue selected from the group consisting of L52, S 106 and a combination thereof of SEQ ID NO:13.

17. The isolated variant of claim 16, wherein the fourth mutation comprises L52I, S106R or a combination thereof.

18. The isolated variant of claim 1, comprising 96, 97, 98, or 99% identity to SEQ ID NO:13.

* * * * *

UNITED STATES PATENT AND TRADEMARK OFFICE
CERTIFICATE OF CORRECTION

PATENT NO. : 7,435,570 B2  Page 1 of 1
APPLICATION NO. : 10/916369
DATED : October 14, 2008
INVENTOR(S) : Frances H. Arnold et al.

It is certified that error appears in the above-identified patent and that said Letters Patent is hereby corrected as shown below:

Claims 2, 3, 9 and 15 have an inadvertent typographical error where in each the "I" in "I366" was inadvertently typed in as a "1"; Claims 2, 3, 9 and 15 correctly read:

Col. 91, lines 58-64 delete and insert
--2. The isolated variant of claim 1, comprising mutations in at least three amino acid residue selected from K9, I58, F87, E93, H100, F107, K113, A135, M145, 145A, A184, N186, D217, M237, E244, S274, L324, I366, K434, E442, and V446 of SEQ ID NO:13, and mutations in at least three amino acid residues selected from L52, S106, N239, and V340 of SEQ ID NO:13.--

Col. 91, lines 65-67 delete and insert
--3. The isolated variant of claim 1, comprising a mutation in L52, I58, F87, H100, S106, F107, A135, A184, N239, S274, L324, V340, I366, K434, E442, and V446 of SEQ ID NO:13.--

Col. 92, lines 63-67 delete and insert
--9. The isolated variant of claim 1, wherein the variant comprises at least 6 mutations selected from K9I, L52I, I58V, F87A, F87S, E93G, H100R, S106R, F107L, K113E, A135S, M145A, M145V, A184V, N186S, D217V, M237L, N239H, E244G, S274T, L324I, V340M, I366V, K434E, E442K, and V446I of SEQ ID NO:13.--

Col. 94, lines 6-10 delete and insert
--15. The isolated variant of claim 14, wherein the third mutation comprises K9I, I58V, F87A, F87S, E93G, H100R, F107L, K113E, A135S, A184V, N186S, D217V, M237L, E244G, S274T, L324I, I366V, K434E, E442K, V446I and any combination thereof.--

Signed and Sealed this

Nineteenth Day of January, 2010

David J. Kappos
*Director of the United States Patent and Trademark Office*